United States Patent [19]
Heredia

[11] Patent Number: 5,961,936
[45] Date of Patent: Oct. 5, 1999

[54] ARRANGEMENT FOR ADAPTING A GAS GENERATION AND RECOVERY SYSTEM TO A TARGET VOLUME

[75] Inventor: Leon M. Heredia, Perth Amboy, N.J.

[73] Assignee: Johnson & Johnson, New Brunswick, N.J.

[21] Appl. No.: 08/764,796

[22] Filed: Dec. 12, 1996

[51] Int. Cl.⁶ ......................................... A61L 2/20
[52] U.S. Cl. ............................. 422/292; 422/305; 422/28
[58] Field of Search ................................ 422/28, 31, 105, 422/292, 305

[56] References Cited

U.S. PATENT DOCUMENTS

| | | | |
|---|---|---|---|
| 4,301,113 | 11/1981 | Alguire et al. | 422/34 X |
| 4,764,351 | 8/1988 | Hennebert et al. | 422/27 X |
| 5,252,304 | 10/1993 | Miyoshi | 422/305 |
| 5,290,524 | 3/1994 | Rosenblatt et al. | 422/28 X |
| 5,326,543 | 7/1994 | Fiorenzano, Jr. | 422/32 X |
| 5,422,130 | 6/1995 | Fox et al. | 426/234 |
| 5,662,865 | 9/1997 | Blatchford | 422/305 X |

*Primary Examiner*—Elizabeth McKane
*Attorney, Agent, or Firm*—Joseph F. Shirtz

[57] ABSTRACT

Apparatus and methods for generating, administering, extracting and recovering sterilant gas for sterilizing and/or decontaminating enclosed spaces such as, interior spaces of microbial isolators and also components associated with such apparatus and methods. Specifically contemplated herein, inter alia, is a modular system that includes at least one modular section (A), which includes an arrangement for administering gas to a target and for recirculating gas back to the target, and at least one of: at least one modular section (B) which includes an arrangement for generating a gas and at least one modular section (C) which includes an arrangement for selectively extracting gas away from the target.

7 Claims, 45 Drawing Sheets

FIG. 34
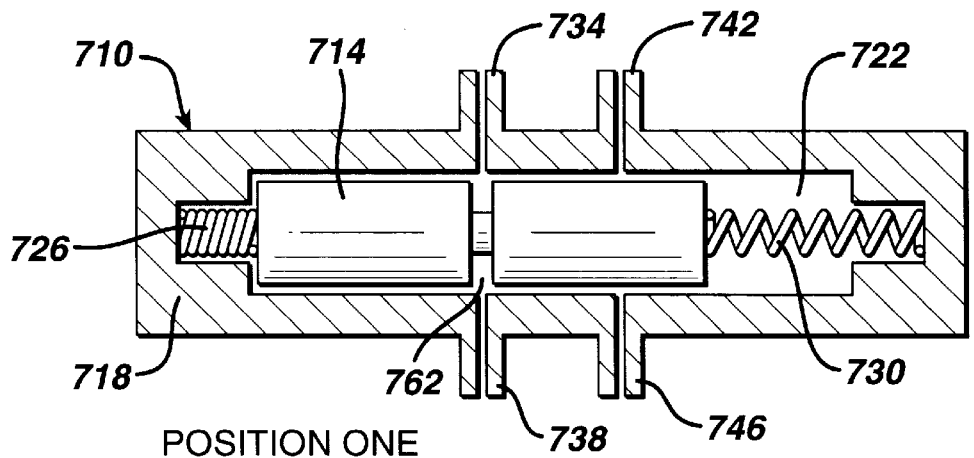
POSITION ONE
FIG. 35
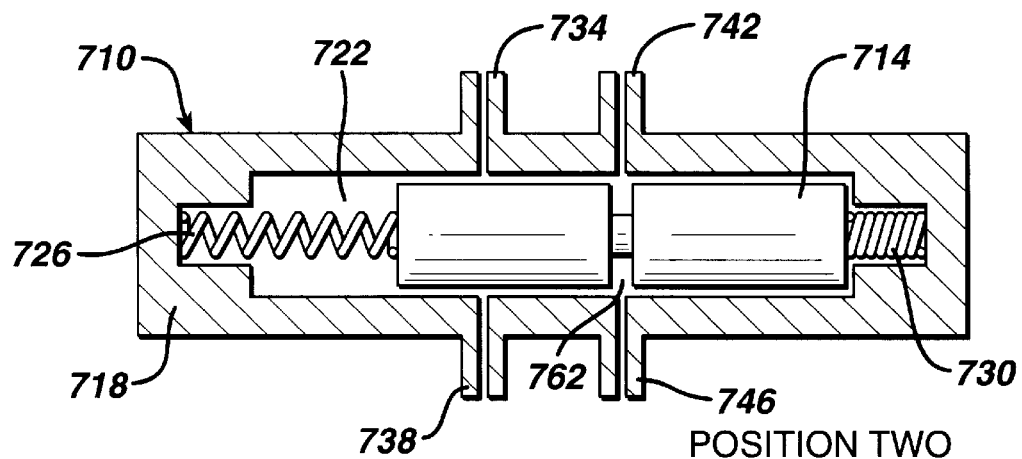
POSITION TWO
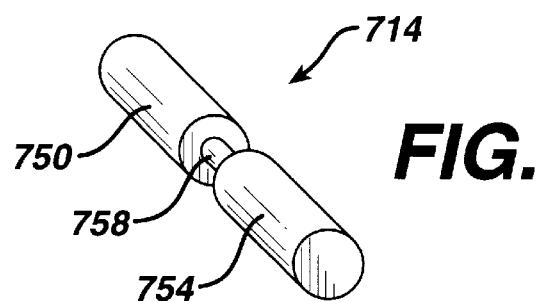
FIG. 36

ARRANGEMENT FOR ADAPTING A GAS GENERATION AND RECOVERY SYSTEM TO A TARGET VOLUME

FIELD OF THE INVENTION

The present invention generally relates to apparatus and methods for generating, administering, extracting and recovering sterilant gas for sterilizing and/or decontaminating enclosed spaces such as, for example, interior spaces of microbial isolators, and also to components associated with such apparatus and methods.

BACKGROUND OF THE INVENTION

Historically, there have been developed a wide variety of enclosed spaces for facilitating the handling, inspection, analysis and/or production of various materials in a sterile and/or decontaminated environment. Examples of such enclosed spaces are (but are not limited to): microbial isolators, sterile transfer bays, industrial spaces, contained volumes, "small-transfer" microbial isolators (such as those having a volume of about 25 cubic feet), microbial isolators with large flexible work stations (such as those having a volume of between about 350 and about 400 cubic feet with two or more flexible-suit work stations), autoclave interface microbial isolators, industrial spaces that require sterilization (such as glass rooms and industrial-scale aseptic processing isolators), and sterilized enclosed spaces used in the food industry for various functions (e.g. for the sterilization of spices, flour bleaching, surface decontamination of given products, etc.).

Some known "glove-type" isolators, which provide long gloves in the shape of a human forearm and that extend inwardly from the outer surface of an isolator into the enclosed space itself, are manufactured by, for example, "la Calhene" of Velizy, France and Laminar Flow, Inc. of Ivyland, Pa. Further, "la Calhene" is known to produce half-suit isolators, such as the "series iso 2100" which involves an airtight suit in the shape of a human torso and extending arm portions, also including a helmet portion, and that extends from the bottom surface of the enclosed space and into the enclosed space itself. Several other types of enclosed spaces, including entire sterile rooms, are disclosed in "Clean Rooms" magazine, Vol. 10, No. 5, May, 1996.

Generally, two types of isolators have been available, namely those with sides or walls that may generally be regarded as "flexible" and those with sides or walls that may generally be regarded as "rigid". Historically, these have been considered as being virtually interchangeable with one another and/or equivalent in their performance, function and operation, and their use or desirability of use has often been governed by little more than considerations of cost.

Historically, in order to effect the actual sterilization or decontamination of enclosed spaces such as those described hereabove, there have been proposed numerous apparatus for providing in such enclosed spaces appropriate quantities of sterilant gas, in appropriate proportional concentrations of various compounds known to provide a sterilizing or decontaminating effect.

Recently, many efforts have focused upon: the generation of a gas or compound believed to be appropriate to help effect sterilization or decontamination within the space in question; the efficient application of such a gas or compound to the space to be sterilized or decontaminated; and the environmentally-sensitive disposal and/or recovery of such gases or compounds once they have been used for the purpose of sterilizing or decontaminating the space in question.

A need has also often been observed in connection with providing sterilization/decontamination apparatus that do not necessarily require permanent attachment to a given enclosed space, i.e., that are sufficiently portable and versatile as to be connectable or disconnectable with a single enclosed space or type of enclosed space.

Further, a need has been observed in connection with providing sterilization/decontamination apparatus that are sufficiently portable and versatile as to be connectable or disconnectable, on different occasions, with different enclosed spaces or types of enclosed spaces.

Although many different types of gases or compounds have been proposed for use as sterilants or decontaminants in the context described hereinabove, many have been found to be not as effective as desired or as not lending themselves to facilitated environmentally-safe disposal or recovery once sterilization/decontamination procedures have been completed. Over the years, the use of chlorine dioxide gas as a sterilizing agent has been widely recognized. Its use in such a capacity is described, for example, in the following U.S. Patents to Rosenblatt et al.: U.S. Pat. Nos. 5,326,546; 5,290,524; 5,234,678; 5,110,580; 4,681,739 and 4,504,442. Manners of generating chlorine dioxide gas in such a capacity are also disclosed among the aforementioned patents. However, a need has been recognized to utilize chlorine dioxide gas as a sterilant in an efficient manner that provides effective sterilization or decontamination capabilities, that lends itself to facilitated exhaustion into the ambient atmosphere in an environmentally-safe manner as well as efficient recovery of a designated active ingredient or ingredients, and that can be controlled in a manner most conducive to undertaking the sterilization or decontamination task at hand.

The present discussion will now turn briefly to various subsidiary components of sterilization/decontamination apparatus, as well as processes for manipulating and/or controlling apparatus and/or their constituent components, for which particular needs have been recognized.

Sterilization/decontamination apparatus have often included, among other components, an arrangement for generating sterilant gas and an arrangement for recovering and/or exhausting used gas. "Recovery" normally involves the task of retaining at least one active ingredient of a sterilant gas once it has been used in a sterilizing procedure, while "exhausting" normally involves the environmentally-safe expulsion of used sterilant gas, or at least portions thereof, into the ambient atmosphere.

Conventionally, gas recovery systems for use in sterilization/decontamination apparatus often include arrangements in which incoming gas, that is to be exhausted or recovered, will be directed into a container that holds a "scrubber solution". In this, what may be termed a "liquid-based system", the gas is thus forced through a column of liquid having a significant hydrostatic head, so that bubbles of gas will appear shortly thereafter at the surface of the column of liquid. Conceivably, the incoming gas will have sufficiently interacted with the scrubber solution so as to have been effectively "scrubbed" or even neutralized by the time it arrives at the surface of the column of liquid. The resultant "bursting" of bubbles at the upper surface of the liquid column will then result in the further upward expulsion of "scrubbed" gas, then either to be exhausted directly into the ambient atmosphere or to be sent to a "post-scrubber" arrangement for recovery of at least one active ingredient. "Soda-lime" post-scrubbers have been used for at least the latter purpose.

Several drawbacks have been recognized in conjunction with such liquid-based systems. First, it is generally necessary to maintain a relatively large hydrostatic head of the scrubber solution within the container, in order that the incoming gas will be sufficiently "scrubbed" prior to being sent either to the ambient atmosphere and/or to a postscrubber such as that mentioned above. Since the hydrostatic head would appear to be a critical parameter, it has often been the case that very large hydrostatic heads have been required. This, in turn, will usually present the disadvantage that a significant degree of pressure, associated with the entry of the incoming gas into the recovery system, is required in order for the gas to sufficiently progress upwardly through the liquid column in the first place. In the presence of a significantly high hydrostatic head, this pressure, often referred to as "back-pressure", can be significant, with the result that the "back-pressure" is effectively transmitted rearwardly back into the sterilization/decontamination apparatus, with the possible result of damage to valves and/or other components. It has often been found that the service life of given components in a sterilization/decontamination apparatus is effectively shortened because of such back-pressure or that very elaborate and expensive valve arrangements are required within the system in order to withstand such high degrees of back pressure. As a result of this back-pressure, it has been the case that expensive and/or bulky pumps have been required to effectively propagate the incoming gas upwardly through the column of scrubber solution.

In the context of sterilization/decontamination apparatus (and elsewhere), the importance of measuring relative concentrations of given gases and/or compounds during a sterilization/decontamination procedure has been widely recognized. Particularly, a need has been recognized in conjunction with measuring the relative concentration of "sterilant" portions of gas while being directed into and out of an enclosed space, or while in the enclosed space, in order to ensure that it falls within an acceptable range. Furthermore, many conventional measuring devices lack the capability to be utilized for more than one specific, predetermined purpose. Therefore, a need has been recognized for versatile gas measurement devices that eliminate the deficiencies associated with conventional measurement devices.

Historically, a wide range of control valves have been used in conjunction with sterilization/decontamination apparatus. However, many of the valves proposed to date have been relatively complex, expensive and not reliably hermetically tight. Therefore, a need has arisen for the provision of simple, inexpensive and hermetically tight valves both in the context of sterilization sciences and elsewhere.

A need exists for other simple and inexpensive valving systems and/or valve operation schemes, particularly in the context of inflating and deflating sterilization/decontamination spaces (particularly if the walls are flexible) or at least flushing enclosed spaces, introducing sterilant gas into such spaces and subsequently extracting the sterilant gas.

In the context of sterilization/decontamination apparatus, there has also historically been a need for effective software or other programming logic capable of effectively controlling the components and sub-components of the apparatus.

In this context, a particular need has arisen in conjunction with permitting the admission of a sterilant gas into an isolator (or other enclosed space) under controlled conditions for a defined period of time. In this vein, difficulties have often been encountered in defining, planning and programming any software or programming logic that may be required to bring a new sterilization/decontamination apparatus on-line (i.e., to establish its operating parameters in such a manner that it is able to effectively perform a sterilizing or decontaminating process). A need has also arisen in conjunction with modifying any existing control programs (or programming logic) to accommodate any new control functions or new operating environments and also "validating" a sterilization/decontamination apparatus on-line (i.e., to establish "worst-case" operating parameters in such a manner that it is able to demonstrate and verify that the system can effectively perform a sterilizing or decontaminating process under "worst-case" conditions).

Finally, many problems have been observed to date, in conventional sterilization/decontamination apparatus, in conjunction with properly "charging" the circulating air/gas in the apparatus so as to accurately infuse proper concentrations of sterilant gas into the system at start-up. Particularly, in the past, many conventional apparatus have based "charging" on direct measurement of gas concentration in the enclosed space to be sterilized or decontaminated. However, such direct measurements are only accurate after the sterilant gas has uniformly distributed throughout the enclosed space. Thus, valuable time is often wasted while awaiting a state in which accurate measurements can be taken. Accordingly, any attempt to continue a sterilizing process before such a state has been achieved could result in inaccurate measurements. Further, many conventional sterilizing or decontaminating processes have estimated gas concentrations at "charging" based on pressure change within the enclosed space, which is an indirect and thus potentially inaccurate estimate of the concentration, or even the mere presence, of sterilant gas in the enclosed space. Finally, many spaces which are to be sterilized or decontaminated cannot be evacuated and have required manual sterilization or decontamination, thus involving potentially significant expenditures of human time and effort and introducing the potentially harmful risk of human error.

SUMMARY OF THE INVENTION

At least one presently preferred embodiment of the present invention broadly contemplates a system for decontaminating at least a portion of a target, the system comprising:

an arrangement for generating a decontaminant gas;

an arrangement for administering the decontaminant gas to the target;

an arrangement for circulating decontaminant gas; and an arrangement for extracting decontaminant gas, the extracting arrangement comprising:

an arrangement for accepting decontaminant gas that has been administered to the target;

an arrangement for recovering at least one ingredient from decontaminant gas accepted by the accepting arrangement, the recovering arrangement comprising an arrangement for introducing a medium for interacting with the accepted decontaminant gas and promoting the recovery therefrom of at least one predetermined ingredient; and a selectively removable arrangement for holding a predetermined quantity of the interacting medium.

Another presently preferred embodiment of the present invention broadly contemplates apparatus for extracting a gas from at least a portion of a target having been exposed to the gas, the apparatus comprising:

an arrangement for accepting gas that has been administered to the target;

an arrangement for recovering at least one ingredient from gas accepted by the accepting arrangement, the recovering arrangement comprising an arrangement for introducing a medium for interacting with the accepted gas and promoting the recovery therefrom of at least one predetermined ingredient; and a selectively removable holding arrangement for holding a predetermined quantity of the interacting medium.

A further presently preferred embodiment of the present invention broadly contemplates a system for decontaminating at least a portion of a target, the system comprising:

an arrangement for generating a decontaminant gas;

an arrangement for administering the decontaminant gas to the target;

an arrangement for circulating decontaminant gas;

an arrangement for extracting decontaminant gas; and an arrangement for determining the concentration of a given component of the decontaminant gas, the determining arrangement comprising:

an arrangement for emitting radiation at a predetermined intensity through a flow of the decontaminant gas;

an arrangement for resolving the emitted radiation to a wavelength compatible with the absorption spectrum of at least one selected component of the decontaminant gas;

an arrangement for receiving at least a portion of the emitted radiation and for measuring at least a portion of the radiation not absorbed by the flow of decontaminant gas, to determine a concentration of the given component of the decontaminant gas;

an arrangement for sensing the intensity of the radiation emitted by the emitting arrangement; and an arrangement, responsive to the sensing arrangement, for providing a correcting feedback to the emitting arrangement.

Yet another presently preferred embodiment of the present invention contemplates apparatus for determining the concentration of at least one component of a fluid, the apparatus comprising:

an arrangement for emitting radiation at a predetermined intensity to a fluid;

an arrangement for resolving the emitted radiation to a wavelength compatible with the absorption spectrum of at least one selected component of the fluid;

an arrangement for receiving at least a portion of the emitted radiation and for measuring at least a portion of the radiation not absorbed by the fluid, to determine a concentration of the given component of the fluid;

an arrangement for sensing the intensity of the radiation emitted by the emitting arrangement; and an arrangement, responsive to the sensing arrangement, for providing a correcting feedback to the emitting arrangement.

An additional presently preferred embodiment of the present invention broadly contemplates a system for decontaminating at least a portion of a target, the system comprising:

an arrangement for generating a decontaminant gas;

an arrangement for administering the decontaminant gas to the target;

an arrangement for circulating decontaminant gas;

an arrangement for extracting decontaminant gas;

at least one conduit; and an arrangement for selectively and alternately admitting and restricting the flow of gas through the conduit, the arrangement for admitting and restricting comprising:

a housing;

a driven element being slideably disposed within the housing;

an arrangement for slidingly displacing the driven element;

the displacing arrangement comprising an arrangement for selectively advancing and retracting the driven element; and an arrangement for providing a locating feedback to the displacing arrangement to ensure substantially precise positioning of the driven element within the housing.

Another additional presently preferred embodiment of the present invention broadly contemplates a system for decontaminating at least a portion of a target volume, the system comprising:

an arrangement for providing decontaminant gas;

an arrangement for selectively initiating the administration of decontaminant gas into the target volume;

an arrangement for selectively permitting the permanent extraction of gas from the target volume; and an arrangement for selectively initiating the recirculation of decontaminant gas back to the target volume.

Yet another presently preferred embodiment of the present invention broadly contemplates a method for decontaminating at least a portion of a target volume, the method comprising the steps of:

providing decontaminant gas;

selectively initiating the administration of decontaminant gas into the target volume;

selectively permitting the permanent extraction of gas from the target volume; and selectively initiating the recirculation of decontaminant gas back to the target volume.

Still another presently preferred embodiment of the present invention broadly contemplates a system for decontaminating at least a portion of a target volume, the system comprising:

an arrangement for providing decontaminant gas;

an arrangement for selectively initiating the administration of decontaminant gas into the target volume;

an arrangement for selectively permitting the permanent extraction of gas from the target volume; and a sequencing arrangement, for automatically, and in a selected one of a predetermined and a predeterminable sequence, carrying out at least two of the steps of: providing decontaminant gas; initiating the administration of decontaminant gas into the target volume; and extracting gas from the target volume.

Another presently preferred embodiment of the present invention broadly contemplates a method for decontaminating at least a portion of a target volume, the system comprising:

providing decontaminant gas;

selectively initiating the administration of decontaminant gas into the target volume;

selectively permitting the permanent extraction of gas from the target volume; and carrying out at least two of the following steps automatically and in a selected one of a predetermined and a predeterminable sequence: providing decontaminant gas; initiating the administration of decontaminant gas into the target volume; and extracting gas from the target volume.

A further presently preferred embodiment of the present invention broadly contemplates a system for generating, administering, circulating and extracting a gas for decontaminating at least a portion of a target volume, the system comprising:

an arrangement for selectively administering decontaminant gas into the target volume at a predetermined flowrate; and an arrangement for continuing the administration of decontaminant gas into the target volume for a period of time that is a function of at least the flowrate into the target volume.

Yet another presently preferred embodiment of the present invention broadly contemplates a method of operating a system for generating, administering, circulating and extracting a gas for decontaminating at least a portion of a target volume, the method comprising the steps of:

selectively administering decontaminant gas into the target volume at a predetermined flowrate; and continuing the administration of decontaminant gas into the target volume for a period of time that is a function of at least the flowrate into the target volume.

Finally, another presently preferred embodiment of the present invention broadly contemplates a modular system for decontaminating at least a portion of a target, the modular system comprising:

at least one modular section (A) comprising an arrangement for:
  selectively administering the decontaminant gas to the target; and
  selectively recirculating gas back to the target; and
at least one of:
  at least one modular section (B) comprising an arrangement for generating a decontaminant gas; and
  at least one modular section (C) comprising an arrangement for selectively extracting decontaminant gas away from the target.

BRIEF DESCRIPTION OF THE DRAWINGS

The present invention and its presently preferred embodiments will be better understood by way of reference to the detailed disclosure herebelow and to the accompanying drawings, wherein:

FIG. 34 illustrates a simple shuttle valve arrangement in a first position;

FIG. 35 illustrates the same valve arrangement as FIG. 34 but in a second position;

FIG. 36 illustrates, in perspective view, a shuttle for use with the shuttle valve illustrated in FIGS. 34 and 35;

DESCRIPTION OF THE PREFERRED EMBODIMENTS

GENERAL OVERVIEW

For the purposes of the present discussion, and throughout the entire instant disclosure, it can be assumed, if not otherwise noted, that the terms "sterilant", "sterilizing" and others based on the root forms "steriliz-" and/or "steril-" can broadly encompass concepts related to, but not necessarily exactly equivalent to, sterilization. Such concepts are not necessarily limited to decontamination, cleaning, contaminant purging, disinfecting, and other concepts of a substantially equivalent nature and scope.

Figure 1:
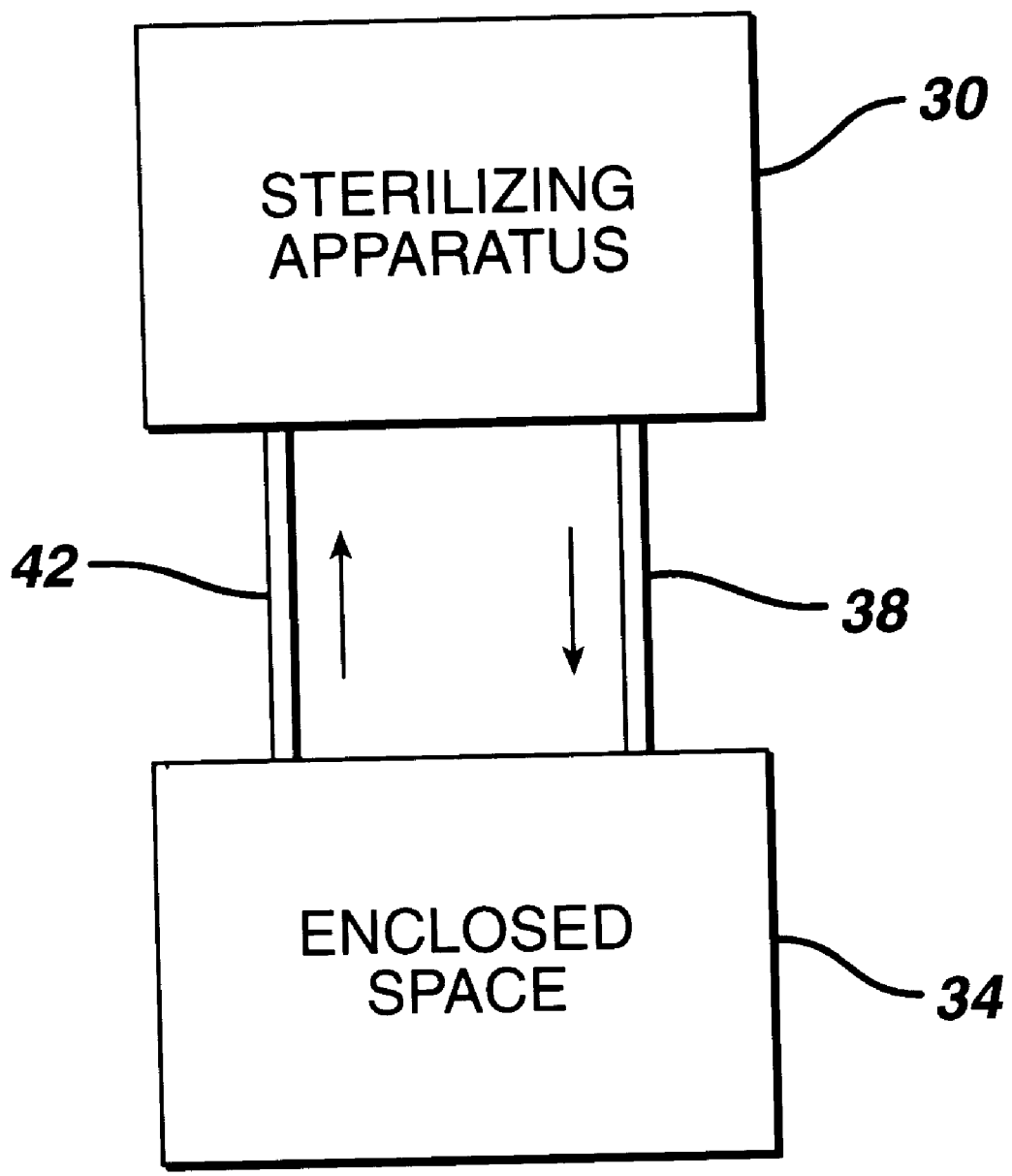
FIG. 1 is a schematic illustration of a conventional sterilizing apparatus and an enclosed space interfaced therewith.

Typically, as schematically illustrated in FIG. 1, a sterilizing apparatus 30 may be provided to sterilize the air or gas present within a given enclosed space 34, as well as any object or objects contained therein. Examples of such enclosed spaces include (but are not limited to): microbial isolators; sterilized rooms; sterilized spaces in the context of the production of items requiring sterilization or decontamination (such as spices, foods, pharmaceutical products, or elastic bandages); and sterilized spaces in surgical operating rooms. A more detailed discussion of such enclosed spaces is provided at the beginning of this disclosure.

As shown in FIG. 1, the general purpose of a sterilizing apparatus 30 is essentially to afford the provision of sterilant gas into, and extraction of the same out of, the enclosed space 34. For this purpose, there will characteristically be provided appropriate conduits 38 and 42 which, respectively, may direct air or sterilant gas from sterilizing apparatus 30 to enclosed space 34 and thence extract such air or sterilant gas from enclosed space 34. Conduit 42 is also used to collect air or gas initially present in enclosed space 34.

Figure 2:
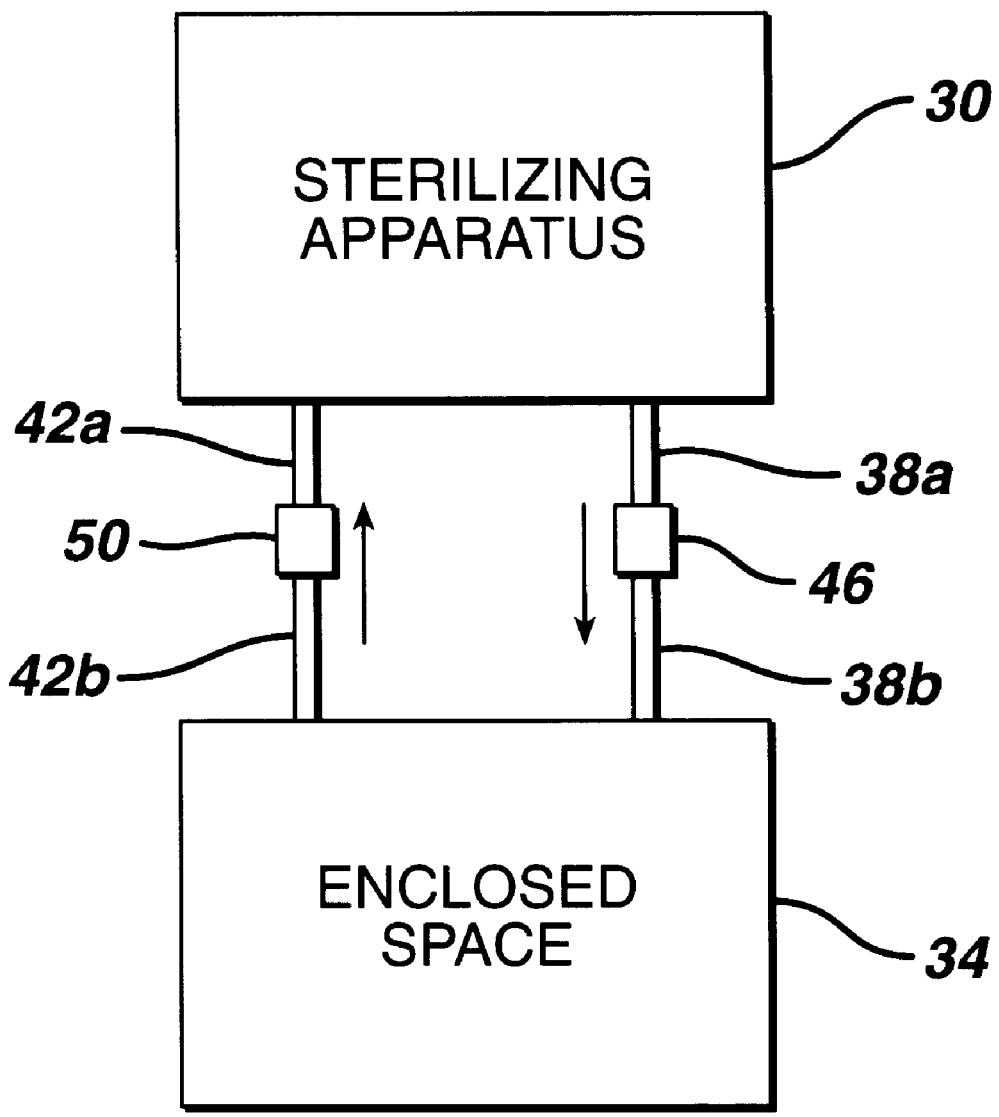
FIG. 2 is essentially the same view as FIG. 1 but further illustrating a connection scheme between the sterilizing apparatus and enclosed space.

FIG. 2 is a slightly more detailed illustration of the arrangement shown in FIG. 1. Particularly, insofar as it is conceivable for either sterilizing apparatus 30, or closed space 34, or both, to be self-contained and portable, FIG. 2 schematically illustrates the possibility of such components being selectively integrable with one another on separate occasions.

Thus, sterilizing apparatus 30 may be considered as having an outlet portion 38*a* and an inlet portion 42*a*, respectively, for the purposes of propagating sterilant or gas outwardly and receiving the same back into its interior. Similarly, enclosed space 34 may be considered as including an inlet portion 38*b* for receiving air or sterilant gas from an external source, such as sterilizing apparatus 30, and an outlet portion 42*b* for returning sterilized air or gas to the external source (or initially providing air or gas to the external source prior to its being sterilized). Thus, insofar as sterilizing apparatus 30 and enclosed space 34 may be considered as being separate, there may be provided connection schemes 46 and 50 for affording the connectability of sterilizing apparatus 30 and enclosed space 34 with one another.

Thus, a first connection scheme 46 may be present so as to couple the outlet portion 38*a* of sterilizing apparatus 30 with the inlet portion 38*b* of enclosed space 34. Further, a second connection scheme 50 may be present to afford the connection of outlet portion 42*b* of enclosed space 34 with inlet portion 42*a* of sterilizing apparatus 30. As discussed further below, the present invention contemplates, in accordance with at least one preferred embodiment, a portable sterilizing or decontaminating apparatus that is selectively connectable to any of a wide range of enclosed spaces.

The disclosure will now turn to a brief description of some conventional enclosed spaces, followed by a brief discussion of a type of enclosed space that can advantageously be used in conjunction with a sterilizing apparatus according to the present invention.

Figure 3:
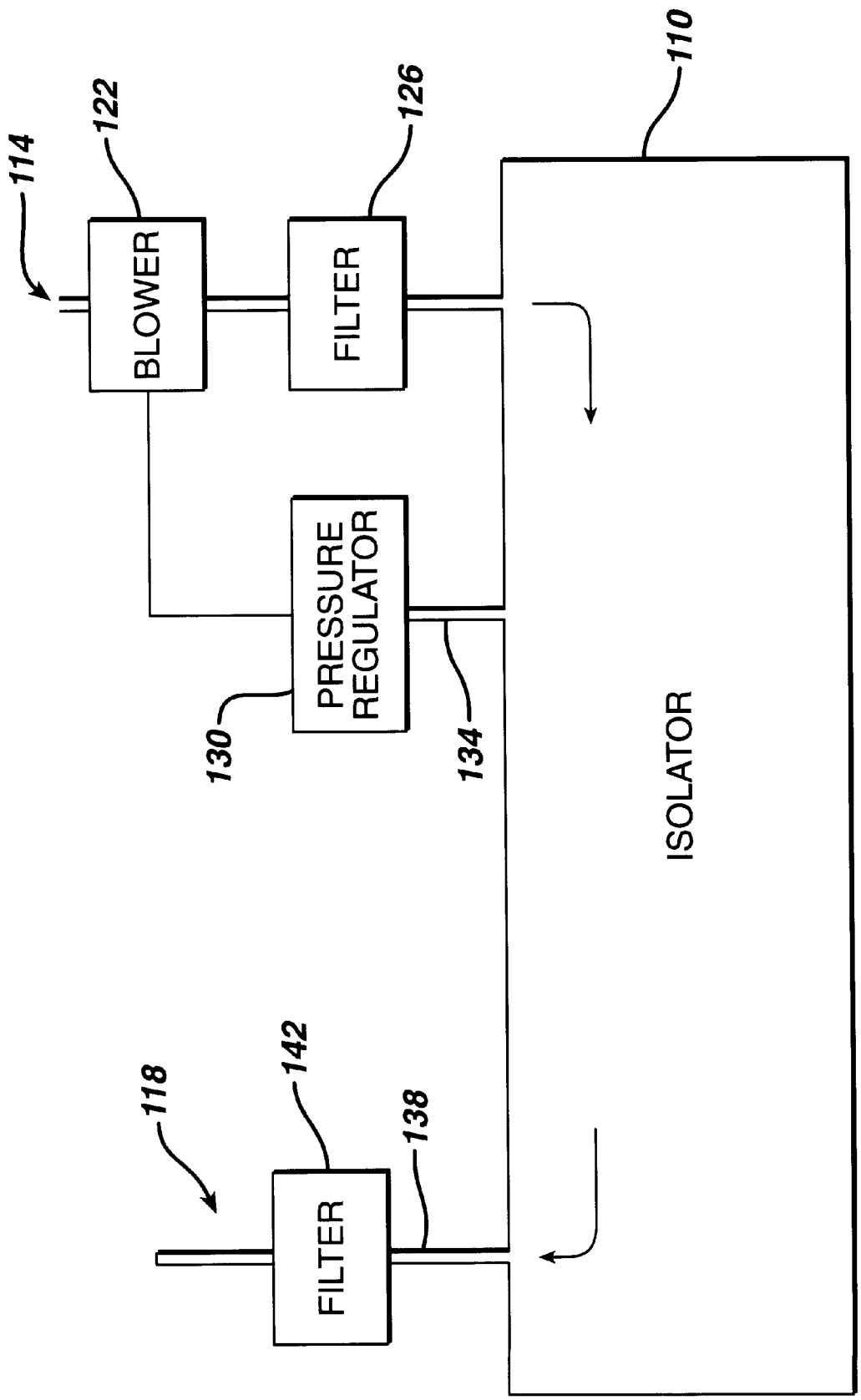
FIG. 3 schematically illustrates a conventional isolator and associated components.

FIG. 3 schematically illustrates a conventional isolator 110 (such as a microbial isolator) and associated components.

Typically, such an isolator 110 may include an inlet portion (generally indicated at 114) and an outlet or exit portion (generally indicated at 118), the purpose and function of which portions will be more fully appreciated hereebelow. Such inlet and outlet portions may be configured for being connected to a separate, external device, such as a sterilizing apparatus, in order to permit the interior of isolator 110 to be sterilized.

Typically, inlet portion 114 may include a blower 122 which directs air through a filter 126 into isolator 110. A pressure regulator 130 may be connected to blower 122 and may also be connected via a suitable line 134 to isolator 110. There may also be an outlet line 138 leading away from isolator 110, through another filter 142, at exit portion 118. Filters 126 and 142 may conceivably be embodied by those produced according to "HEPA" (i.e., High Efficiency Particulate Filter) specifications.

Figure 4:
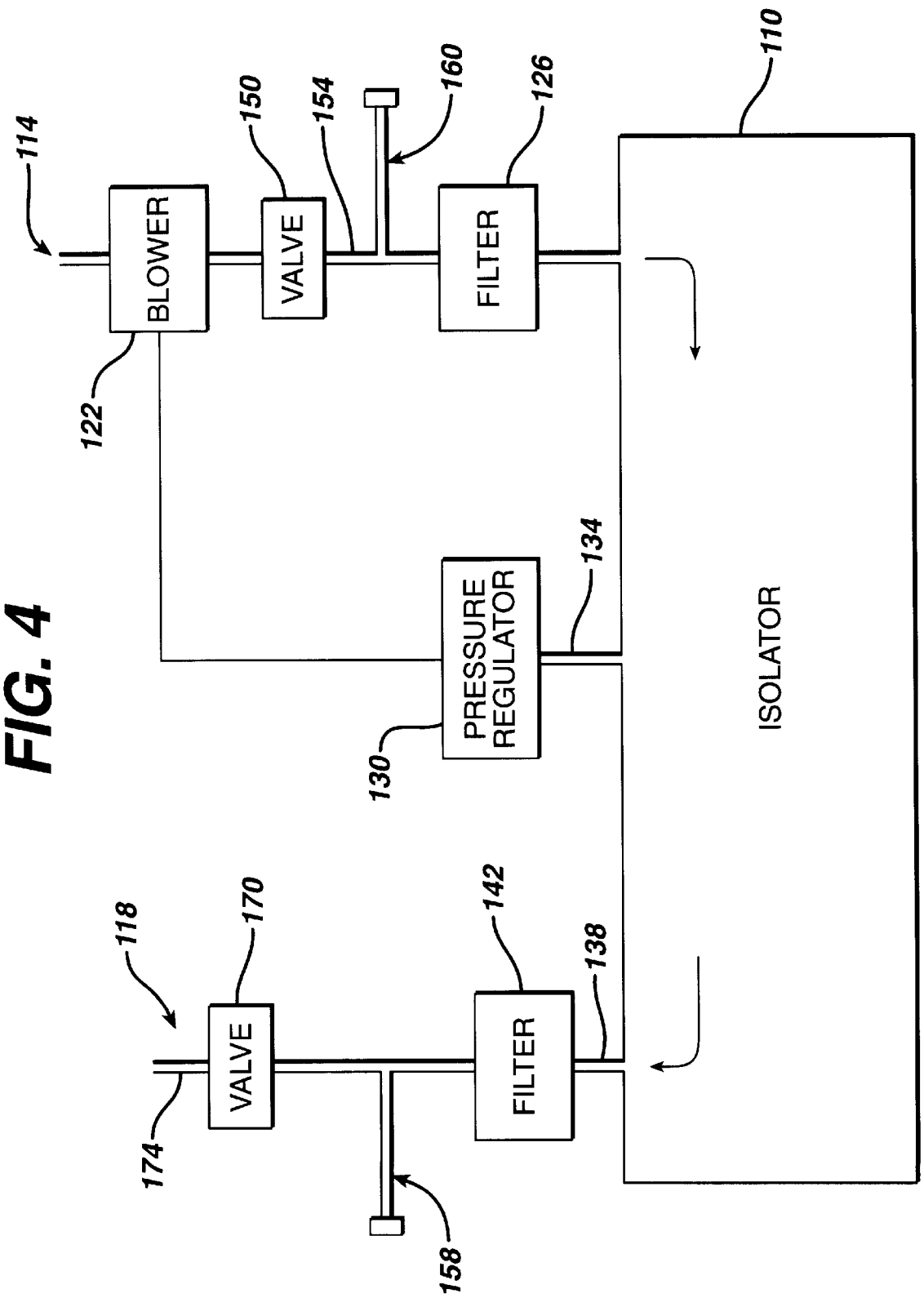
FIG. 4 schematically illustrates an isolator with conventional modifications to accommodate gas sterilization.

FIG. 4 schematically illustrates an isolator 110 with some conventionally known modifications. A system cabinet (not shown in any greater detail) has leading therefrom a line 146, which itself leads through a blower 122 into a valve 150. As in the arrangement shown in FIG. 3, a pressure regulator 130 is connected to blower 122. A line 154 leading from valve 150 also feeds through a filter (such as a "HEPA" filter) 126 into isolator 110. However, some differences with comparison to FIG. 3 may be found in that capped connections for a gaseous sterilizing apparatus are provided. Capped connection 160 provides an inlet for sterilant gas, while capped connection 158 provides an outlet for sterilant gas.

Another difference with respect to FIG. 3 is that, although there is an outlet line 138 leading through a filter (such as a "HEPA" filter) 142, there is also found at exit portion 118 another valve 170, leading to another line 174 that itself, when connected to a sterilizing apparatus, is designated to lead to the aforementioned system cabinet.

Figure 5:
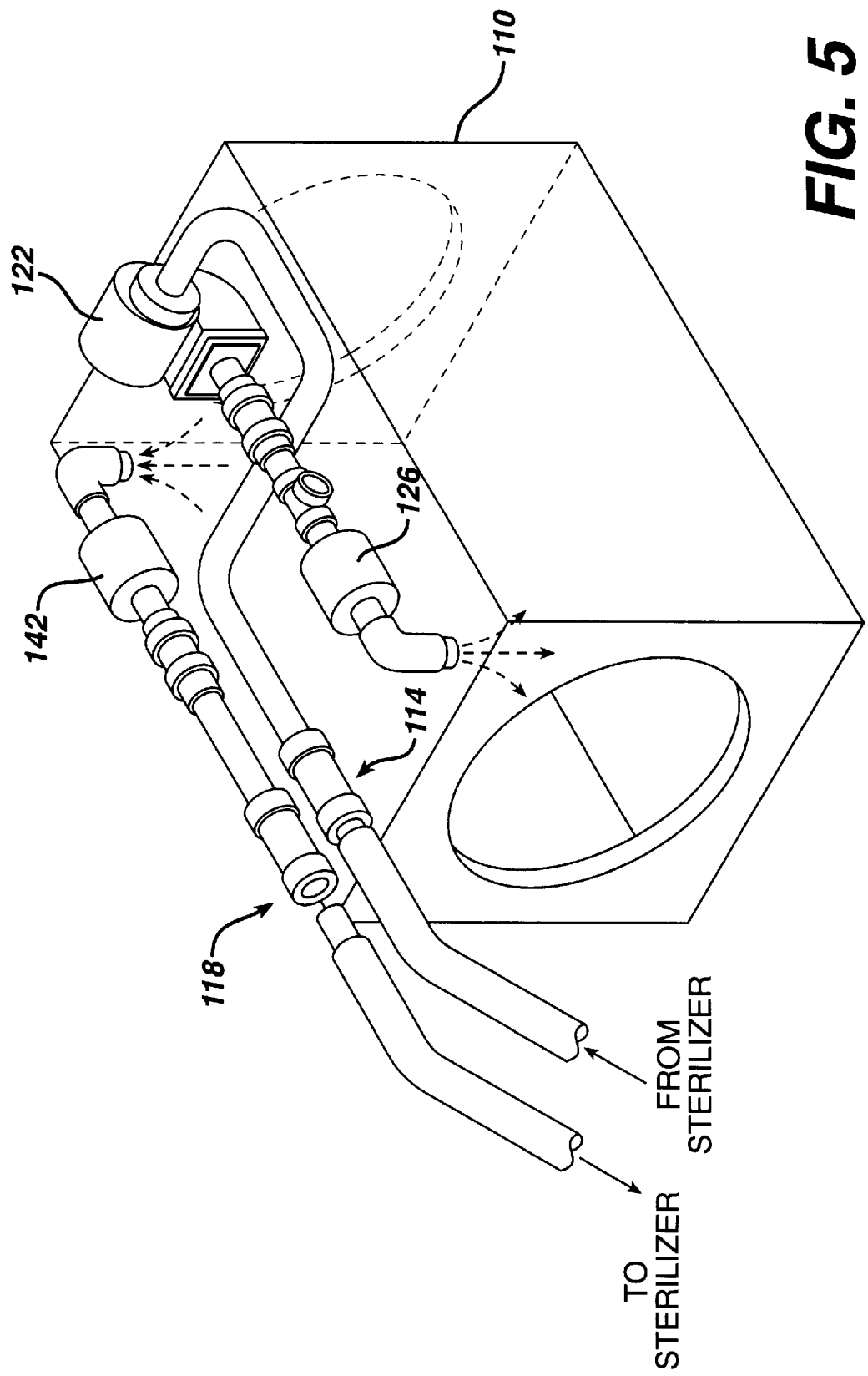
FIG. 5 illustrates an alternative isolator arrangement that may be employed in accordance with the embodiments of the present invention.

In contrast, FIG. 5 illustrates an alternative isolator arrangement 110 that may be employed in accordance with the embodiments of the present invention. Shown, in perspective view, are blower 122, filters 126 and 142, as well as inlet and outlet portions 114 and 118.

Figure 6:
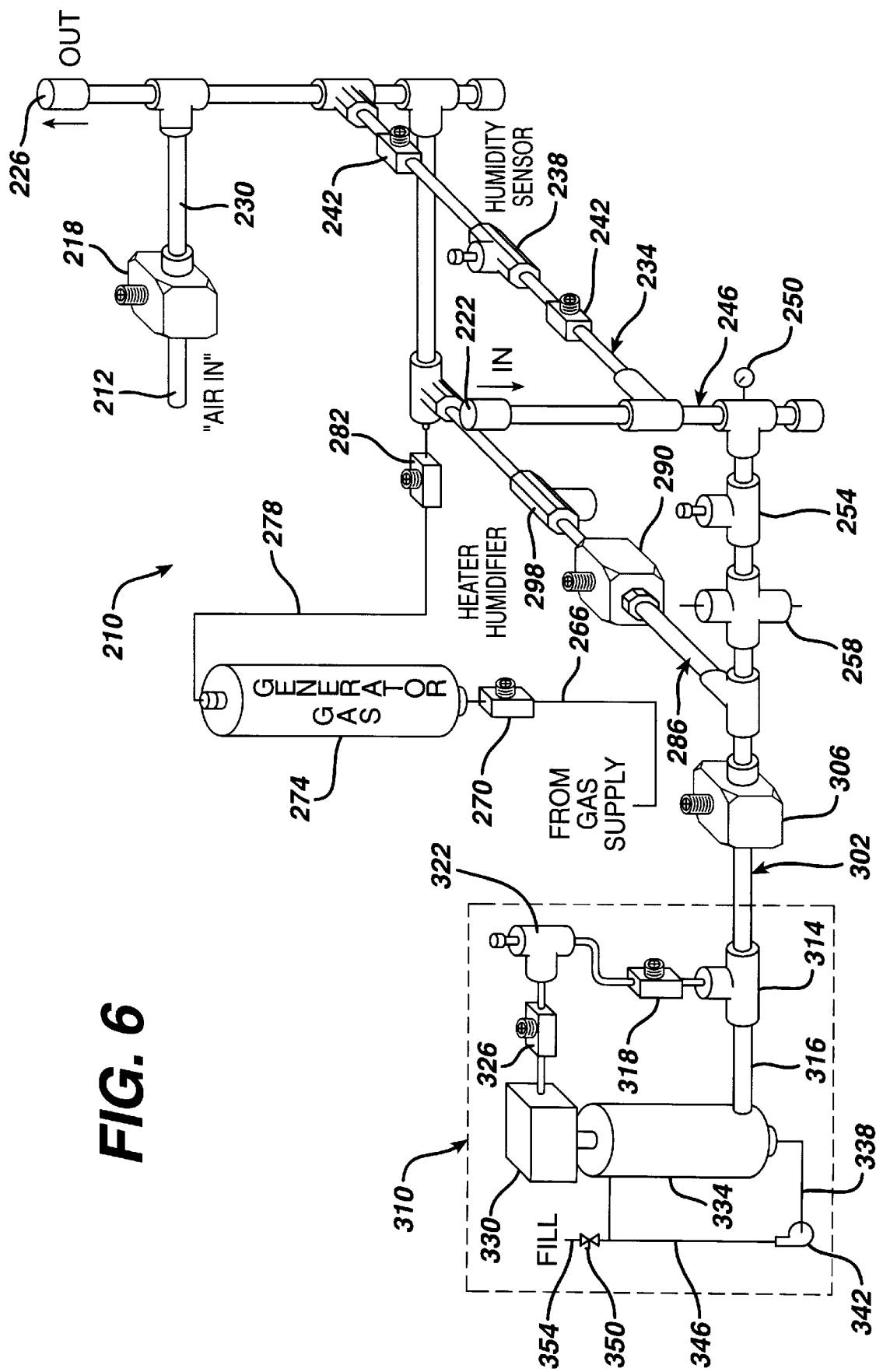
FIG. 6 illustrates, in perspective view, a gas generating and recovery system that may be utilized in accordance with the embodiments of the present invention.

FIG. 6 illustrates, in perspective view, a gas generating and recovery system 210 that may be utilized in accordance with at least one embodiment of the present invention.

An "air in" portion, indicated at 212, leads to a valve 218 that may be configured in a manner to be described more fully below and will presently be referred to as a "control valve".

There may preferably be provided an inlet 222 and an outlet 226 which, respectively, may be connectable to appropriate lines of an external device, such as a microbial isolator. Preferably, a line leading from control valve 218 and "air in" portion 212 will lead to a junction in the vicinity of outlet 226.

In accordance with at least one preferred embodiment of the present invention, inlet 222 will preferably be configured so as to accept air or gas from a microbial isolator (or other enclosed space). Accordingly, outlet 226 will preferably be so configured as to feed air or gas so sterilized back to the microbial isolator (or other enclosed space) in order to sterilize the isolator or enclosed space.

A branch line 234, spanning between lines associated with inlet 222 and outlet 226, may include a humidity sensor 238. On either side of the humidity sensor 238, positioned along line 234, there may be suitable valves 242.

Continuing along the "inlet" line, indicated generally at 246, there may preferably be provided a pressure sensor 250, followed by temperature sensor 254 and a cross-flow cell 258. As will be described in more detail further below, the cross-flow cell 258 could serve as a suitable location for an optical gas measurement system.

In what may be termed the gas generator portion 260 of the device (see FIG. 8), there may be provided a line 266 that originates from a gas supply (not shown). This, in turn, may subsequently lead to valve 270 and a gas generator 274. From the gas generator 274, another line, for carrying chlorine dioxide gas 278, may lead into another valve 282 and then into the system piping proper.

Another line 286 spanning between the "inlet" and "outlet" sides of the device, for the purpose of returning circulating air or gas from the "inlet" side of the device to the "outlet" side of the device, may include, starting with the "inlet" portion, a control valve 290 (possibly similar in makeup and function to the aforementioned control valve 218) and a humidifier 298. Humidifier 298 will preferably be configured to variably control the humidity of circulating gas by any suitable means (for example, by increasing the water content of the gas via a conventional atomizer or evaporator and/or by decreasing the water content of the gas by adding dry air).

Preferably, there will be a "scrubber branch line" (generally indicated at 302) leading away from a junction with cross-line 286. Immediately subsequent to this junction, a control valve 306 may be provided, which could possibly be similar in appearance and function to the aforementioned control valve 218. Line 302 will then preferably lead into a recovery arrangement, indicated schematically via dotted lines at 310. This recovery arrangement 310 will also be described in more detail further below.

Proceeding from a junction 314, in a clockwise direction with respect to FIG. 6, there may preferably be provided: inlet 316, a scrubber 334, a post-scrubber 330, a valve 326, a low-level chlorine dioxide sensor 322, and another valve 318. Preferably, post scrubber 330 will be in appropriate fluid communication with a scrubber 334.

From the bottom of scrubber 334, a line 338 will preferably lead into a pump (or suitable equivalent) 342, which itself will preferably feed, via a line 346, back to the top of scrubber 334. Preferably, in the close vicinity of the point at which line 346 enters the top of scrubber 334, there will be a valve 350 and a "fill" portion 354.

Figure 7:
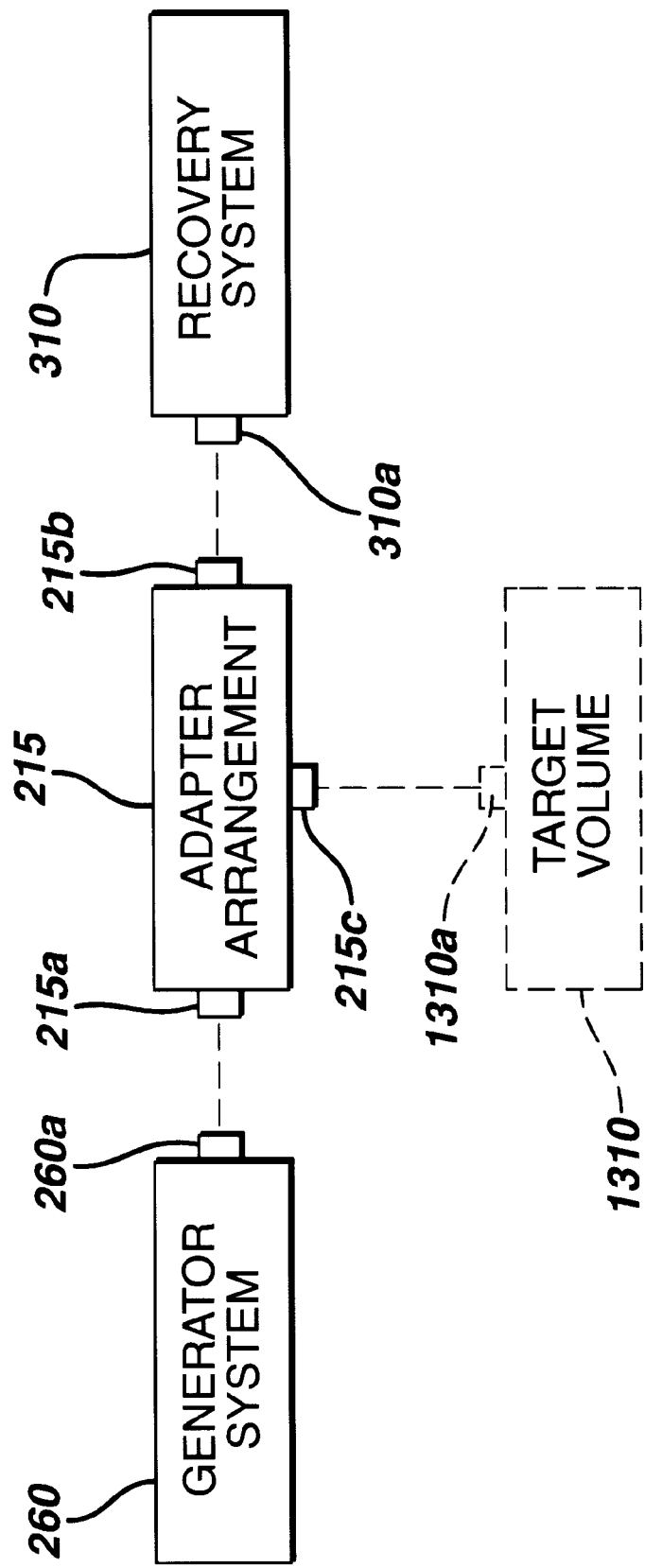
FIG. 7 schematically illustrates a concept of modular, interchangeable and selectively integrable sections.

FIG. 7 schematically illustrates, in accordance with a preferred embodiment of the present invention, a concept of modular, interchangeable and selectively integrable sections. Indicated at 260 is a generator system, which, for example, could correspond to that shown (further ahead) in FIG. 8 containing components relating to the generation of sterilant gas. Section 215, on the other hand, may be considered an "adapter arrangement" and which, for example, could correspond to that section shown (further ahead) in FIG. 8 containing components serving to administer gas from an isolator or other enclosed space, extract it therefrom and either recirculate it or direct it to recovery arrangement 310. Further, recovery system 310 could be embodied as yet another modular section and could, for example, correspond to the corresponding dotted section 310 shown in FIG. 6.

Thus, in this manner, with continued reference to FIG. 7, it will be appreciated that a multi-portioned modular arrangement is contemplated, in which each of the three aforementioned modular components (generator system 260, adapter arrangement 215 and recovery system 310) can be singular, discrete entities that are selectively integrable with one another or with other compatible modular components. For this purpose, each modular component will preferably bear an interface or connection scheme that allows it to be readily integrable with other modular components. Thus, generator system 260 will preferably have an interface or connection scheme 260a that permits facilitated connection with an interface or connection scheme 215a of adapter arrangement 215. Likewise, adapter arrangement 215 will preferably have an interface or connection scheme 215b that permits facilitated connection with an interface or connection scheme 310a of a recovery system 310. Finally, adapter arrangement 215 will preferably have an interface or connection scheme 215c that permits facilitated connection with an interface or connection scheme 1310a of a given target volume 1310 (i.e. a microbial isolator or other enclosed space).

Referring now back to FIG. 6 as a non-restrictive example, it will be appreciated that the interfacing of connection schemes 260a and 215a (see FIG. 7) might occur, for example, at a point between valve 282 and the intersection with cross-line 286. Further, the interfacing of connection schemes 215b and 310a (see FIG. 7) might occur, for example, at a point between valve 306 and junction 314. Connections may be embodied in any suitable manner, such as via conventional pipe couplings (which will preferably be releasable to facilitate selective disconnection and reconnection).

In any event, it will be appreciated that the general arrangement of modular components and connection schemes illustrated in FIG. 7 broadly contemplates a wide range of connection schemes and modularities that can be configured and arranged in essentially any manner deemed suitable. A further general discussion of this concept is provided further below with reference to FIGS. 47 through 51.

Figure 8:
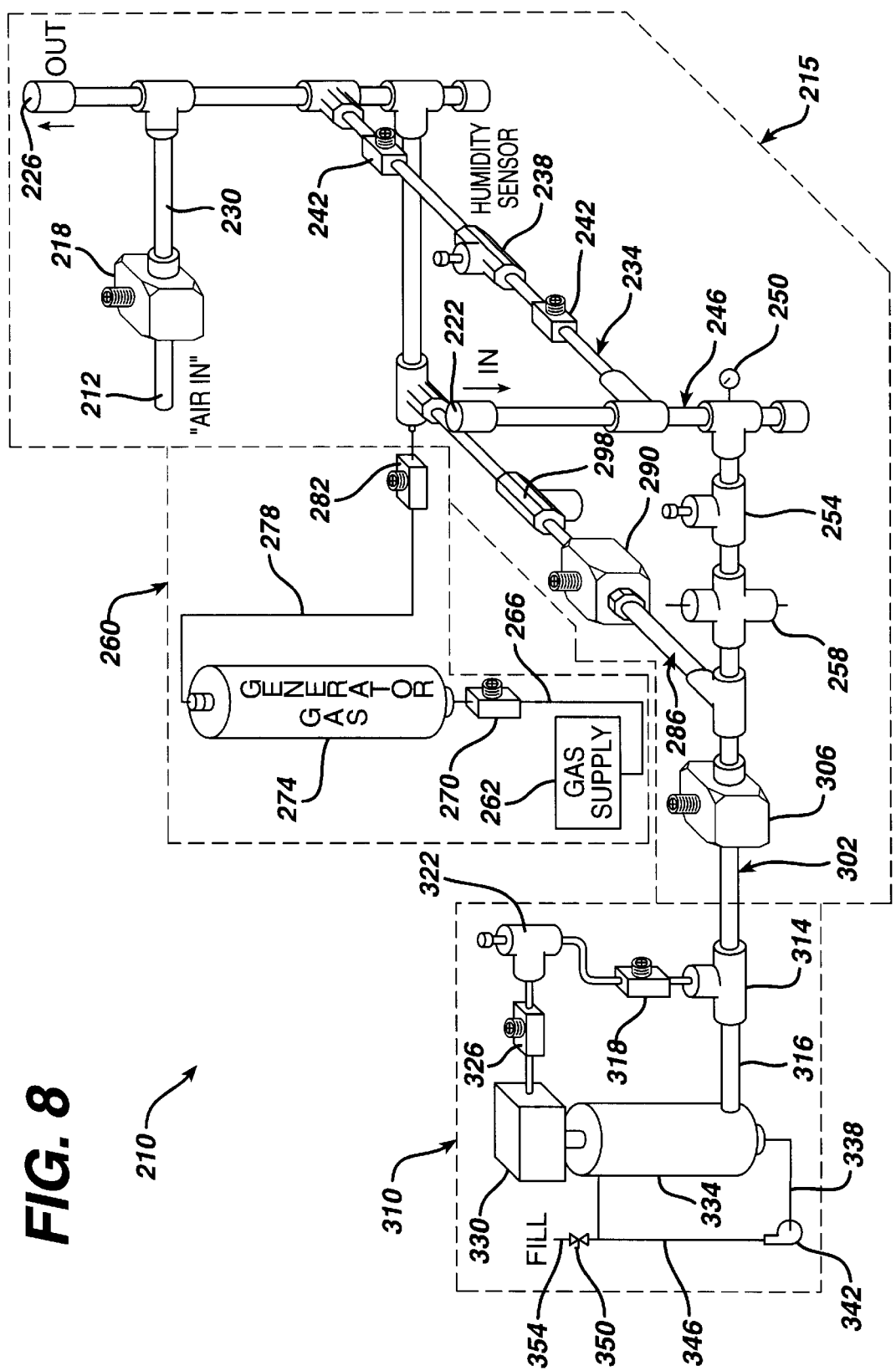
FIG. 8 is essentially the same view as FIG. 6, but also indicating three distinct sections of the system.

It will now be appreciated that, as a non-restrictive example of the "modularity" principle illustrated in FIG. 7, FIG. 8 shows essentially the same system shown in FIG. 6, but also indicates three distinct sections of the system. Thus, in FIG. 8, the dotted section indicated at 215 represents the "adapter" section, the dotted section indicated at 260 represents the "gas generator" section and the dotted section indicated at 310, as already stated, represents the "gas recovery" section. As was discussed hereinabove with relation to FIG. 7, the three sections 215, 260 and 310 shown in FIG. 8, in accordance with a preferred embodiment of the present invention, may be considered as being selectively connectable and de-connectable with respect to one another and interchangeable with other modular sections, to selectively and variably assemble such modular sections in a manner to construct a greater sterilization apparatus 210 with a view to customizing the collectively assembled sterilizing apparatus 210 for use with a particular target volume (e.g. a microbial isolator or other enclosed space).

Accordingly, with reference to either or both of FIGS. 7 and 8, it is to be understood, for example, that a given adapter section 215 may preferably be configured and arranged so as to be able to accommodate a wide range of gas generator sections 260 and/or recovery systems 310. For example, although a chlorine dioxide gas generating system is specifically discussed and illustrated herein, it is conceivable to selectively integrate, with the illustrated adapter section 215, other types of gas generators. Likewise, although specific types of recovery systems 310 are described and illustrated herein, it is conceivable to selectively integrate, with the adapter arrangement 215 illustrated in either or both of FIGS. 7 and 8, a wide range of other types of recovery systems, each conceivably suitable for a corresponding gas generation system 260. In turn, such different permutations of adapter system 215, gas generation system 260 and recovery system 310 may be specifically customized for the particular target volume to which the adapter system 215 is to be connected (i.e., via inlet and outlet portions 222/226).

Figure 9:
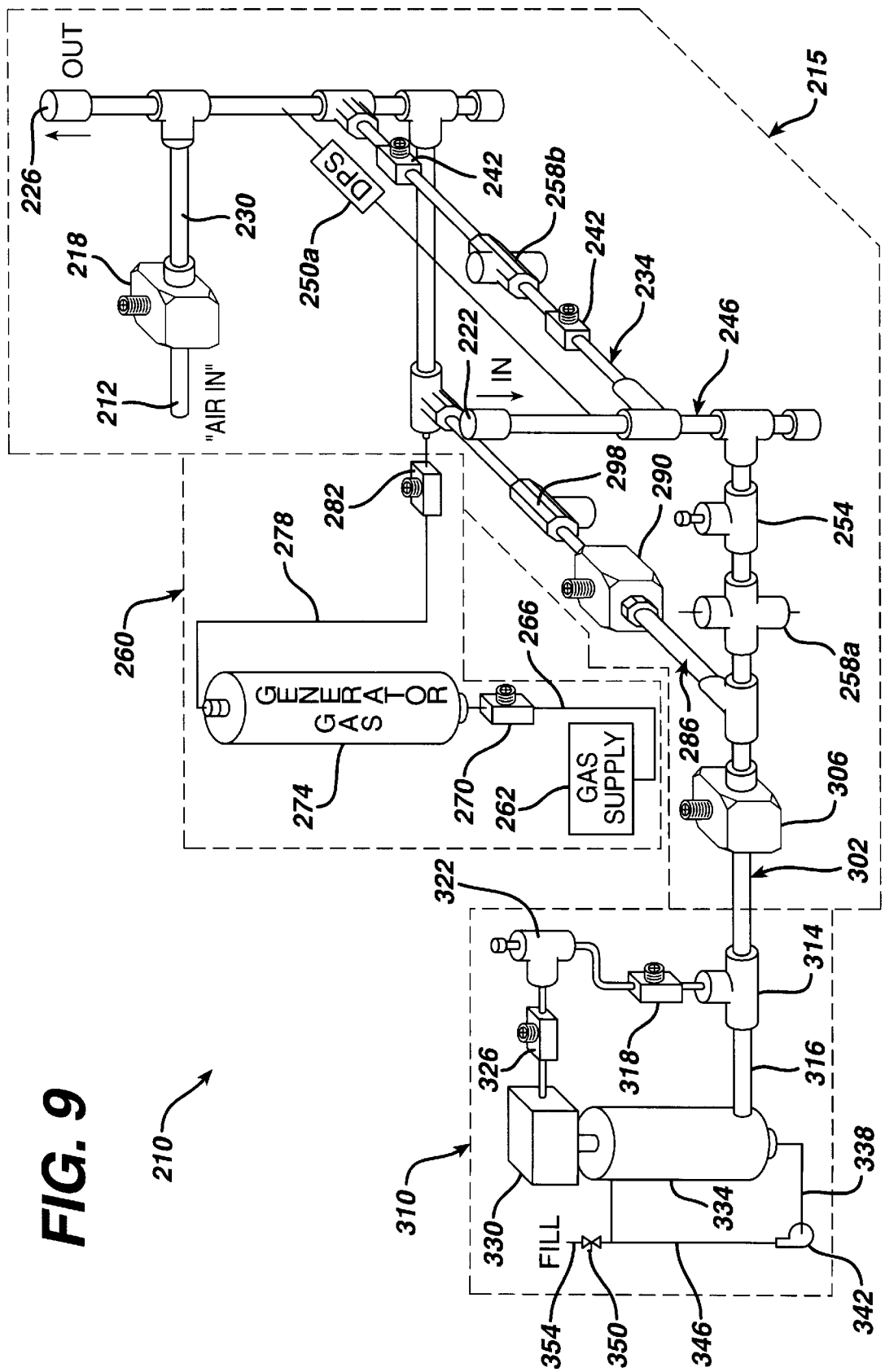
FIG. 9 is essentially the same view as FIG. 8, but showing an alternative arrangement for pressure and humidity sensing.

FIG. 9 illustrates essentially the same view as FIG. 8, but shows adapter section 215 as containing an alternative arrangement for pressure and humidity sensing. Particularly, as shown in FIG. 9, the pressure sensor 250 shown in FIGS. 6 and 8 has been eliminated in favor of a differential pressure sensor 250a, which has lines extending from the sensor itself to both the inlet portion 222 of adapter 215 and the outlet portion 226. Differential pressure sensors per se would appear to be well-known to those of ordinary skill in the art and will be further discussed herein. Preferably, the differential pressure sensor 250a contemplated herein will afford the capability of detecting significant pressure differences between inlet and outlet portions 222 and 226 which could indicate, for example, a leak somewhere in the system or a loose connection between inlet or outlet portion 222 or 226 and corresponding connections of the target volume.

Also shown in FIG. 9 is the use of an optical measuring system 258b in place of the previously illustrated and described humidity sensor 238 (with the original optical sensor 258 now being indicated at 258a). As will be discussed further below with relation to FIGS. 14 and 15, optical sensors 258a and 258b may each be respectively configured for measuring sterilant gas concentration and water concentration within the gas circulating in the sterilizing apparatus 210. For example, sensor 258a will preferably be suitably configured for measuring the concentration of sterilant in the sterilant gas being propagated through the system, while sensor 258b will preferably be suitably configured for configured for measuring to concentration of water (i.e., overall humidity) within the system.

GAS RECOVERY SYSTEM

Figure 10:
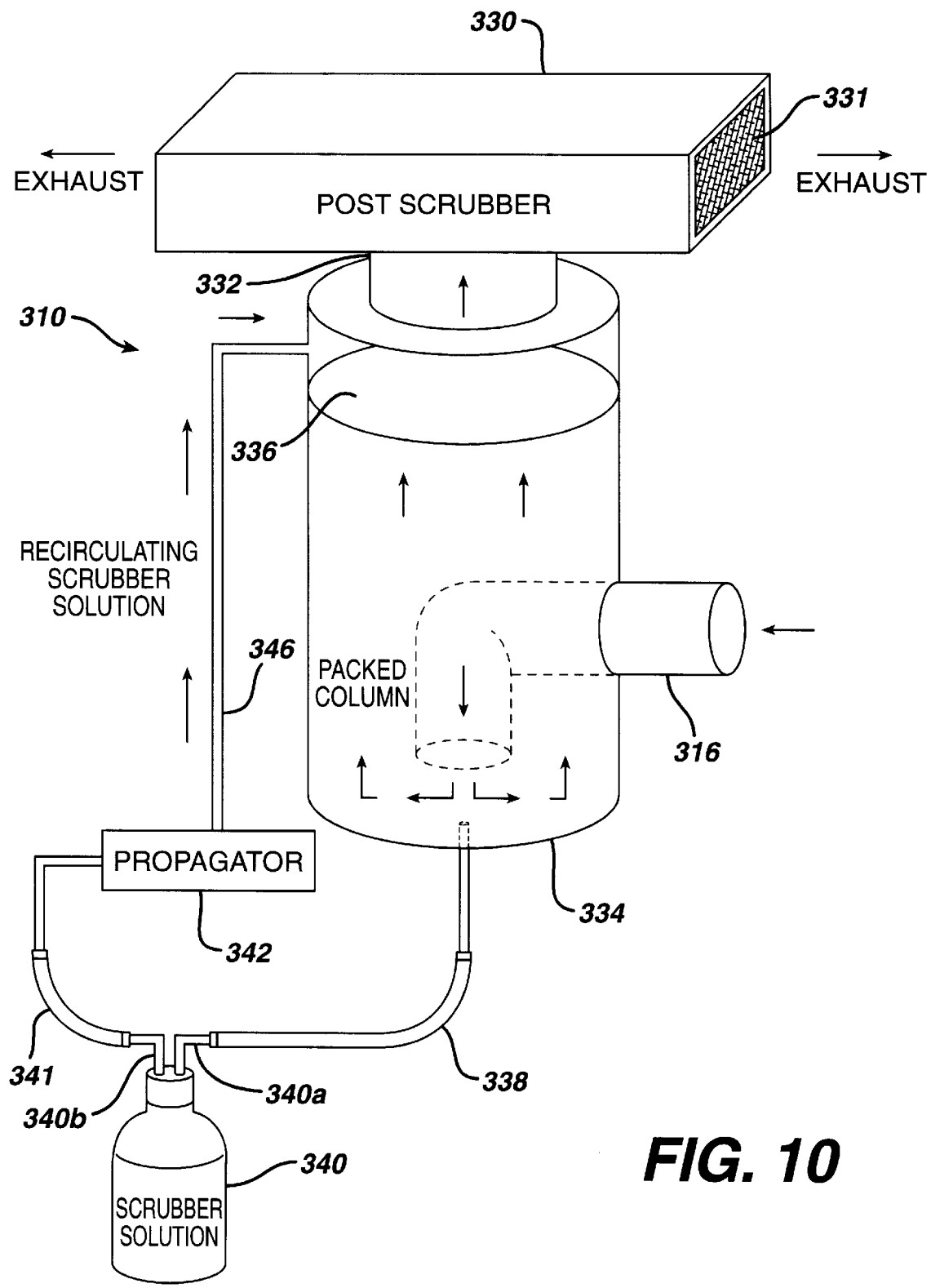
FIG. 10 illustrates a gas-recovery system that may be utilized in accordance with the present invention.

FIG. 10 illustrates a gas-recovery system 310 that may be utilized in accordance with at least one preferred embodiment of the present invention.

First, it is to be understood that a gas-recovery system such as that indicated at 310 in FIG. 10 may, in accordance with at least one preferred embodiment of the present invention, be incorporated into the system illustrated in FIG. 6. In such a context, the purpose of gas recovery system 310 would be to receive, via line 302 (see FIG. 6), a gas mixture that has already been circulated through a microbial isolator and that needs to be exhausted in an environmentally safe manner and/or treated in a manner that facilitates the recovery of one or more ingredients (such as active ingredients). Conceivably, with reference to both FIGS. 6 and 10, the effective inlet into the recovery system 310 could be represented by pipe segment 316.

Turning now to FIG. 10, inlet 316 preferably feeds into the scrubber 334 proper. Inlet 316, in this manner, will preferably penetrate the outer wall of scrubber 334 and, in accordance with at least one preferred embodiment, will bend substantially at a right angle in a downward direction. As indicated by the arrows, the flow of exhaust gas will thus preferably proceed through this inlet portion 316, through the right angle, and into the interior of the scrubber 334 proper.

Preferably, the interior of scrubber 334 will be so configured as to present to the incoming exhaust gas a quantity of scrubber solution for interacting therewith. Such scrubber solutions are well-known to those of ordinary skill in the art and will thus not be further discussed herein. However, it suffices to point out that such scrubber solution will be capable of interacting with the exhaust gas in a manner as to recover process sterilant gas present in the exhaust gas prior to the gas being exhausted to the ambient atmosphere.

Thus, for the purpose of presenting to the incoming exhaust gas an appropriate quantity of scrubber solution such as that just described, preferably disposed within the interior of scrubber 334 is a packed column 336 of rings. The layout and function of such rings will be described in more detail herebelow.

Essentially, it is to be understood that the packing material used in packed column 336 need not necessarily be restricted to rings as discussed herein. Generally, essentially any shape or size (of individual packing components) can be used that afford the presentation of large surface areas for the accumulation of scrubber solution thereon, as well as having a shape that lends itself to facilitated stacking. Further, the packing material should preferably present low resistance to airflow. Thus, although ring-shaped elements have been cited herein as one possibility, it is also possible, for example, to use slightly curved or wavy "ravioli" shapes, or simple prismatic shapes (such as triangular or rectilinear shapes with hollowed centers that permit the accumulation of scrubber solution on inner surfaces).

At the top of scrubber 334, there will preferably be an outlet 332 leading to a post scrubber 330. In accordance with at least one preferred embodiment of the present invention, post scrubber 330 will preferably be a soda-lime post scrubber. Such post-scrubbers would also appear to be well-known to those of ordinary skill in the art and, as such, will not be described in further detail herein. It suffices to point out that a primary function of such a post-scrubber is to recover at least one ingredient from the exhaust gas in question, prior to the gas being exhausted to the ambient atmosphere. In the context of chlorine dioxide gas, for example, the retained ingredient could be an active ingredient such as chloride or chlorite, either of which may subsequently be used for the generation of new sterilant gas.

Post scrubber 330 will preferably include one or more exhaust portions 331 (one of which is shown in FIG. 10), through which exhaust gas or air may flow.

In accordance with at least one preferred embodiment of the present invention, the provision of scrubber solution will preferably take place via an interchangeable supply. Thus, preferably extending from the bottom of scrubber 334 is a line 338 which leads to a suitable container 340 containing scrubber solution, and preferably leading from the container 340 is another line 341 which leads to a pump or other suitable propagator or propulsion arrangement 342. In accordance with at least one preferred embodiment of the present invention, propagator 342 may be a corrosion-resistant pump.

Thus, in accordance with at least one preferred embodiment of the present invention, a recirculation system will preferably be provided with respect to the scrubber solution, in that scrubber solution originating from container 340 will preferably be transported to the top of scrubber 334 via line 346, at which point it is introduced into the interior of scrubber 334. Once so introduced, it will preferably progress downwardly through the interior of scrubber 334 via a "percolating" effect to be described more fully below, and will thus preferably exit from scrubber 334 via the aforementioned line 338. Upon return to container 340, the scrubber solution so circulated can conceivably be utilized again in another, subsequent cycle of providing scrubber solution to the interior of scrubber 334, to an extent (ie. through a number of cycles) predetermined by the operator and/or deemed appropriate for the scrubbing task at hand.

For the purpose of propagating the scrubber solution upwards through lines 341 and 346, it is conceivable to utilize a compressed air source instead of a pump.

Thus, in accordance with a preferred embodiment of the present invention, recirculating scrubber solution may preferably proceed from pump 342 (via another line 346) to an upper or top portion of scrubber 334. In accordance with at least one preferred embodiment of the present invention, line 346 may preferably enter scrubber 334 at a region that is located vertically above packed column 336.

Figure 13:
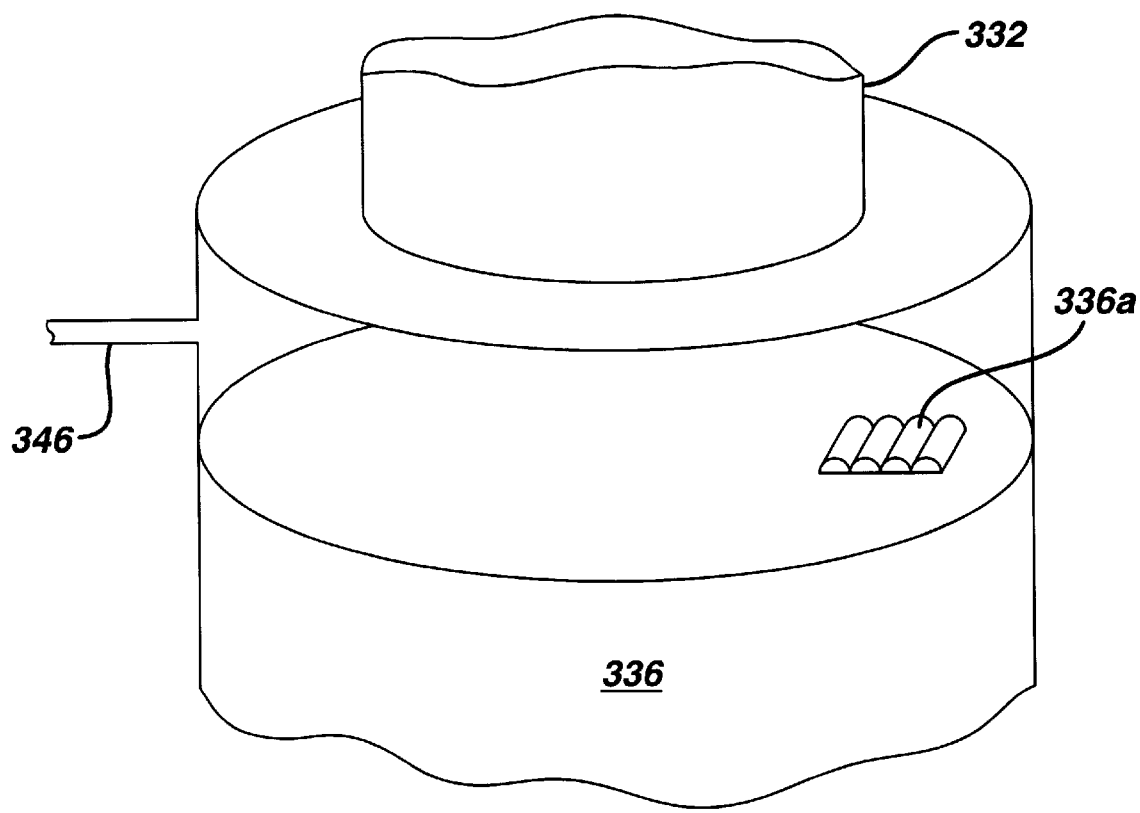
FIG. 13 illustrates a close-up view of a packed column within a recovery system according to the present invention.

As discussed heretofore, the scrubbing solution so introduced into the interior of scrubber 334 will preferably proceed to the bottom of scrubber 334 via a "percolation" effect (i.e. through the intervention of the packing rings 336a discussed herebelow with respect to FIG. 13), it will preferably exit the scrubber 334 via line 338 and be collected in container 340.

The top of container 340 will preferably be equipped with dip tubes 340a and 340b as illustrated in FIG. 10. In this respect, entry tube 340a could be significantly short, so as to facilitate filling of the container 340, while exit tube 340b could be significantly long, so as to facilitate the withdrawal of fluid from container 340. The top will preferably be secured by a quick-disconnect system.

If and when the scrubber solution loses its efficacy (i.e., through repeated use), or if it is simply desired to replace any scrubber solution for other reasons, the container 340, containing spent scrubber solution, can be exchanged for a new container. It is desirable that a cap from the new container be used to secure the contents of the old container to ensure safe handling. In this manner, the cap previously used for the old container, already having dip tubes 340a and 340b disposed therethrough, can readily be placed (e.g. screwed) on the new container.

Post scrubber 330 will preferably filter the exhaust and ensure that entrained droplets do not exit the system. For chlorine dioxide service, it has been found that loosely packed soda lime in the post scrubber will essentially remove any and all traces of the gas.

Figure 11:
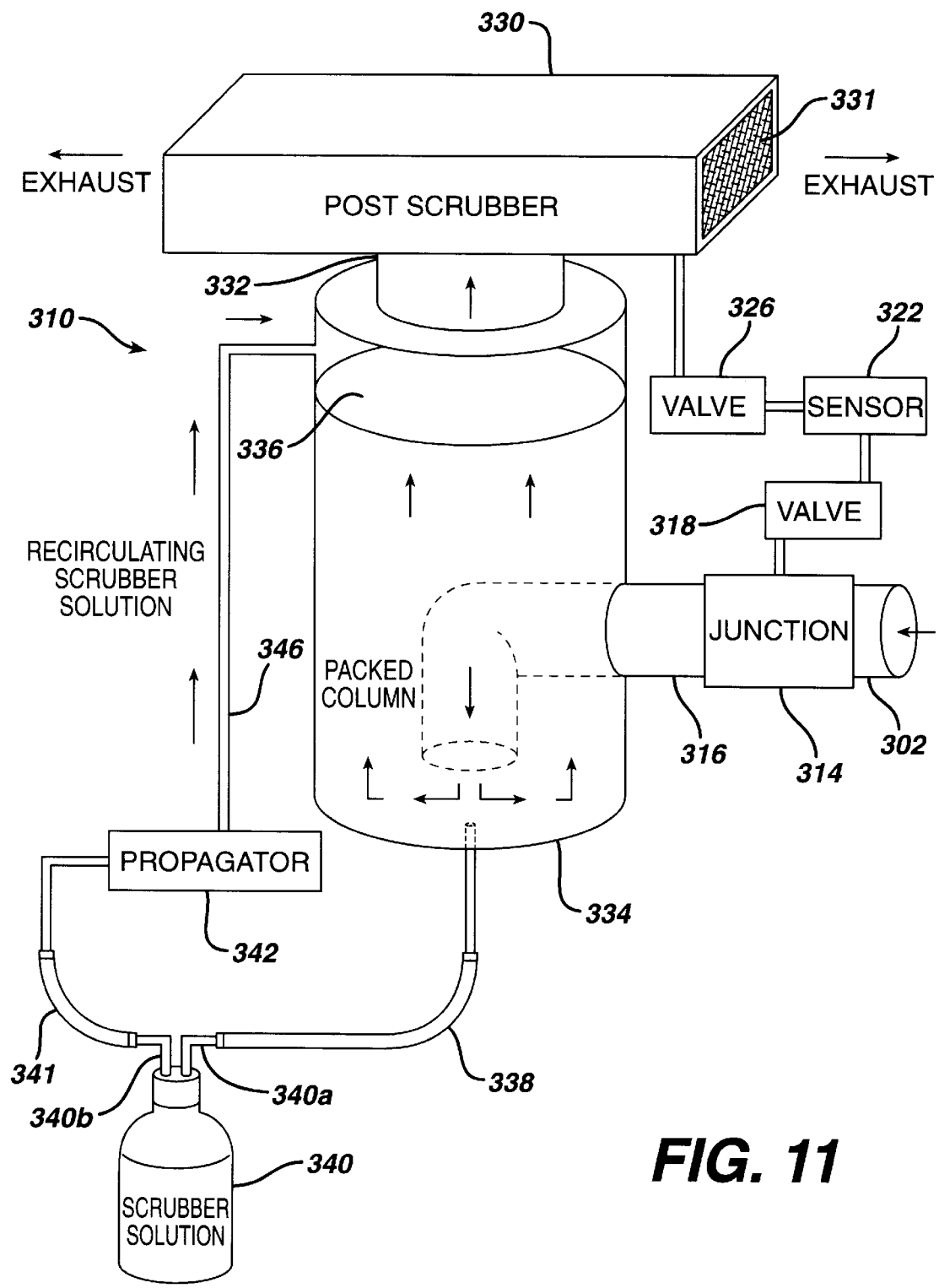
FIG. 11 illustrates an optional arrangement based on the embodiment shown in FIG. 10.

FIG. 11 illustrates an optional arrangement. In accordance with a preferred embodiment of the present invention, the option illustrated in FIG. 11 may be provided if it is desired, for example, to monitor the content of chlorine dioxide (or other substance) that is being exhausted to the ambient atmosphere.

The opening of valves 318 and 326 will permit a suitable amount of effluent to bleed away from junction 314 so as to be measured by a suitable sensor 322. Conceivably, such a sensor 322 could be embodied by an optical gas measurement system of the type to be described herebelow with references to FIGS. 14 and/or 15. In one scenario, if sensor 322 detects a significantly low level of chlorine dioxide (i.e., lower than a predetermined boundary level), it is conceivable for a prompt to then be sent to a control arrangement (see FIG. 46, for example) that will have the effect of subsequently bypassing all effluent to a vent while circumventing the recovery arrangement 310. Alternatively, if the measured chlorine dioxide concentration is unacceptably high, the exhaust of any chlorine dioxide gas into the ambient atmosphere could be prevented.

Preferably, valves 326 and 318 will be shut when it is desired not to undertake measurements via sensor 322; in this manner, the sensor 322 can be protected from extreme levels of chlorine dioxide, which would otherwise compromise the effectiveness of the sensor 322 and, among other things, require the sensor 322 to "recover" after a prolonged period of time.

As another example, if, at startup, the level of chlorine dioxide (or other substance) in the potential effluent initially is above a predetermined level, it is conceivable to permit the effluent to progress through the recovery system 310 until such a time that sensor 322 indicates that the chlorine dioxide content (or content of another predetermined substance) has been reduced below an accepted threshold.

Figure 12:
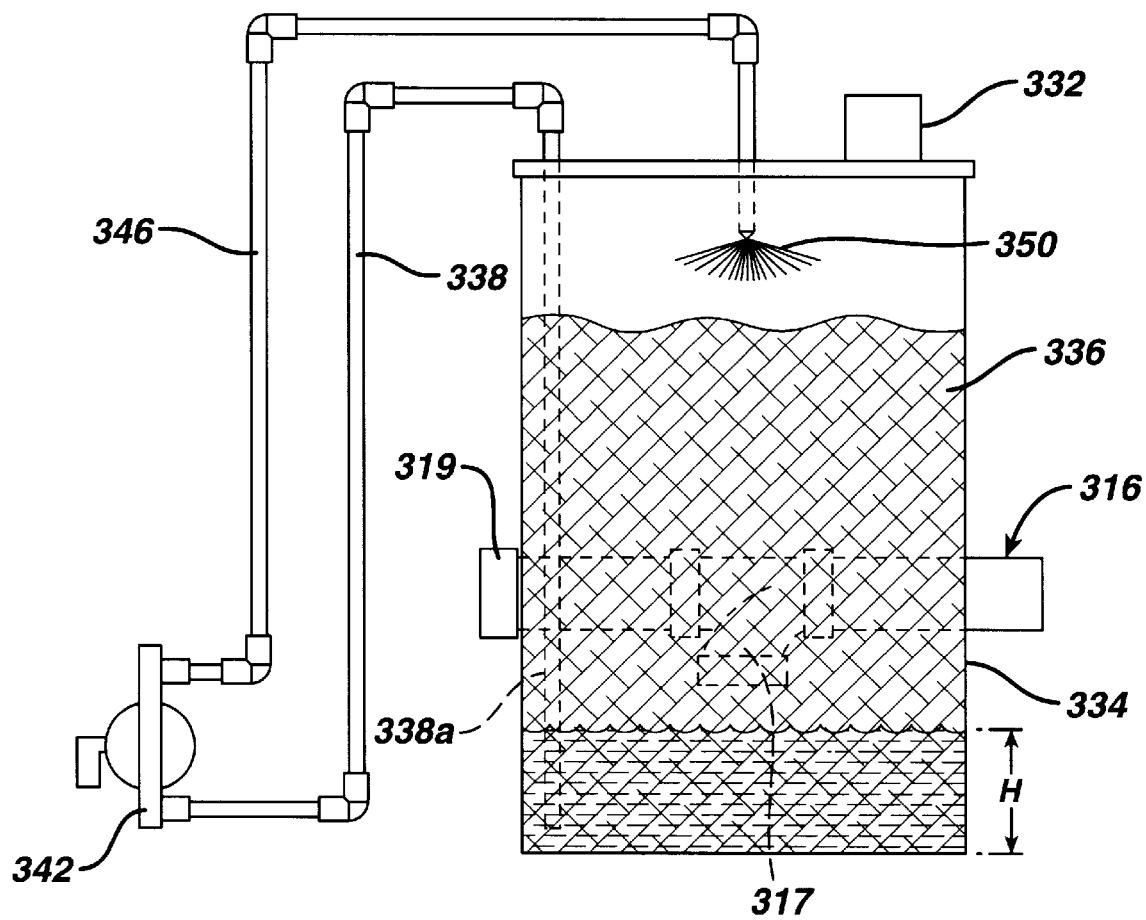
FIG. 12 illustrates an alternative recovery arrangement in accordance with a preferred embodiment of the present invention.

FIG. 12 illustrates an alternative recovery arrangement 310 in accordance with a preferred embodiment of the present invention. The alternative arrangement 310 illustrated in FIG. 12 is representative of a more "completely" disposable arrangement. Whereas, in the arrangement illustrated in FIG. 10, an interchangeable container of scrubber solution is provided, the arrangement illustrated in FIG. 12 involves the wholesale exchange of scrubber tank 334 (with attendant scrubber solution and packing material 336) with another scrubber tank when deemed necessary.

As shown in FIG. 12, a branch 317 may extend, via a right-angle "tee", away from inlet 316 and vertically downwardly into the scrubber tank 334 proper, preferably parallel to the central longitudinal axis of the tank. Further, a capped extension 319 may also branch off from inlet 316. Preferably, a recirculating pump 342 may be provided for recirculating scrubber solution. Further, inlet line 338 may lead from the bottom of the scrubber tank 334, direct liquid upwards, and thence down to pump 342. Conduit 346 may preferably lead away from recirculating pump 342 into a spray head 350 at the top of tank 334.

In accordance with a preferred embodiment of the present invention, the embodiment shown in FIG. 12 will permit the maintenance of a limited reservoir of scrubber solution, having a height H at the bottom of packing column 336. Preferably, a distance will be maintained between the reservoir height H and the mouth of inlet 317.

As described heretofore, the packing rings in column 336 will each preferably be covered by some of the scrubber solution that has emanated from spray head 350. However, it is possible to maintain a limited reservoir height H at the bottom of scrubber tank 334 as long as the mouth of inlet 317 is not met by the reservoir height H.

In accordance with a preferred embodiment of the present invention, pump inlet line 338 may recirculate scrubber solution from the bottom of tank 334 by way of extension 338a. Extension 338a, as shown, can preferably extend nearly all the way to the bottom of tank 334 and, in this manner, withdraw scrubber liquid upwardly to the top of the tank 334 and then over to pump 342.

In accordance with at least one preferred embodiment of the present invention, packing rings 336a (see FIG. 13) may be made of polypropylene, may be cylindrical in shape and may have a diameter of ⅝". With such dimensions for the packing rings 336a, tank 334 may have a vertical dimension, top to bottom (with the exclusion of exhaust 332), of about 22.63 inches and a diameter of 14.00 inches. Of course, these dimensions are provided merely as examples but, in the context of the present invention, have been found as being particularly effective for the purpose of enabling the effective cleaning, recovery and/or exhaust of gas, infused with chlorine dioxide, that has circulated through a sterilizing apparatus and attached enclosed space. Although it is conceivable to use to utilize dimensions (for each of the three aforementioned parameters) that are different from the dimensions cited above but similar in scope, it will be appreciated that the specific dimensions just mentioned (or dimensions in the neighborhood thereof) afford an economy of size, in the context of a scrubbing apparatus, that might not have previously been realizable.

Other referenced components shown in FIG. 12, whether or not described hereinabove, can be considered as being substantially similar to similarly numbered components in FIG. 10.

FIG. 13 illustrates a close-up view of a packed column 336 in accordance with an embodiment of the present invention Preferably, packed column 336 will include a significant quantity of individual packings 336a (only a few of which are shown for the sake of simplicity). The individual packings 336a will each preferably be wetted with the scrubber solution from container 340 (see FIG. 10). In this manner, the exhaust path will not pass exclusively through liquid, but will encounter liquid scrubber solution only insofar as the solution is present on the surfaces of packings 336a. Preferably, the packings 336a will be so configured and dimensioned as to provide, in sum, an optimal composite surface area for bearing the liquid scrubber solution thereon and presenting the same to the exhaust flow.

Thus, the scrubber solution will preferably be circulated by a propagator 342 (as shown in FIG. 10), thence to flow to the top of the scrubber 334 (as shown in FIG. 10) and subsequently be sprayed over the packings 336a. The spraying may preferably be accomplished by any suitable port arrangement serving to introduce scrubber solution into the interior of scrubber 334; a single spray port is conceivable, as is a plurality of such ports distributed about the periphery of scrubber 334 in any desired manner.

It is to be understood that, within the scope of the present invention, it is possible to utilize an arrangement or arrangements, other than the packing materials described heretofore (a non-restrictive example of which is shown in FIG. 13), to afford the capability of enabling gas to be passed over tortuous surface material and simultaneously contacting the tortuous surface material with an interacting medium to minimize the volume of interacting medium required. As non-restrictive examples, such interacting medium could be embodied by the scrubber solution described heretofore. Further, the tortuous surface material could embodied by another type of packing arrangement, such as a singular net or mesh capable of retaining an interacting medium, such as scrubber solution, thereon, or could be embodied by types of plural packing materials such as those described heretofore.

OPTICAL GAS MEASUREMENT SYSTEM

Figure 14:
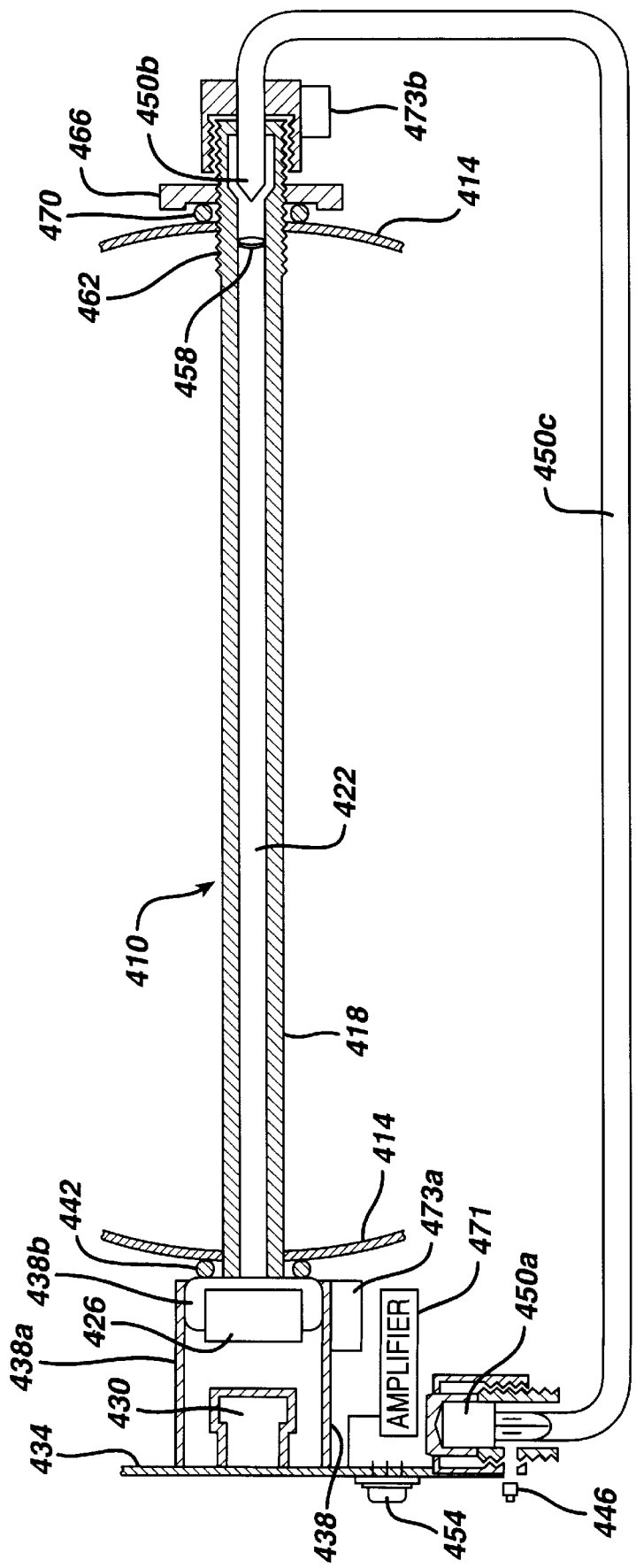
FIG. 14 is a cross-sectional and longitudinal view of an optical gas measurement system.

FIG. 14 illustrates a wide-range optical gas measurement system 410 that may be utilized in accordance with at least one preferred embodiment of the present invention.

As briefly stated heretofore, non-restrictive examples of appropriate locations for such a system might be: in the vicinity of the cross flow cell 258 illustrated in FIG. 6; at the locations indicated at 258a and 258b in FIG. 9; or at the location indicated at 322 in FIGS. 6 and 11. However, as discussed below, other locations are feasible. Further, this optical gas measurement system could conceivably find applications in contexts outside of the sterilization sciences.

A large diameter pipe (such as that which may be employed in the gas generating system 210 shown in FIG. 6) is indicated at 414 in FIG. 14. Generally, the measurement system may be primarily comprised by a tube 418 that spans the diameter of pipe 414. Preferably the tube 418 has a slot 422 to permit the flow of gas flow transversely through tube 418 and into the optical path of the radiation arrangement described herebelow.

Preferably, on one side of the pipe 414, tube 418 may terminate at an interference filter 426. Preferably disposed adjacent filter 426 is an ultraviolet photoreceptor 430. Preferably, photoreceptor 430 may be mounted on a "preamp card" 434 or other suitable mounting board. Further, interference filter 426 may also be mounted with respect to this card via a suitable support element or elements 438a/b. In accordance with a presently preferred embodiment of the present invention, such support elements can be constituted by an annular sleeve 438a extending from card 434, and a disc-shaped holder 438b for filter 426.

For physical protection and sealing purposes, an o-ring 442 or the like may be provided between filter 426 and the outer surface of pipe 414. In accordance with a presently preferred embodiment of the present invention, the aforementioned photoreceptor 430 may be embodied by a phototransistor.

At the same side of pipe 414, there may preferably be provided a photoreceptor 446 in the vicinity of card 434, as well as a radiation arrangement collectively indicated at 450a–c. Photoreceptor 446 will preferably be embodied by a suitable photodiode, photoresistor, phototransistor or the like. In accordance with a presently preferred embodiment of the present invention, photoreceptor 446 may be embodied by a small photodiode.

Preferably in communication with the radiation arrangement 450a–c is an intensity-dependent lamp power supply 454 (which itself is mounted on preamp card 434). A suitable fiber optic cable 450c preferably connects radiation source 450a (which could be embodied, for example, by a suitable lamp) with emitter 450b (which could be embodied, for example, by a suitably shaped and configured end of the fiberoptic cable 450c). At this portion of the device, i.e., that portion disposed in the vicinity of that portion of the outer wall of pipe 414 located toward the right-hand side of FIG. 14, there are external threads 462. Preferably mating with the external threads is a sealing threaded disk 466 and, similarly to the other side, there may preferably be an o-ring 470.

As stated briefly heretofore, it is conceivable to position a gas measurement system 410 (such as that illustrated in FIG. 14 or that illustrated in FIG. 15) at essentially any point of a gas generating system (such as that illustrated in FIG. 6) deemed suitable.

It will be appreciated that, by mounting radiation source 450a in the same general vicinity as power supply 454 and photoreceptor 430, essentially all components are immediately accessible and the need for providing a second mounting medium (e.g. another card or board) is precluded.

Preferably, radiation arrangement 450a–c will be embodied by components that are appropriate to the absorption spectrum of the gas to be quantified. In the case of ultraviolet measurements, in the context of measuring chlorine dioxide concentration, a quartz-halogen lamp may be used (similar to those used in microscopy) as radiation source 450a, since these have been found to be particularly rich in UV radiation and are available in pre-focused bulbs.

In accordance with a preferred embodiment of the present invention, filter 426 will preferably be mounted so that it can removed. In such a context, it is possible to afford the interchangeability of filters, so that the overall measurement apparatus can be customized for different contexts. For example, although it is desirable, in the context of chlorine dioxide measurement, to utilize a filter 426 that propagates light that will be in the UV range, it will be appreciated that the measurement of other gases may require filters that propagate light in the infrared range. In one embodiment of the present invention, it is even possible to use the illustrated measurement apparatus to measure humidity (a more detailed example of which will be described further below), in which case the filter 426 could be configured to propagate light that is in the absorption spectrum of water. For example, infrared wavelengths would appear to be compatible with measuring water concentration (i.e., measuring humidity). Thus, filter 426 could be configured to propagate wavelengths in the neighborhood of about 360 nm in the case of measuring chlorine dioxide concentrations or about 1800 nm in the case of measuring water concentrations.

Although standard interference filters will normally suffice for use as filter 426, it is conceivable to utilize essentially any suitable equivalent, such as a diffraction grating.

A standard voltage regulator 454 will preferably provide a stabilized voltage supply to the radiation source 450a. A small photoreceptor 446, preferably mounted adjacent to radiation source 450a, can be provided to monitor the actual intensity of the radiation source 450a. The intensity so monitored is input to the voltage regulator 454, which in turn will provided a correcting feedback to radiation source 450a for the purpose of maintaining a constant intensity of radiation source 450a. Such feedback can also be used to self-zero the system (i.e., zero the system without operator intervention).

Thus, it will be appreciated that, in contrast with conventional optical measuring devices, which function on the principle of stabilized voltage input to a radiation source, the present invention, in accordance with at least one presently preferred embodiment, provides a virtually constant intensity of radiation source 450a during a given period of operation, which in turn yields several advantages. For one, consistent radiation intensity will lead to more accurate measurements. Furthermore, the lack of occasional "surges" in radiation intensity (as may be experienced in the context of a radiation source with fluctuating intensity), will result in longer service life for the radiation source 450a in question.

A further advantage will be appreciated in that it is possible, at the start of the service life of a radiation source 450a, to utilize a lower voltage than might otherwise be used in the context of conventional arrangements. As a result, it will be appreciated that the lower voltage will "stretch" the useful radiation spectrum of the radiation source, rather than concentrating the useful radiation spectrum in a limited range of wavelengths. Furthermore, as long-term deterioration of the radiation source 450a is experienced, it is only necessary that the voltage applied to radiation source 450a be gradually increased over time in order to maintain the desired intensity.

Preferably, voltage regulator 454 and photoreceptor 446 will be appropriately calibrated so as to operate in the manner described. This will preferably result in a constant "zero value" in the presence of a clear optical path. In addition, simple programming software can provide compensation for physical occlusion of the optical path.

Board 434 is preferably a shielded printed circuit board. Filter 426 will preferably be appropriate for to the gas being measured (as discussed above). Preferably, filter 426 should pass enough of the active spectrum to maximize the signal but eliminate inactive wavelengths, so as to improve the signal-to-noise ratio. For use as photoreceptor or phototransistor 430, a number of photodiodes and phototransistors are commercially available which span a broad spectrum, such as from about 190 to about 2000 nanometers. It also highly desirable to use a low-noise pre-amplifier 471, which could drive an output with calibrating facilities, such as an output of up to 10 volts. It may be desirable to provide resistive heaters 473 a/b in the vicinity of various optical components, in order to maintain the optical components at temperatures adequate to prevent condensation.

As shown in FIG. 14, there may preferably be a lens 458, such as a quartz lens, interposed between emitter 450b and the rest of passage 422. In accordance with a presently preferred embodiment of the present invention, this may be either a specially designed lens for the designated purpose of collecting any divergent rays from emitter 450b and concentrating them into a substantially straight path through slot 422 or a simple blank that does not significantly affect the path of the rays and merely serves as a "block" in the passage for protecting the emitter against the intrusion of any matter from within pipe 414 that might otherwise sully the emitter 450b and reduce its efficacy. Since, in accordance with a presently preferred embodiment of the present invention, the apparatus 410 shown in FIG. 14 may advantageously be used for the detection of high levels of a given component in pipe 414, the tube 418 will not need to be significantly long, thus diminishing the need for a lens at location 458 that concentrates divergent rays (and thus warranting no more than the use of a "blank" as just described). However, in the case of a significantly long tube, the former (i.e. a lens that concentrates divergent rays) would likely be preferable.

Figure 15:
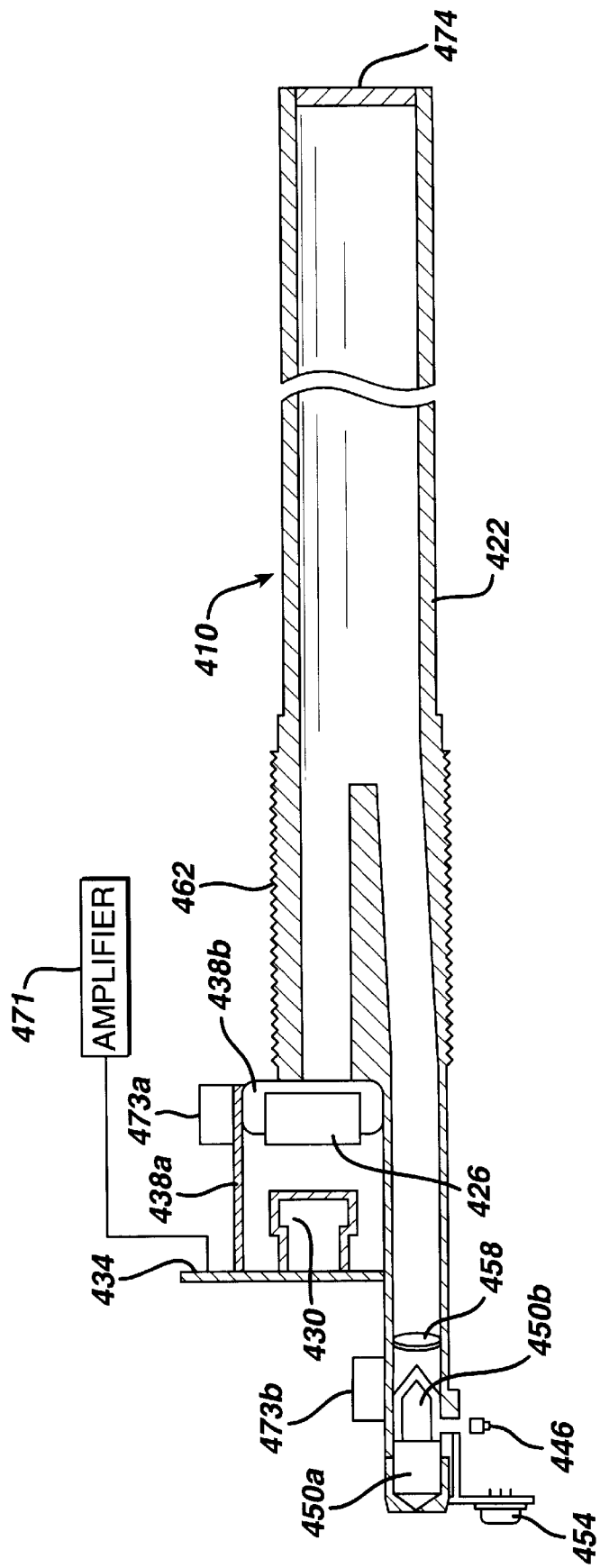
FIG. 15 illustrates, also in longitudinal cross-section, an alternative embodiment of an optical gas measurement system.

FIG. 15 illustrates an alternative embodiment, in which the system 410 is mounted essentially only at one side of a pipe (not shown). In this case, essentially all of the components discussed heretofore with regard to the system 410 may be provided solely at one side of the pipe. Similar components are designated with similar reference numbers.

Preferably, a radiation arrangement, collectively indicated at 450a and 450b, may include, similarly to the embodiment of FIG. 14, a suitable radiation source 450a and a suitable emitter 450b (such as a bulb). However, in the embodiment illustrated in FIG. 15, it will be appreciated that these two components may essentially be substantially directly adjacent one another, thus precluding the need for an arrangement such as the fiberoptic cable 450c shown in FIG. 14. Preferably, with the respect to the embodiment shown in FIG. 15, tube 422 may be suitably perforated or otherwise suitably provided with apertures and/or holes so as to permit the flow of gas therethrough, at least in a manner to permit a sufficient quantity of gas to be intercepted by the path of emitted radiation from radiation source/emitter 450a/b (including the return path reflected from a mirror 474 as described herebelow) for the purposes of measurement described herein.

External threads 462 may preferably be provided in a manner similar to those illustrated in FIG. 14. However, tube 422 will preferably not be as long (or proportionately long) as that illustrated in FIG. 14; rather, it will preferably terminate at a suitably positioned mirror 474 or other suitable reflecting medium. Thus, instead of positioning transmission and receiving components at opposite sides of the pipe in question, it is conceivable to undertake gas measurements while still locating all components at essentially one side of the pipe in question so that the transmitted light will be reflected back via mirror 474, to the receiving components 426 and 430. Emitter 450b will preferably be "aimed" at mirror 474 in a manner so as to facilitate accurate transmission of the concentrated radiation output from radiation source 450a to filter 426. Alternatively, the mirror 474 itself may be suitably angled to fulfill this purpose.

As shown in FIG. 15, there may preferably be a lens 458 similar to that described and illustrated with respect to FIG. 14. As in the case of FIG. 14, the length of the apparatus 410 will likely determine whether a lens capable of concentrating divergent rays is required at location 458 or whether a "blank" would suffice.

Although the embodiments of an optical gas measurement system 410, as illustrated in FIGS. 14 and 15, have been described and illustrated primarily with respect to a gas generating system such as that described and illustrated herein, it is conceivable to utilize them in environments or contexts different from gas generating systems or from the purely physical environments described herein. Particularly, it can serve as a broad-range measurement system for measuring component levels of essentially any optically active fluid.

Consequently, it is conceivable to utilize the arrangement illustrated in FIG. 15 in an environment in which, for example, the apparatus 410 extends through a wall, so as, for example, to measure the concentration of a given component of air or other gas in a room. It is also conceivable for the arrangements illustrated in FIGS. 14 and 15 to be used to measure components in a liquid (such as a liquid circulating through a pipe system) instead of a gas. Additionally, it will be appreciated that the measurement systems contemplated herein are capable not only of measuring the concentration of a given component in a fluid (i.e. gas or liquid) that is moving but also in a fluid that is static.

It will be appreciated that the measurement systems contemplated herein exhibit a unique duality found to be lacking in conventional measurement systems. Particularly, on one hand, the capability of continuous self-correcting feedback ensures that the radiation source 450a in question will emit at a constant or substantially constant intensity, thus avoiding occasional surges of intensity that might otherwise reduce the service of life of the radiation source 450a or occasional deficiencies of intensity that might otherwise hamper the accuracy of measurements. Furthermore, however, the self-correcting feedback apparatus also affords the capability of self-zeroing (or even of establishing the radiation source at a given predetermined non-zero intensity) prior to initiation of a new operation. No operator inputs are required to zero the system. In contrast, conventional devices have not typically distinguished between the continual monitoring and feedback of radiation source intensity that takes place during a given operation and the long-term adjustments that may need to be made from time to time in order to compensate for deterioration of the radiation source.

From the foregoing, it will be appreciated that a system contemplated in accordance with at least one preferred embodiment of the present invention provides a fixed intensity and is also self-zeroing, therefore insuring that no operator intervention is necessary (as opposed to arrangements in which an operator needs to periodically be extensively involved in zeroing the device). Further, the solid state technology contemplated herein, for use as the optical components and measuring components, can serve to reduce the number and extent of the parts used, thus contributing to reduced manufacturing costs.

SEAL-LESS OR STEM-LESS CONTROL DEVICE

The disclosure now turns to examples of valve arrangements that may be utilized in accordance with at least one embodiment of the present invention. The valve arrangements described and illustrated herebelow with reference to FIGS. 16 through 33 could, in accordance with at least one embodiment, be positioned in the gas generating system illustrated in FIG. 6 at the locations of valves 218, 290 and 306, among others.

Figure 16:
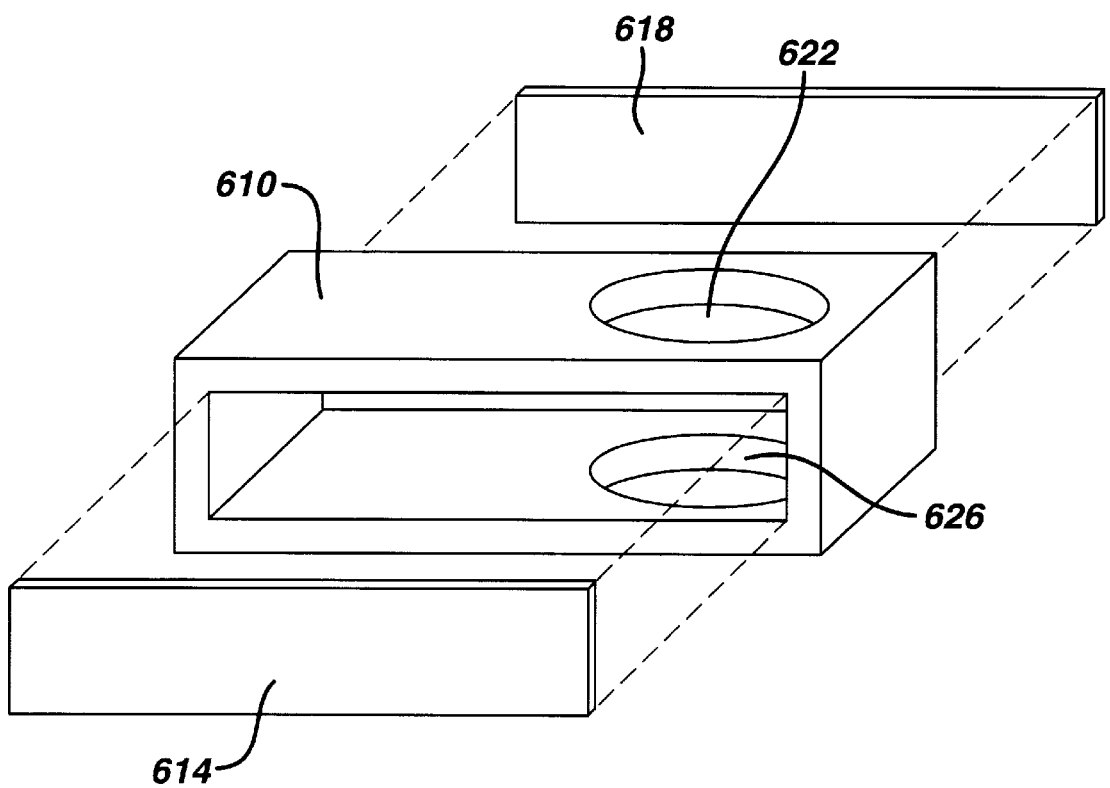
FIG. 16 illustrates, in perspective view, the general construction of a valve body according to an embodiment of the present invention.

FIG. 16 illustrates a general construction of a valve body. Preferably provided are: an extruded body 610, side panels 614 and 618, and holes 622 and 626 preferably being disposed in body 610. Preferably, holes 622 and 626 are provided so as to permit the through-flow of fluid when the valve is open.

Figure 17:
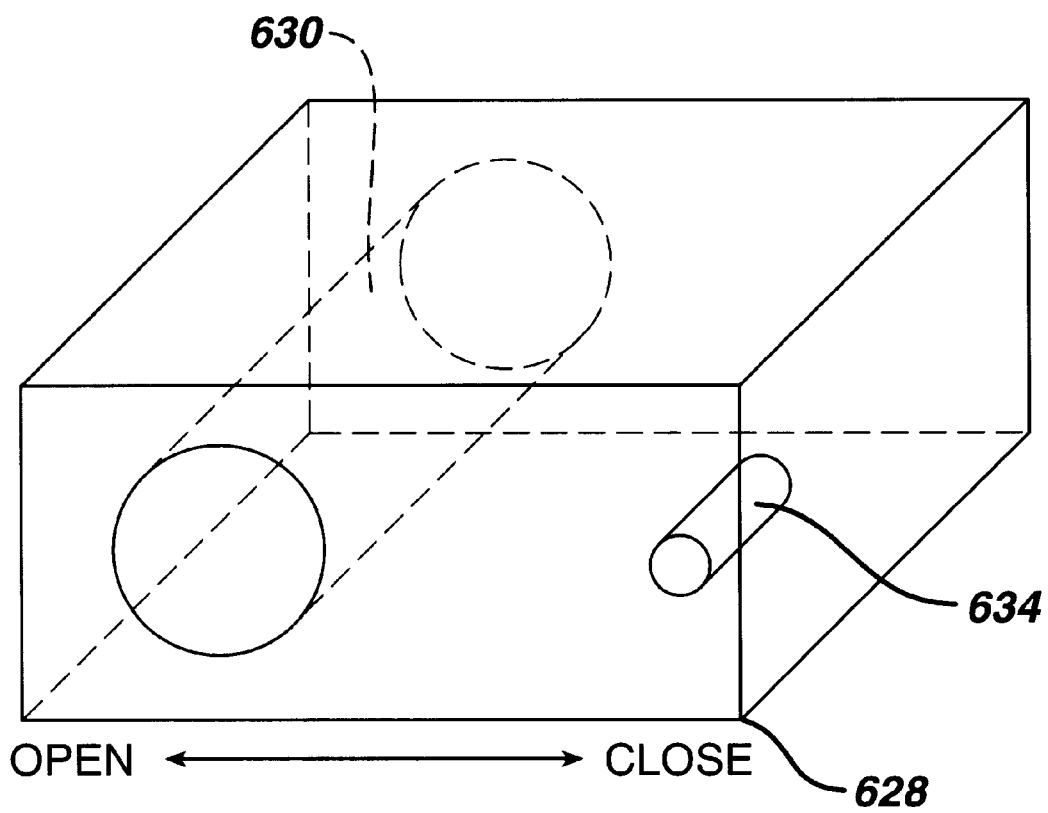
FIG. 17 illustrates a driven element for use with the valve body shown in FIG. 16.

FIG. 17 illustrates a driven element according to an embodiment of the present invention. As shown, a greater block of material 628 may have embedded therewithin a magnetic armature 630 and a smaller permanent magnet 634. This block 628 will preferably sit within the body 610 illustrated in FIG. 16.

In a manner to be described more fully below, magnetic armature 630 will preferably serve to drive block 628 in either an opening direction or a closing direction (as indicated by the arrows) in response to the alternate activation of magnetic coils.

Figure 18:
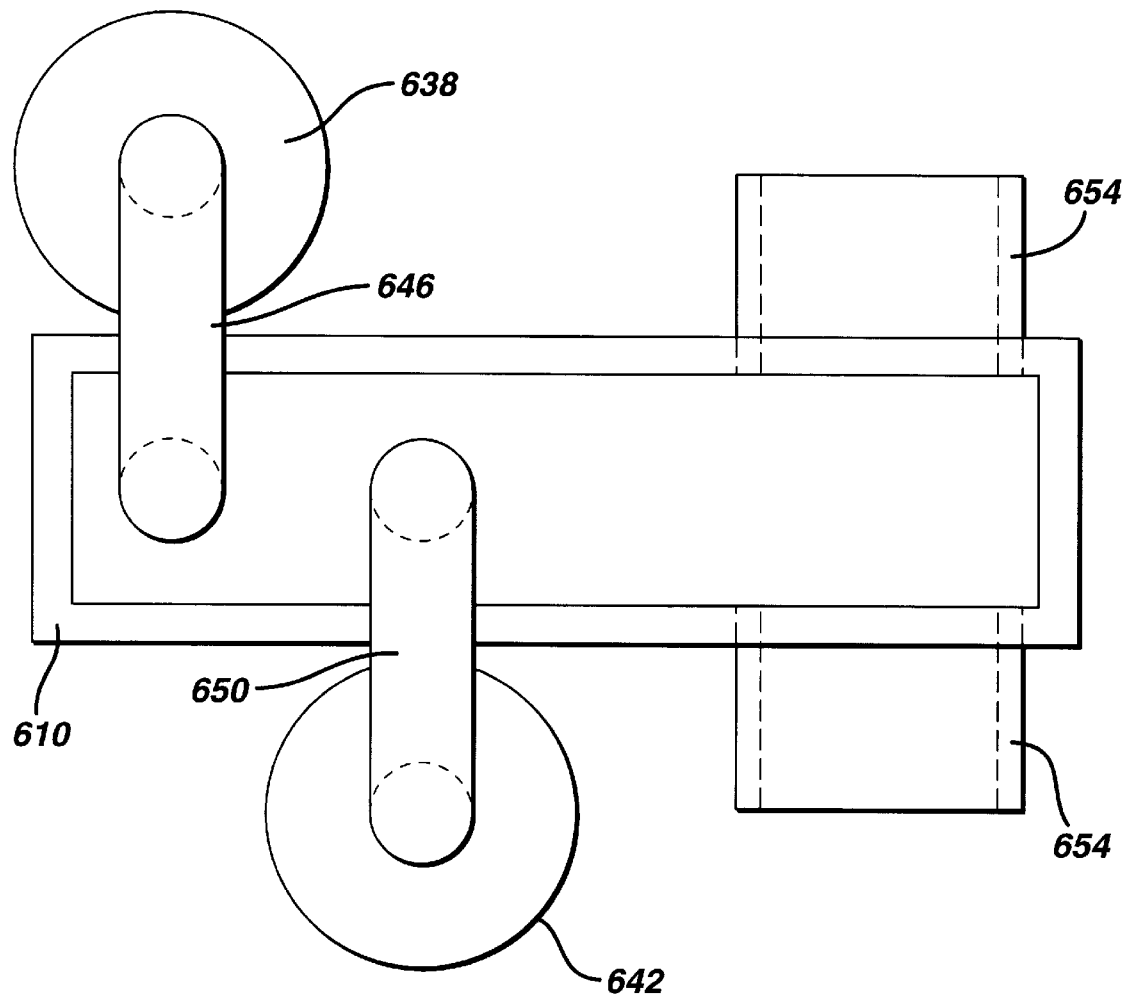
FIG. 18 is an elevational view of a complete valve according to an embodiment of the present invention.

FIG. 18 illustrates the exterior of a complete seal-less valve according to an embodiment of the present invention, with valve body 610 and fluid connectors 654. Connectors 654 will preferably be so configured and arranged as to engage in fluid communication with tubes or pipes in a sterilizing apparatus (e.g. at the locations of valves 218, 290 and 306 illustrated in FIG. 6). Further, connectors 654 will each respectively open into holes 622 and 626 of valve body 610 (see FIG. 16), so as to afford the throughflow of fluid through valve body 610 when the driven element disposed therewithin (such as the one illustrated in FIG. 17) is held in the "open" position. Also illustrated are "open" coil 638 and "close" coil 642, each operable in a manner to be described more fully below. Preferably, magnetic core portions 646, 650 extend from each of the coils 638, 642. In a manner to be appreciated more fully herebelow, the center-line spacing of the coils 638, 642 will essentially determine the length of travel of the driven element disposed within valve body 610.

Figure 19:
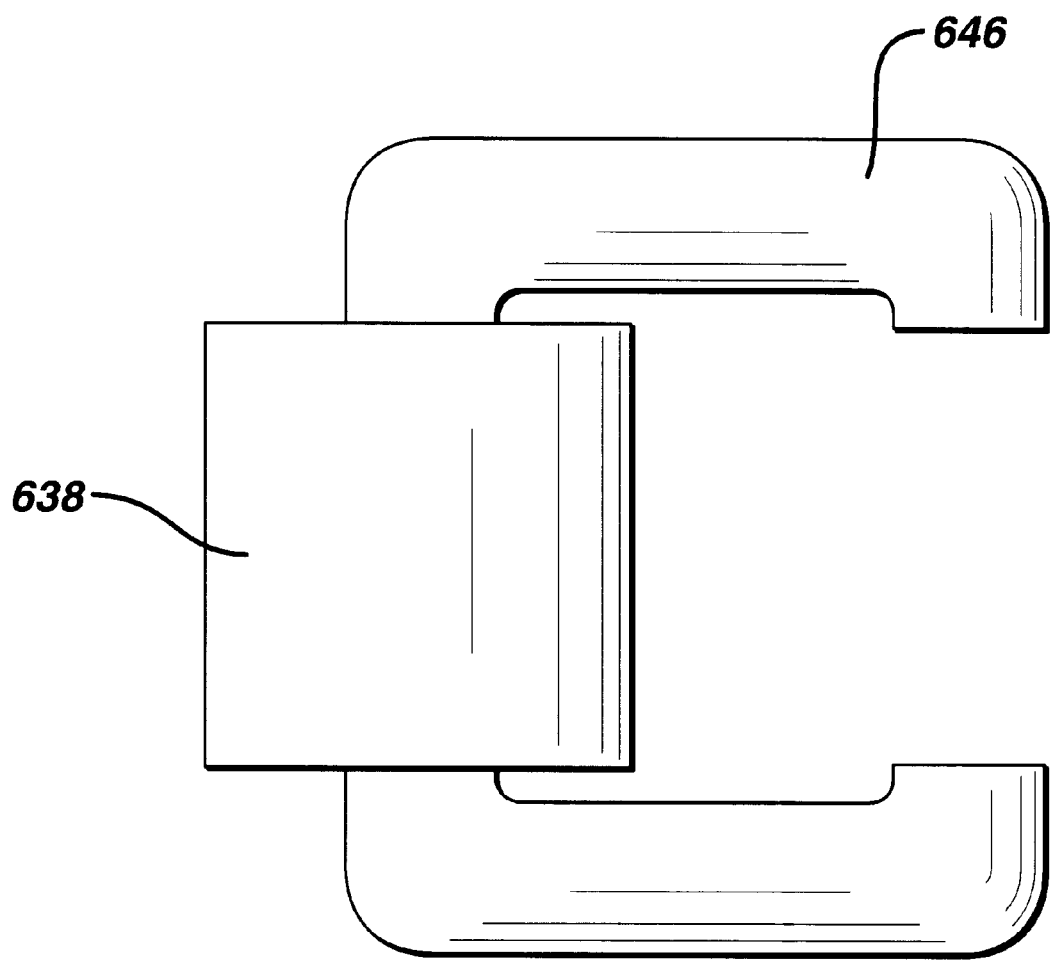
FIG. 19 is an alternate view of a coil shown in FIG. 18.

FIG. 19 is an alternate view of the "close" coil 642 and core 646 shown in FIG. 18; it will be appreciated that the "open" coil 638 and associated core 646 shown in FIG. 18 may be similarly arranged and configured.

FIGS. 20, 21, 22 and 23 illustrate, respectively: a top view of a valve body 610, with an included driven element 628, in an "open" position; a side view of the same in the "open" position; a top view of the same in the "closed" position; and a side view of the same in the "closed" position. Further illustrated are an "opened" switch 670 and a "closed" switch 674.

Figure 20:
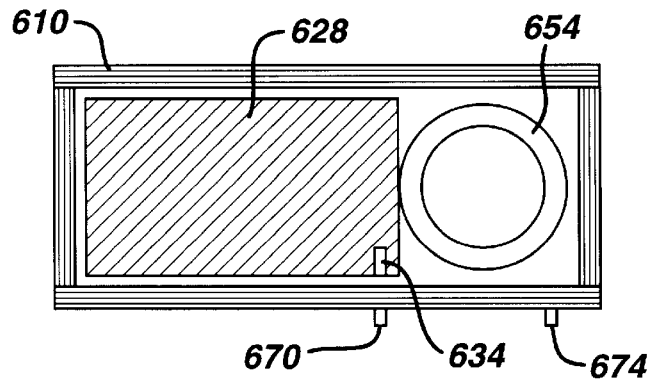
FIG. 20 is a plan view of a valve in an "open" position.
Figure 21:
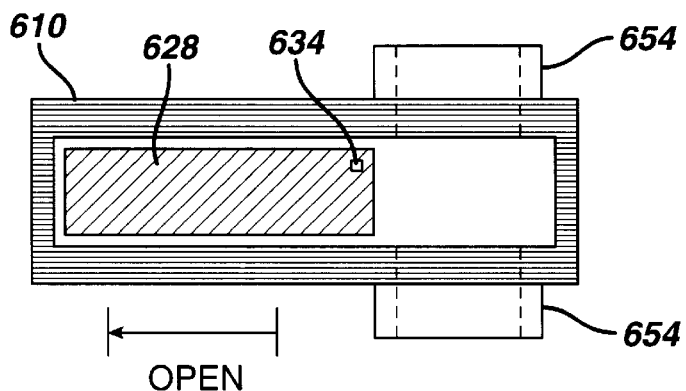
FIG. 21 is an elevational view of a valve in an "open" position.
Figure 22:
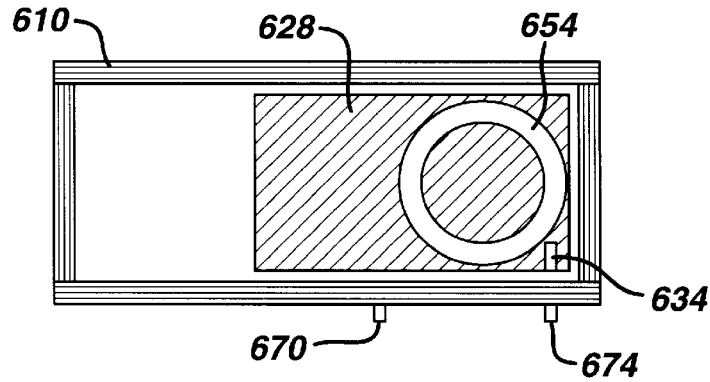
FIG. 22 is a plan view of a valve in a "closed" position.
Figure 23:
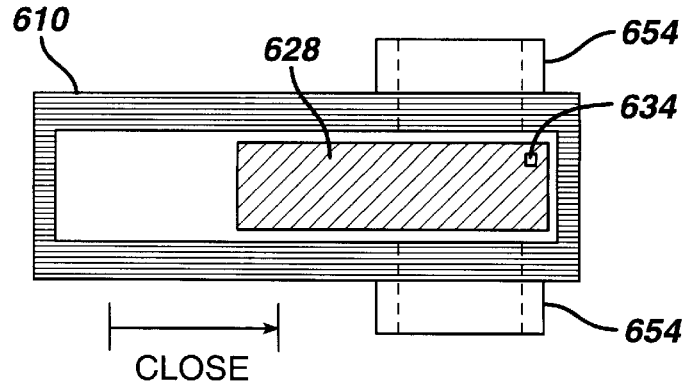
FIG. 23 is an elevational view of a valve in a "closed" position.

In accordance with a preferred embodiment of the present invention, a valving arrangement including body 610 and driven element 628 may be controlled in such a manner that, with the "open" coil 638 (see FIG. 18) being energized, the magnetic armature 630 (see FIG. 17) will ensure that driven element 628 remains in an open position as in FIGS. 20 and 21, to permit the concomitant throughflow of fluid through connectors 654. Likewise, with the "close" coil 642 (see FIG. 18) being energized, the magnetic armature 630 (see FIG. 17) will ensure that driven element remains in a closed position, to concomitantly prevent the throughflow of fluid through connectors 654 as in FIGS. 22 and 23.

Preferably, as shown in FIGS. 20 through 23, there will be suitably positioned switches 670, 674 configured for detecting the presence of permanent magnet 634. In this manner, the alignment of magnet 634 with either of the switches 670, 674 can establish that the block 628 is accurately being held, respectively, in the open or closed position. In the event that the alignment of permanent magnet 634 with either switch 670, 674 is not true, an appropriate "locating feedback" arrangement can prompt an increase in voltage to either the "open" coil 638 or "close" coil 642 (see FIG. 18), respectively, to ensure that the block 628 will subsequently move sufficiently to result in complete alignment of magnet 634 with the switch 670 or 674 in question and thus ensure that the valve is definitively opened or closed. Additionally, the switches 670, 674 may be wired in series with the coils 638, 642 (see FIG. 18) in such a manner as to remove driving voltage from either coil when the driven element 628 is definitively "in position".

The valve body 610 is preferably a simple, hollow rectangular prism made from a suitably strong and durable material, such as "PVC" (polyvinyl chloride), whereby side portions 614, 618 (see FIG. 16) can be solvent welded thereto. Further, switches 670, 674 may be embodied by any suitable switch arrangement, such as reed switches.

Preferably, a valving arrangement according to the present invention will be so arranged an configured as to suitably accommodate the piping being used in the greater apparatus in question. For example, connectors 654 (see FIG. 18) may be configured to accommodate a two-inch ID schedule 40 PVC pipe with a tight sliding fit, while also welding such pipe to the valve body 610. In this context, valve body 610 could be embodied by a section of extruded rectangular ⅜ inch PVC cut square.

FIGS. 24 through 33 illustrate embodiments of the present invention that employ pneumatic actuation of a valve.

Figure 24:
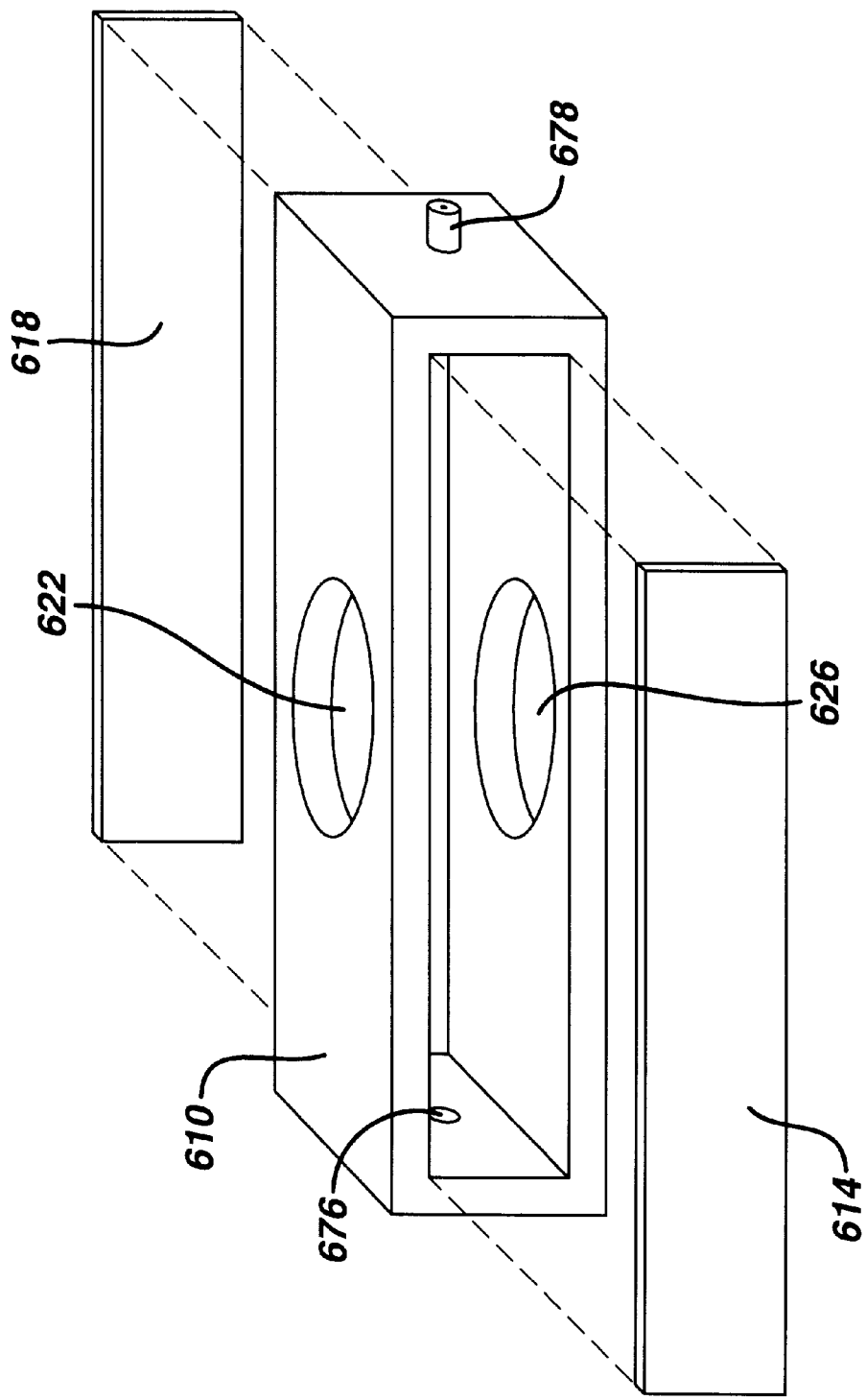
FIG. 24 illustrates a pneumatic variant construction of a valve body.

Thus, FIG. 24 illustrates a general construction of a valve body similar to that shown in FIG. 16, but additionally illustrates ports 676 and 678 for the introduction and/or retraction of compressed air (or other suitable gas) into and out of the body 610. Similarly to the arrangement shown in FIG. 16, holes 622 and 626 are provided to permit the throughflow of fluid when the valve is open; in contrast to FIG. 16, however, the holes are positioned more centrally (i.e., along the longitudinal direction of the body 610).

Figure 25:
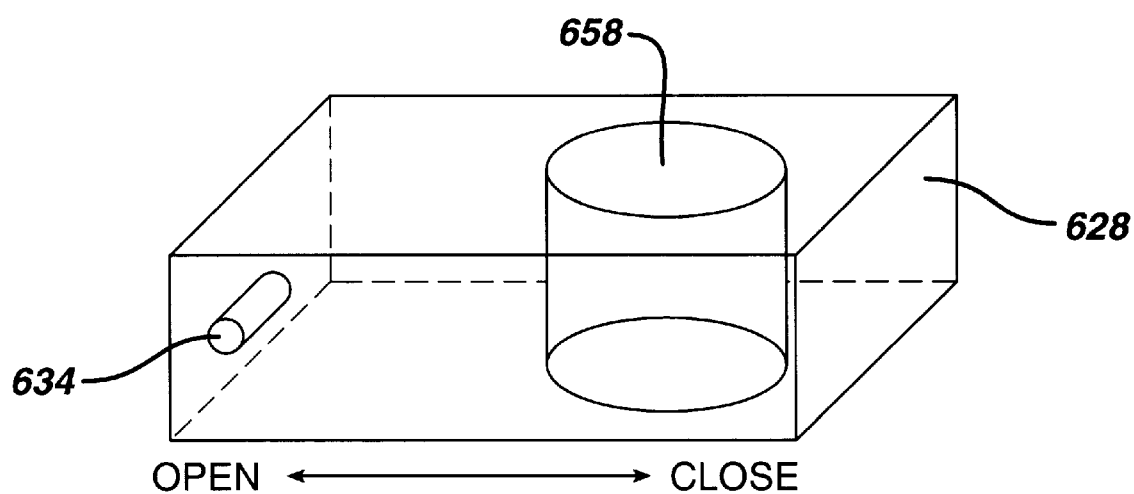
FIG. 25 illustrates a driven element for use with the valve body illustrated in FIG. 24.

FIG. 25 shows a driven element in a double-acting pneumatic system, including magnetic position feedback 634, block 628 and throughhole 658. Thus, in the embodiment shown in FIG. 24, the block 628 could be driven pneumatically from either end. In this case, the valve body 610 will likely be lengthened as compared to the case in which the driven element of FIG. 17 is used, so that, with the valve in an "open" position (i.e. with block 628 having moved towards the left), hole 658 will be aligned with holes 622 and 626 illustrated in FIG. 24.

Figure 26:
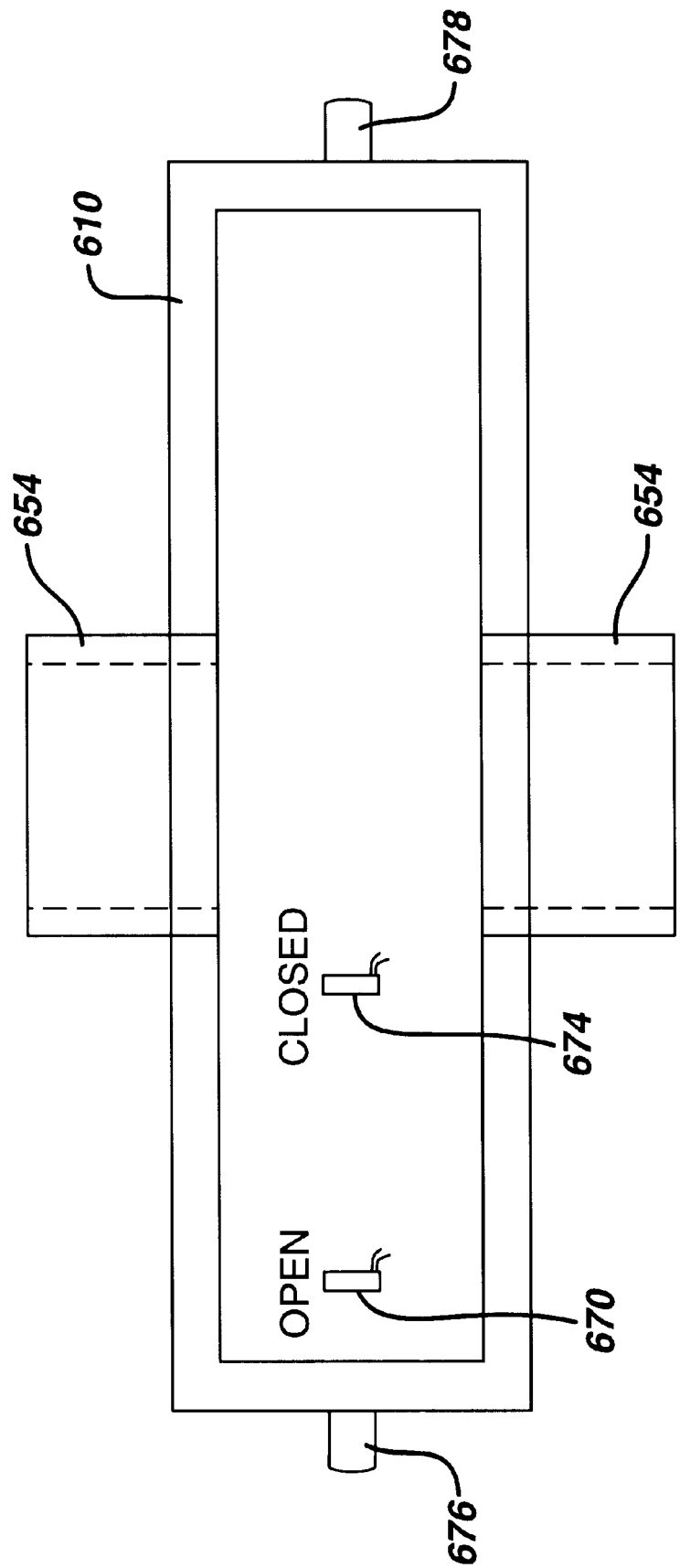
FIG. 26 is an elevational view of a complete valve according to the variant embodiment of the present invention illustrated in FIGS. 24 and 25.

FIG. 26 illustrates a body 610 similar to that shown in FIG. 24, but additionally with the provision of connectors 654 (similar to those described and illustrated with relation to FIG. 18). However, it will be noted that the connectors 654 shown in FIG. 26 are positioned essentially centrally with respect to the longitudinal direction of body 610, so as to readily accommodate the throughhole 658 of block 628 (see FIG. 25).

In accordance with a preferred embodiment of the present invention, "open" and "closed" magnetic position sensors, indicated at 670 and 674, respectively, will preferably be provided to sense the presence of the small permanent magnet 634 shown in FIG. 25. Thus, for the purposes of feedback control, the sensors 670 and 674 will function essentially similarly as compared with the embodiment shown in FIGS. 16 through 23, but, in this case, they will prompt the pneumatic apparatus in use to appropriately actuate block 628 in a manner to bring magnet 634 into full alignment with the switch 670 or 674 in question.

Actuation of block 628 (see FIG. 25) can essentially take place in any manner deemed appropriate. In one embodiment of the present invention, air (or other suitable gas) can both be applied through, and vented from, either of the ports 676/678 depending on the direction in which the block 628 is being actuated. For example, to displace block 628 from an "open" to a "closed" position, air can preferably be provided through port 676 and simultaneously vented from port 678. Conversely, to displace block 628 from a "closed" position to an "open" position, air can preferably be provided through port 678 and simultaneously vented from port 676. Examples of pneumatic apparatus (e.g., apparatus for providing and venting air in the manner just described) would appear to be well-known to those of ordinary skill in the art and will thus not be further described herein.

FIGS. 27, 28, 29 and 30 illustrate, respectively: a side view of a valve body 610, with an included driven element 628, in a "closed" position; a top view of the same in the "closed" position; a side view of the same in the "open" position; and a top view of the same in the "open" position. Further illustrated are air ports 676 and 678.

Figure 27:
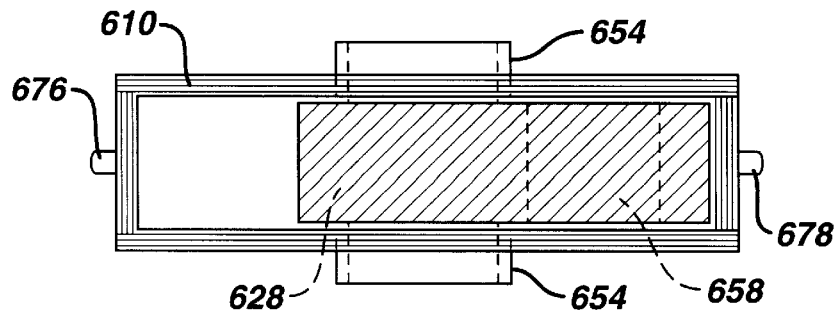
FIG. 27 is an elevational view of a valve in a "closed" position.
Figure 28:
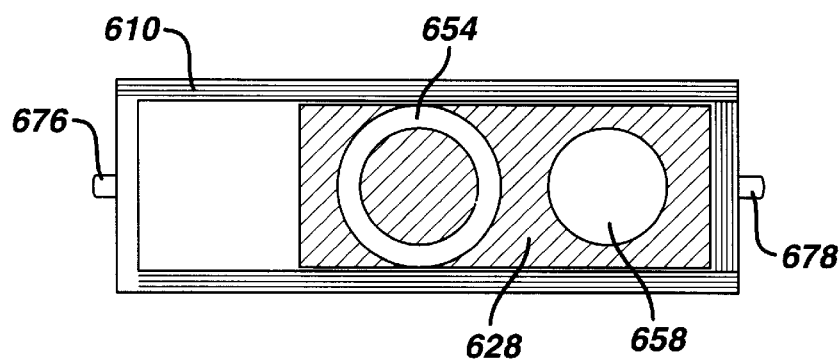
FIG. 28 is a plan view of a valve in a "closed" position.
Figure 29:
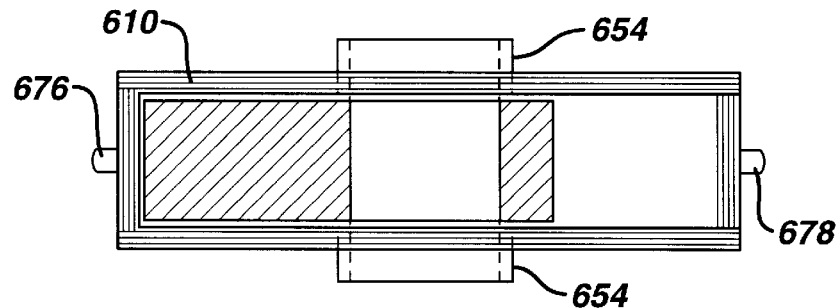
FIG. 29 is an elevational view of a valve in an "open" position.
Figure 30:
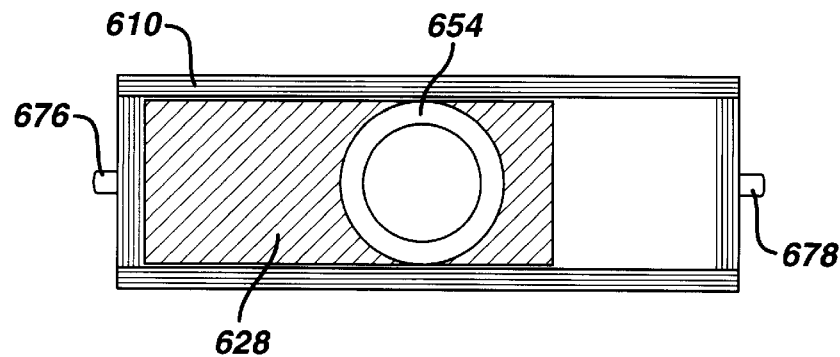
FIG. 30 is a plan view of a valve in an "open" position.

In accordance with a preferred embodiment of the present invention, a valving arrangement including body 610 and driven element 628 may be controlled in such a manner that, with air being applied through port 676 and vented through port 678, driven element 628 will be in a closed position as in FIGS. 27 and 28, to prevent the concomitant throughflow of fluid through connectors 654. Likewise, with air being applied through port 678 and vented through port 676, the driven element 628 will be in an open position, to concomitantly permit the throughflow of fluid through connectors 654 as in FIGS. 29 and 30.

With reference to FIG. 26, switches 670, 674 will preferably be configured for detecting the presence of permanent magnet 634 (see FIG. 25). In this manner, the alignment of magnet 634 with either of the switches 670, 674 can establish that the block 628 is accurately being held, respectively, in the open or closed position. In the event that the alignment of permanent magnet 634 with either switch 670, 674 is not true, an appropriate feedback arrangement can prompt a revision in the provision of air into or out of ports 676 and 678, to ensure that the block 628 will subsequently move sufficiently to result in complete alignment of magnet 634 with the switch 670 or 674 in question and thus ensure that the valve is definitively opened or closed.

Figure 31:
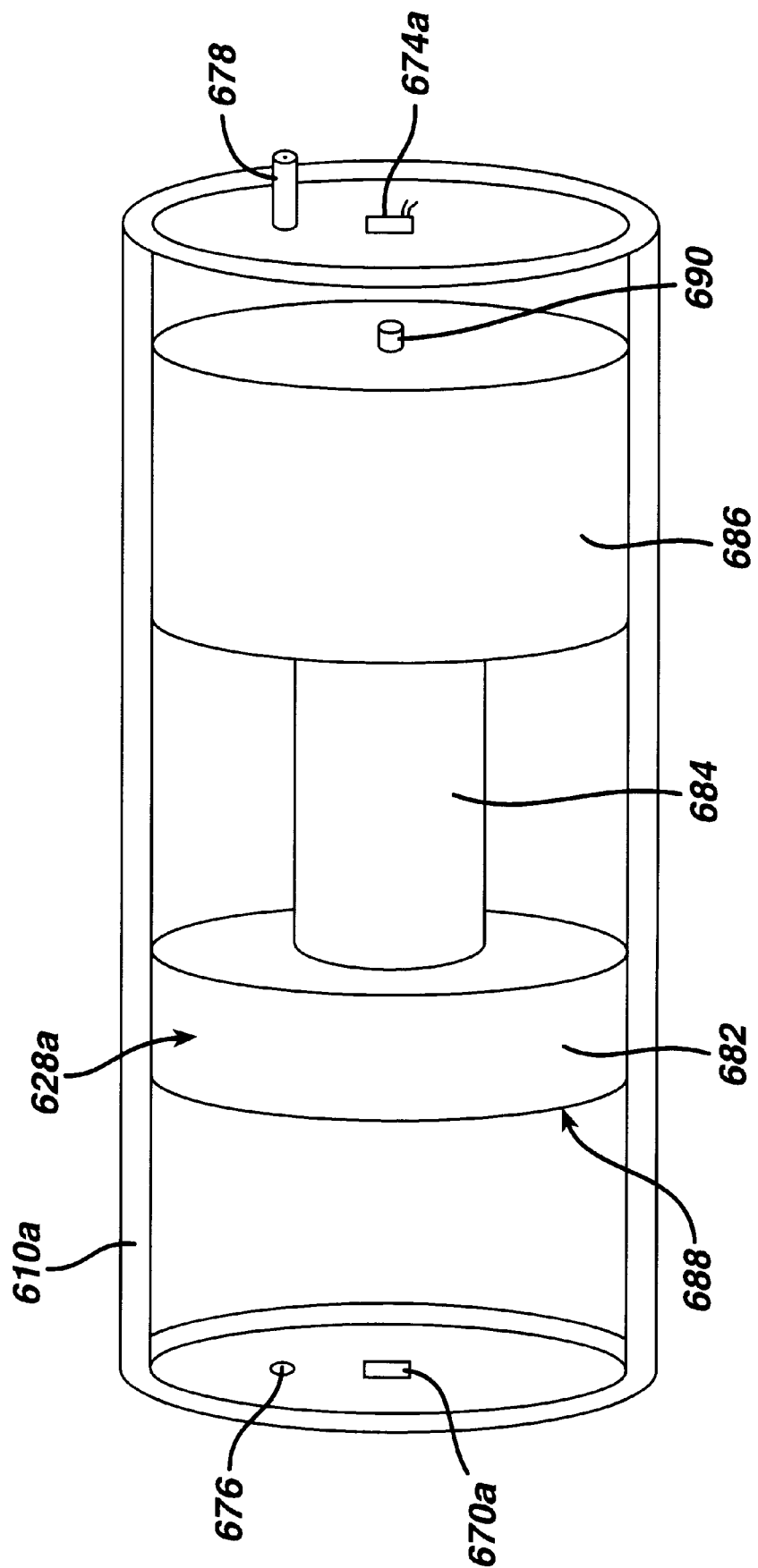
FIG. 31 illustrates a variant in which a valve housing body is cylindrical in shape.

FIG. 31 illustrates a variant in which a housing body 610a is cylindrical in shape and contains therein a compatibly shaped driven element 628a. In accordance with one embodiment of the present invention, element 628a may include a first major cylindrical portion 682, a connecting cylindrical portion 684 and a second major cylindrical portion 686. Preferably, major portions 682 and 686 will be sized so as to fit snugly (yet slideably) within body 610a, while connecting portion 684 will preferably be sized so as to minimally disrupt the cross-flow of air or fluid therepast while still providing an adequate connection between the major portions 682 and 686 (a more detailed illustration of the position of connecting portion 684 in the context of opening and closing of the valve is shown in FIGS. 32 and 33).

Preferably, magnetic position sensors 670a and 674a may, as shown, be placed at opposite end portions of the body 610a and, as such, may be configured to detect the presence of corresponding permanent magnet elements 688 (not visible in the drawing) and 690, respectively. Preferably, the magnet elements 688 and 690 will function in a manner similar to the magnet element 634 discussed heretofore, but in this case, they will preferably operate in tandem with their respective corresponding sensors 670a and 670b.

Ports for air, indicated at 676 and 678, may preferably be provided as shown.

Figure 32:
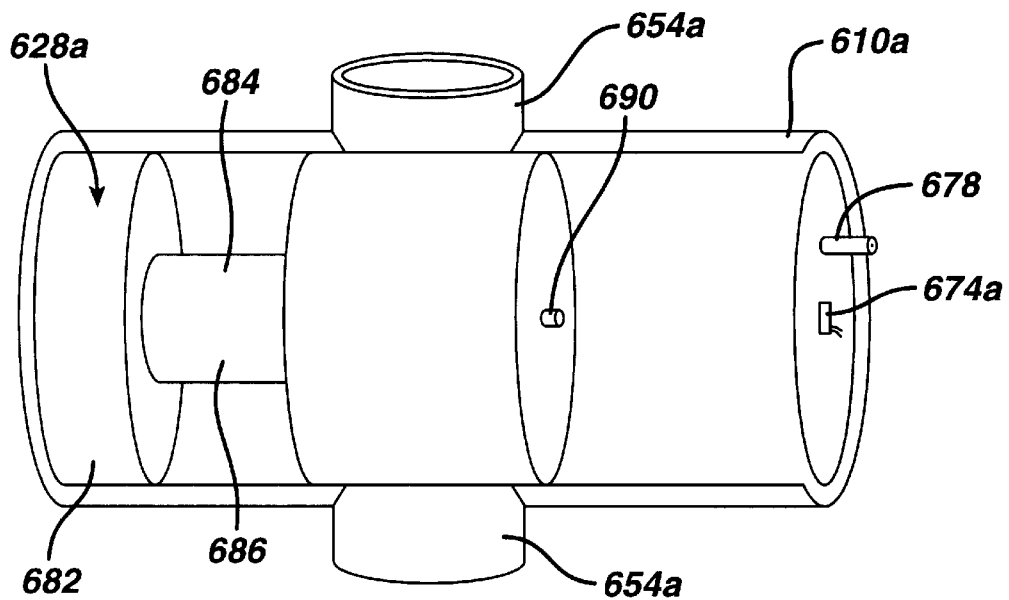
FIG. 32 shows a valve such as that illustrated in FIG. 31 in a "closed" position.
Figure 33:
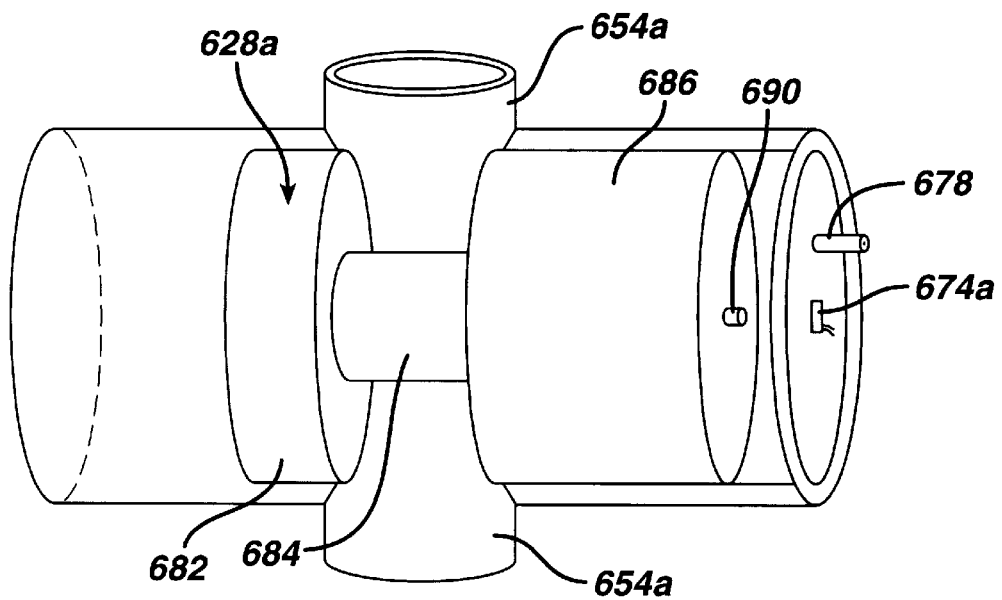
FIG. 33 shows a valve such as that illustrated in FIG. 31 in an "open" position.

FIG. 32 shows a valve such as that illustrated in FIG. 31 in a "closed" position, while FIG. 33 shows a valve such as that illustrated in FIG. 31 in an "open" position.

For high-pressure applications using any of the variants described and illustrated herein with respect to FIGS. 16 through 33, it is conceivable to modify the valving arrangement such that: the stock is strong enough to contain the operating pressure with adequate margins of safety; the aforementioned solvent welds are "pinned", while fresh, to enhance the shear strength of the welds; and the valve body 610 is slightly tapered to provide a wedged seal in the "closed" position (in such an instance, a matching taper to the driven element 628 could conceivably improve the seal, but might not be necessary).

From the foregoing, it will be appreciated that the present invention contemplates, in accordance with at least one preferred embodiment, a simple and reliable arrangement for providing a locating feedback to ensure substantially precise positioning of a driven element within a valve housing. Further, it will be appreciated that seal-less valving arrangements according to the present invention provide a simple, inexpensive design permitting flow control within a hermetically tight valve body. The sliding element in a sealed case essentially eliminates any danger of leakage, while the design results in a reliable valve at a fraction of the cost of valves currently available. The valves described hereabove may also be considered to be "stem-less", since no external stem or piston is required to penetrate through the valve housing.

A STACKABLE LOW-PRESSURE SHUTTLE VALVE SYSTEM

The disclosure now turns to an example of a shuttle valve system that may be utilized in accordance with at least one embodiment of the present invention.

Preferably, the shuttle valve (generally indicated at 710) will be actuable between two positions, one of which, hereinafter referred to as "position one", is shown in FIG. 34, and the other of which, hereinafter referred to as "position two", is illustrated in FIG. 35.

Preferably, a shuttle 714 can be disposed within a housing 718 in a slideable manner. Preferably provided at opposite ends of sliding chamber 722 provided within housing 718 are springs 726 and 730, while springs 726 and 730 are each configured to respectively stretch and compress when the other is respectively compressed and stretched.

Preferably, the valve comprises four ports 734, 738, 742 and 746. Preferably, ports 734 and 738 will be aligned with one another, while ports 742 and 746 will be aligned with one another. Preferably, shuttle 714 (shown in greater detail in FIG. 36) includes a first major portion 750 and a second major portion 754 interconnected by a narrow-neck portion 758. Accordingly, the decrease in diameter of narrow-neck portion 758 with respect to major portions 750 and 754 preferably results in the formation of an annular gap 762 (see FIGS. 34 and 35). Accordingly, in "position one" as illustrated in FIG. 34, shuttle 714 may preferably be maximally displaced towards the left of the figure, such that annular gap 762 is aligned with ports 734 and 738. Conversely, in "position two" as illustrated in FIG. 35, shuttle 714 will preferably be maximally displaced towards the right of the figure, thus aligning annular gap 762 with ports 742 and 746.

Preferably, the narrow-neck portion 758 results from a rectangular cut around the greater cylinder constituted by portions 750 and 754, such that the orientation of the cylinder constituted by portions 750 and 754, while in the housing 718 (or in a tube) does not affect the opening of the ports.

As an alternative to the two-spring arrangement shown in FIGS. 34 and 35, one spring could be replaced with an actuator, such as a pneumatic connection to a pressure source or a mechanical linkage to a limited-throw actuator.

Figure 39:
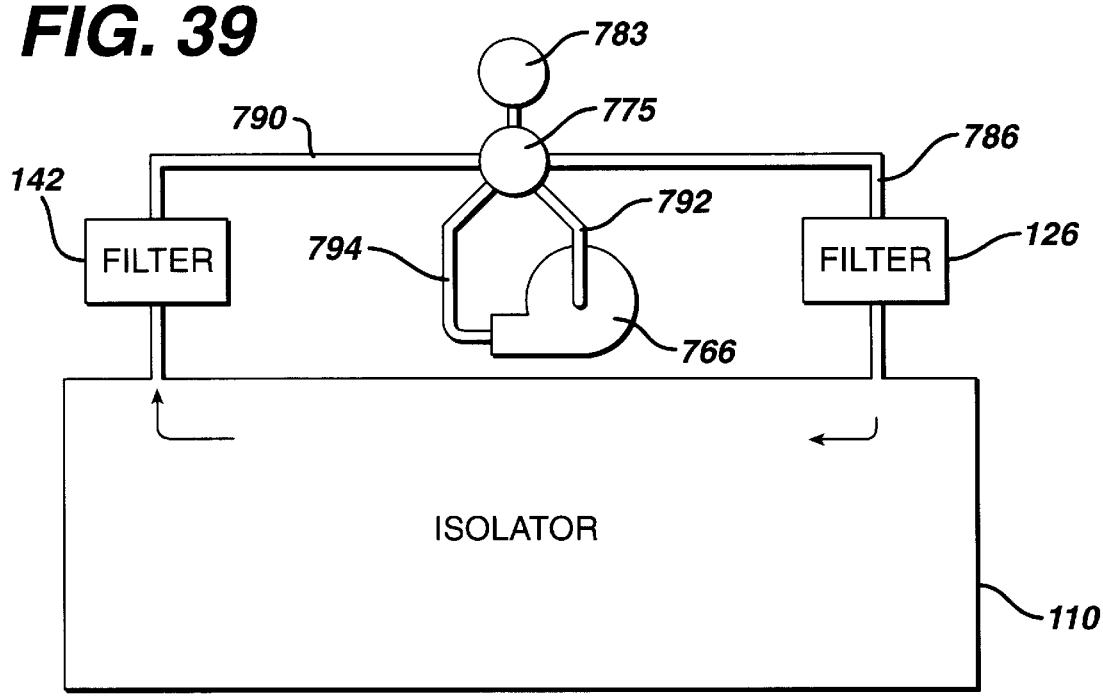
FIG. 39 illustrates, in schematic form, a possible operating environment employing the valve-and-blower arrangement illustrated in FIGS. 37 and 38.
Figure 40:
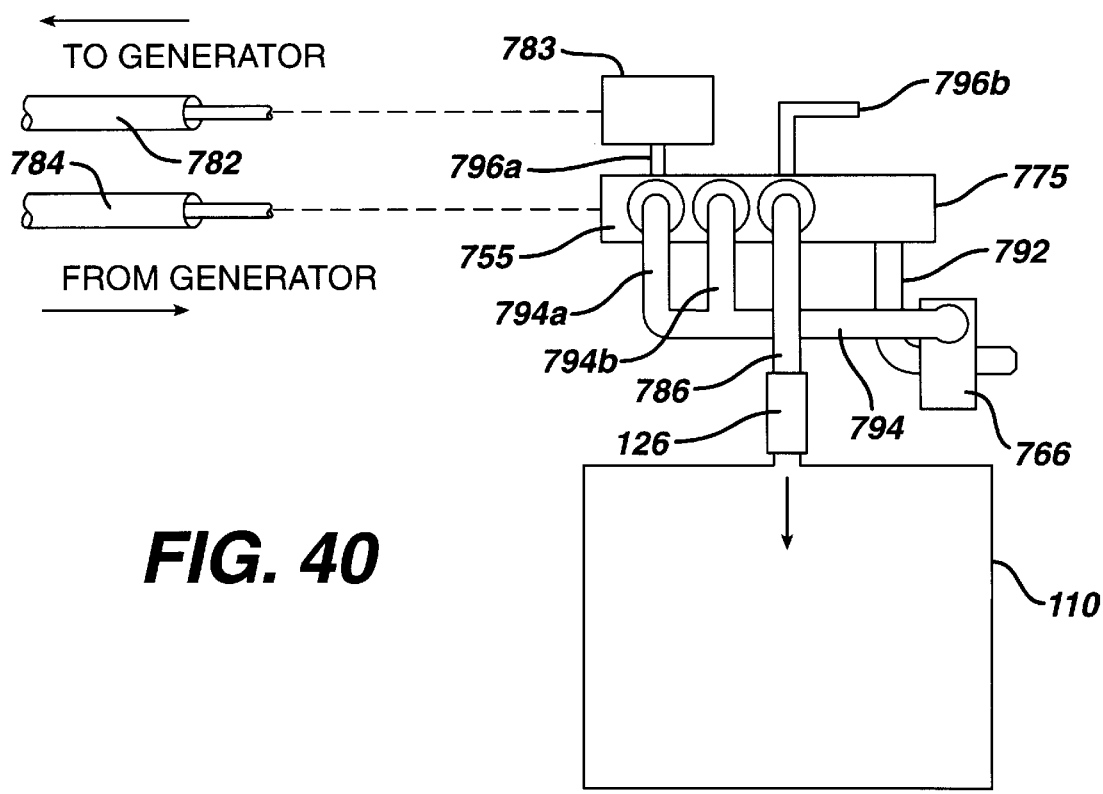
FIG. 40 illustrates an alternative view of the arrangement shown in FIG. 39.

The disclosure now turns to an example of a valving arrangement, using shuttle-type valves such as those described and illustrated with respect to FIGS. 34 through 36, that may be utilized for the purposes of deflating and/or evacuating a flexible-walled isolator (or other enclosed space), in the context of a general arrangement of an inlet line, outlet line, blower and interconnection lines similar to that described and illustrated herebelow with respect to FIGS. 39 and 40.

Figure 37:
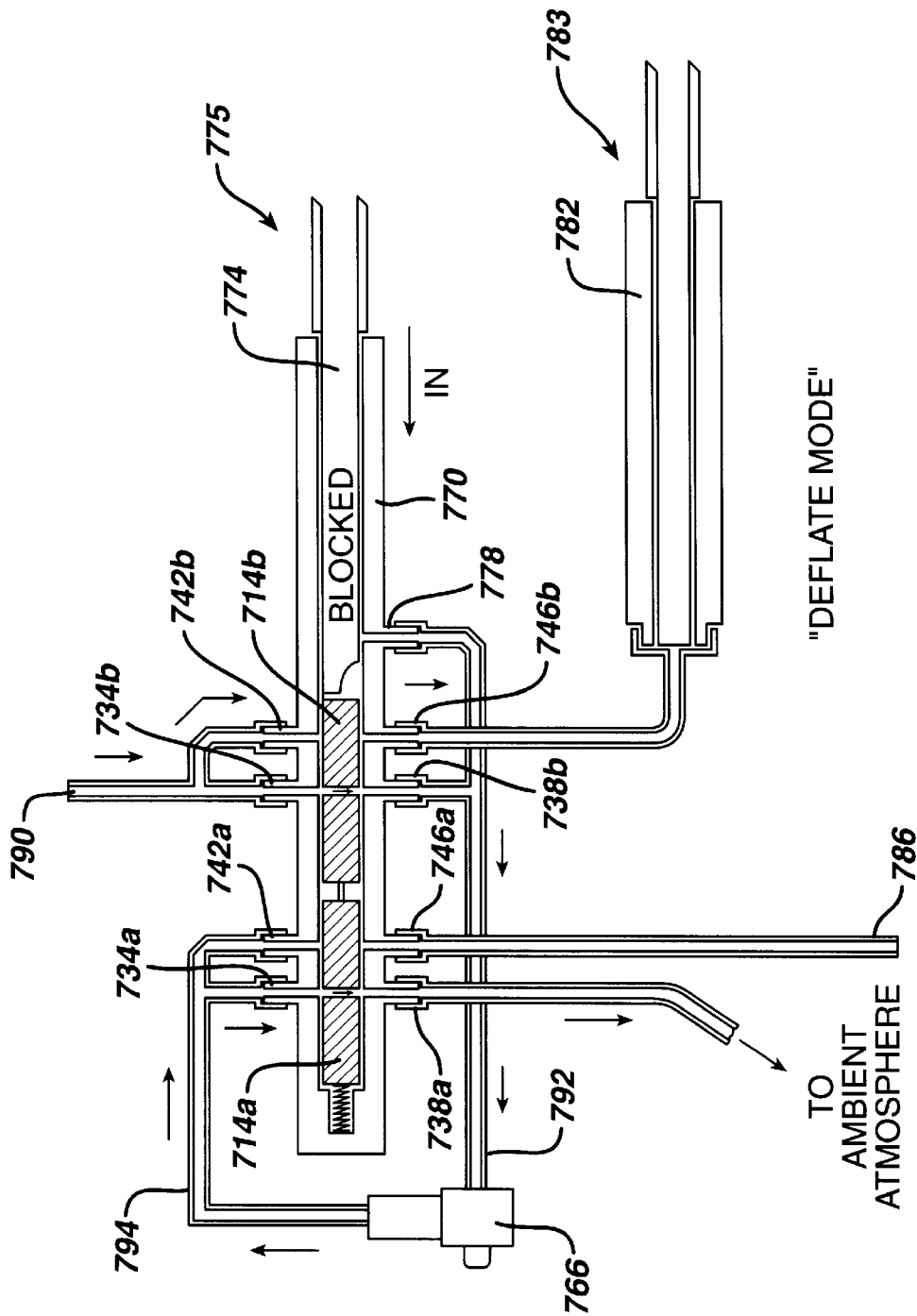
FIG. 37 illustrates a valve-and-blower arrangement in a "deflate" configuration.

FIG. 37 illustrates shuttle in a "deflate" position, in which a flexible-walled isolator (or other enclosed space) can be evacuated and/or deflated prior to a sterilization process. Illustrated are actually two shuttle valve bodies 714*a* and 714*b*, each being operable to open and close port pairs 734*a* and 738*a*; 742*a* and 746*a*; 734*b* and 738*b*; and 742*b* and 746*b*. Again, each shuttle preferably affords the creation of annular gaps (similarly to the gap indicated at 762 in FIG. 34).

As shown, an inlet 775 (i.e. a port for accepting air/gas from a sterilizing apparatus that is subsequently to be transferred to an isolator or other enclosed space) and an outlet 783 (i.e. a port for returning air/gas to a sterilizing apparatus from an isolator or enclosed space) may be interconnected with a blower 766. Particularly, a port 778 from inlet 775 may join with port 738*b* to lead to an inlet of blower 766, while an outlet of blower 766 may lead to shuttle valve inlet ports 734*a* and 742*a*. Suitable probes 774 and 782, respectively, originating from a sterilization/decontamination apparatus, may be insertable at inlet 775 and outlet 783.

As regards the interconnection of the shuttle valving arrangement shown in FIG. 37 with an isolator, port 746*a* may preferably lead to an isolator inlet line 786, while an isolator outlet line 790 may lead to shuttle valve ports 734*b* and 742*b*. Thus, air/gas delivered into the isolator via port 746*a* and line 786 will subsequently return via line 790 and ports 734*b* and 742*b*.

As also shown in FIG. 37, port 738*a* may serve to direct air or gas to the ambient atmosphere and port 738*b* may serve to direct circulated air/gas to blower 776.

It may now be appreciated that, with the shuttles 714*a/b* in the position shown in FIG. 37, air/gas will be drawn out of the attached isolator or enclosed space via line 790, but will not be fed in via line 786. In this manner, with the arrangement shown in FIG. 37, the isolator or enclosed space can be evacuated, and, in the case of flexible-walled isolators, deflated, whereby air/gas will only leave the isolator or enclosed space but will not be replenished.

Accordingly, assuming that a docking probe or tube 774 is being used to insert a feed line from the sterilizing apparatus into an inlet sleeve 770, probe 774 will preferably block port 778. At the same time, with the annular gap of shuttle 714*b* being positioned to provide fluid communication between ports 734*b* and 738*b*, and with the annular gap of shuttle 714*a* being positioned to provide fluid communication between ports 734*a* and 738*a*, it will be appreciated that the effect of running blower 766 will be to draw air/gas from the interior of the isolator or enclosed space (via line 790) and feed the same directly to the ambient atmosphere.

Conversely, it will also now be appreciated that, with the shuttles 714*a/b* in the position shown in FIG. 38, air/gas will be fed into the isolator or enclosed space via line 786 and will subsequently be drawn out via line 790. In this manner, with the arrangement shown in FIG. 38, continuous circulation of air/gas through the isolator or enclosed space can take place, for example, during a sterilization process.

Accordingly, at this point, probe 774 will preferably not be blocking port 778. At the same time, with the annular gap of shuttle 714*b* being positioned to provide fluid communication between ports 742*b* and 746*b*, and with the annular gap of valve body 714*a* being positioned to provide fluid communication between ports 742*a* and 746*a*, it will be appreciated that the effect of running blower 766 will be to draw air/gas from the sterilizing apparatus (via inlet port 770) and feed the same to isolator inlet line 786. At the same time, air/gas fed into the isolator or enclosed space via inlet line 786 will force air/gas from within the isolator or enclosed space out through outlet line 790 and thence to outlet port 782.

Figure 38:
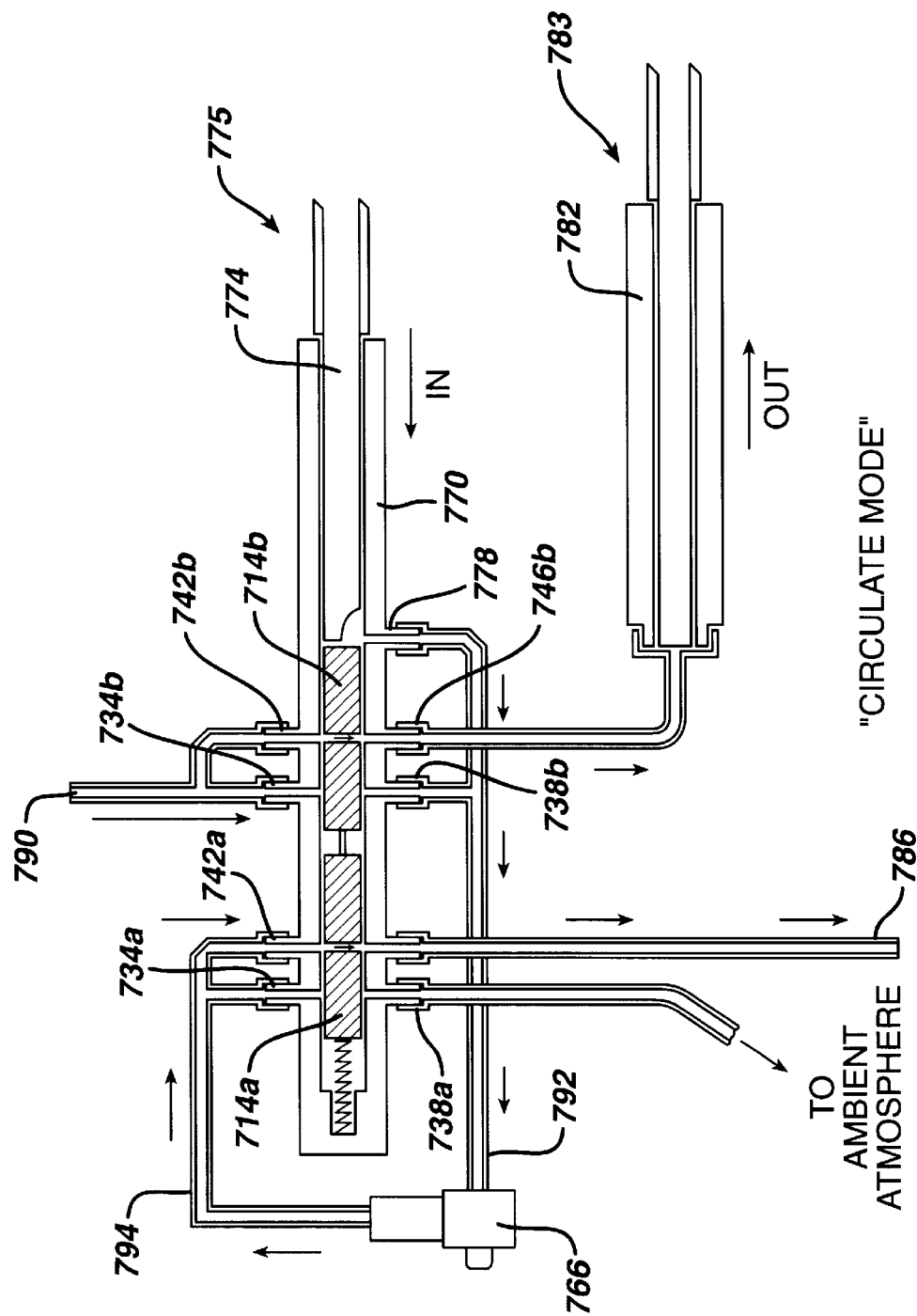
FIG. 38 illustrates the same valve-and-blower arrangement as FIG. 37 but in a "circulate" configuration.

For the purpose of interconnecting shuttles 714*a* and 714*b*, and thus ensuring that they will move in tandem so as to effect the two control positions illustrated in FIGS. 37 and 38, essentially any suitable arrangement may be employed, such as a short cylindrical rod portion connecting the two valve bodies along the longitudinal axes of the valve bodies.

With reference to FIG. 37, in accordance with a presently preferred embodiment of the present invention, the probe 774 may preferably be configured so that, upon pushing the shuttles 714*a* and 714*b* to the left (in the drawing) against a spring force, it will lock in place. Thus, it is conceivable to configure probe 774 in a manner that, by merely inserting it into sleeve 770 up to a predetermined limit position (defined, for example, by suitable configured and arranged stops), it will lock in place at the predetermined limit position and, as a result, cause shuttles 714*a* and 714*b* to assume the configuration shown. Preferably, a solid portion of probe 774 will sufficiently cover port 778 so as to prevent the transfer of gas or fluid from probe 774 to port 778.

On the other hand, as shown in FIG. 38, probe 774 may preferably be so configured and arranged such that, upon partial retraction of the probe 774 from sleeve 770, it may lock into a second position corresponding to partial, but not complete, insertion of the probe 774. In this position, shuttles 714*a* and 714*b* will preferably assume the configuration shown and, furthermore, as shown, a suitably configured and arranged "notch" (or other opening or recess) in probe 774 will permit the transfer of gas or fluid from probe 774 to port 778.

Arrangements for effecting the type of "locking in position" described hereabove, for permitting probe 774 to be held in each of the positions illustrated in FIGS. 37 and 38, would appear to be well-known to those of ordinary skill in the art and will thus not be described further herein.

Although the shuttle valves described and illustrated with respect to FIG. 34 through 38 have been described and illustrated primarily with respect to a gas generating system such as that described and illustrated herein, it is conceivable to utilize them in environments or contexts different from gas generating systems.

The present invention contemplates, in accordance with at least one preferred embodiment, an arrangement such as that schematically illustrated in FIGS. 39 and 40. As shown in FIGS. 39 and 40, an inlet 775 (accepting circulated air/gas from a sterilant generator) can preferably have, branching off therefrom, lines 786 and 792. Line 792 can preferably lead from the inlet of blower 766 to ports 738b and 778 (see FIGS. 37 and 38), with an outlet line 794 of the blower leading from shuttle valve ports 734a and 742a (see FIGS. 37 and 38). As shown, line 786 may then preferably lead to filter 126 and isolator 110. Thus, in accordance with a preferred embodiment of the present invention, a blower 766 may be configured to circulate air/gas in the vicinity of the inlet 775 in order to permit continuous circulation of air/gas through isolator 110 and the attached sterilant generator (not shown).

After passing through a filter 142, circulated air/gas exiting from isolator 110 may be directed through line 790 into shuttle valve ports 734b and 742b (see FIGS. 37 and 38), thence to be directed either to blower 766 in the "deflate" mode (as shown in FIG. 37) or to outlet connection 782 in the "circulate" mode (as shown in FIG. 38).

It is to be understood that the views illustrated in FIGS. 39 and 40, where needed, are exaggerated in portions for the purpose of emphasizing the blower 766 and its connections. Bearing this in mind, the following components are illustrated merely schematically in order to complete the drawing: line 796a (which, in the context of FIGS. 37 and 38, would lead from port 746b to outlet 783) and line 796b (which, in the context of FIGS. 37 and 38, would lead to the ambient atmosphere from port 738a).

One manner of circulating air/gas into and out of isolator 110 has been described more fully above with respect to FIGS. 37 and 38. As such, FIGS. 37 and 38, and the attendant description, illustrate an arrangement in which the basic structure of: inlet and outlet lines from a sterilizing apparatus, inlet and outlet lines into an isolator, a blower, and interconnecting lines, can be utilized, in accordance with a preferred embodiment of the present invention, to deflate a flexible-walled isolator prior to a sterilizing process and to circulate air/gas into and out of the isolator during a sterilizing process.

It is to be understood that the arrangement described and illustrated hereinabove with respect to FIGS. 34 through 40 has been found to be particularly suitable for a "single-blower" arrangement, that is, an arrangement in which only an isolator blower 766 is utilized for circulating sterilant gas into an isolator 110 and also through an attached sterilizing apparatus. However, it is also conceivable for a sterilizing apparatus itself to have a blower to aid in circulation, an example of which is described and illustrated herebelow with respect to FIG. 41. In this latter scenario, in which more than one blower might be utilized, it is possible to utilize an arrangement other than the valve arrangement described and illustrated with respect to FIGS. 34 through 40. Particularly, in such a context, it is possible to essentially eliminate the shuttle valve arrangement illustrated and described with respect to FIGS. 34 through 40 and simply utilize existing valving arrangements, already present within the sterilizing apparatus, to first evacuate (or in the case of a flexible-walled isolator, deflate) an isolator or enclosed space and then circulate sterilant gas through the isolator/enclosed space and sterilizing apparatus. Thus, for example, it is possible to effect the aforementioned evacuation/deflation by simply controlling the system valves so as to draw air/gas out of an isolator/enclosed space and vent the same way (e.g., with reference to FIG. 41, by having valves 282, 218 and 290 closed with valve 306 [and possibly 1222] open). Similarly, circulation may be effected by controlling the system valves as shown herebelow with reference to FIG. 44.

SETUP AND OPERATION OF GAS-GENERATING SYSTEMS—OVERVIEW

The disclosure now turns to various procedures that can be conducted in conjunction with a gas generating system according to at least one embodiment of the present invention. To facilitate in the discussion of such procedures, reference shall first be made to FIGS. 41 through 45, which provide simplified schematic illustrations of several basic components of a gas generating system according to at least one preferred embodiment of the present invention. It is to be understood that the terminology "gas generating system" may be considered to be interchangeable with the terminology "gas generator", and even possibly "gas generating and recovery system."

Figure 41:
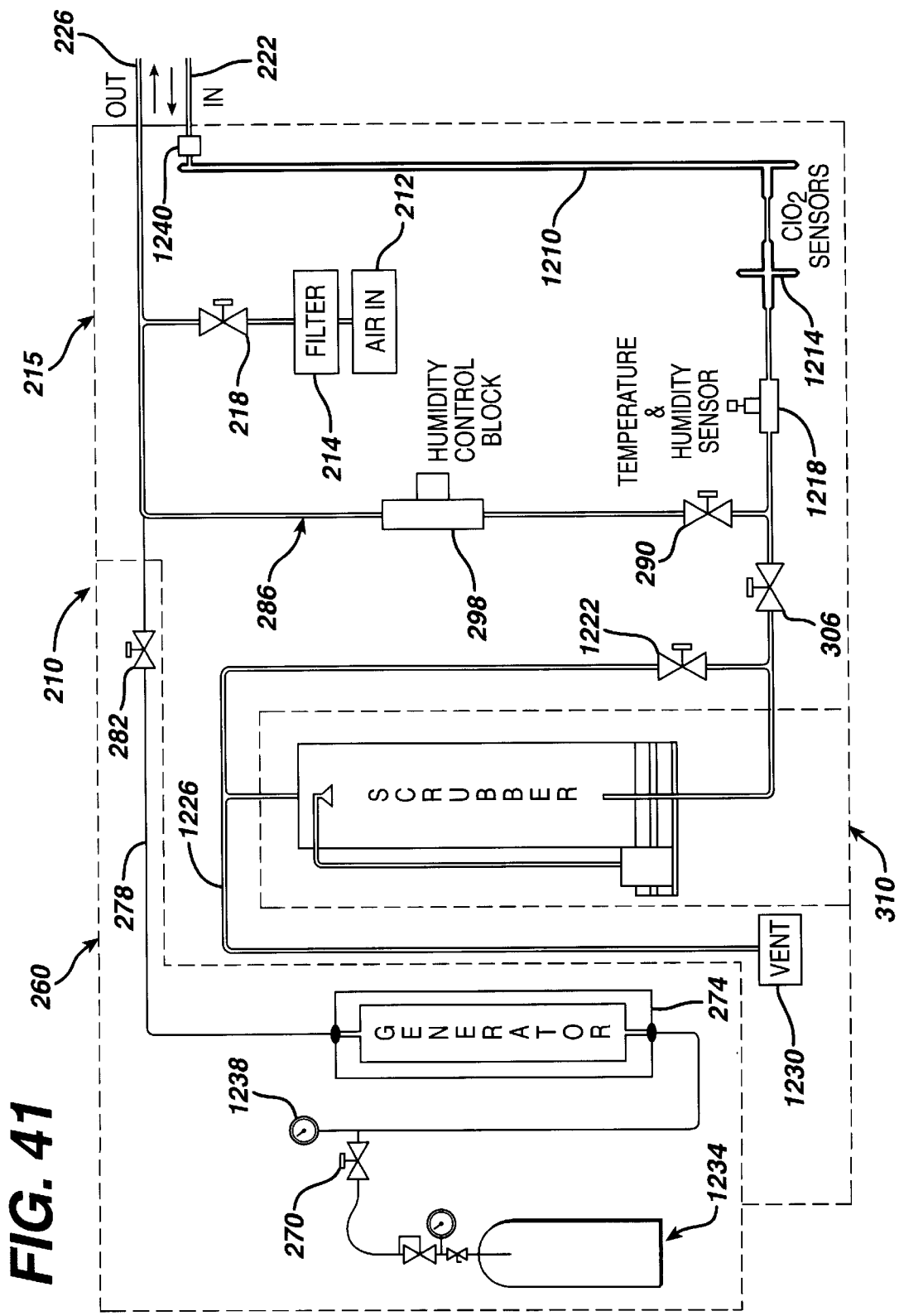
FIG. 41 illustrates a sterilization/decontamination apparatus that may be utilized in accordance with the embodiments of the present invention.

FIG. 41 illustrates a sterilization/decontamination apparatus 210 that may be utilized in accordance with at least one embodiment of the present invention, and also schematically indicates adapter section 215, gas generation system 260 and recovery system 310 in a manner similar to FIG. 8.

Proceeding from inlet portion 222, there may be provided chlorine dioxide sensors 1210 and 1214 that could each be substantially similar in makeup to the sensor described and illustrated with respect to FIGS. 14 and 15. As shown, sensor 1210 may be of significant length (shown here in schematic and exaggerated view), to facilitate the measurement of low-level $ClO_2$ concentrations, whilst sensor 1214 could be substantially smaller, to facilitate the measurement of high-level $ClO_2$ concentrations.

Beyond the second chlorine dioxide sensor 1214, a suitable temperature and humidity sensor 1218 could preferably be provided.

A line 286, similar that described and illustrated with respect to FIG. 6 could then extend between the "in" and "out" sides of the gas generating system 210 and, similarly to that illustrated in FIG. 6, could include a control valve 290 and a heater/humidifier 298.

Proceeding past the junction with line 286, a line (conceivably similar to the line 302 illustrated and described with respect to FIG. 6), could include a control valve 306. This line could then preferably lead into recovery arrangement 310. FIG. 41 shows the inclusion of control valve 1222 and an overall recovery apparatus 310 which could contain several of the components, associated with a scrubbing arrangement, illustrated in FIG. 6.

Preferably, a vent line 1226 may extend away from recovery apparatus 310 and terminate at a suitable vent 1230.

FIG. 41 illustrates a gas supply 1234. Gas supply 1234 could include a suitable tank containing, for example, 2% $Cl_2$ and 98% $N_2$, although other types of contents are of course conceivable. This arrangement 1234 could preferably feed into a control valve 270, followed by a pressure sensor 1238 (for the purpose of ascertaining whether gas is flowing from supply 1234), and then lead into a suitably arranged and configured chlorine dioxide gas generator 274. The output of gas generator 274 could lead into control valve 282, which in turn could lead into a line which itself leads to outlet portion 226. Prior to arriving at outlet portion 226, however, and subsequent to the junction with line 286, there could preferably be an "air in" portion 212 (conceivably substantially similar to that described and illustrated with respect to FIG. 6), itself including a filter 214, which then could preferably feed into control valve 218 and then into the line leading to outlet portion 226.

FIG. 41 also schematically indicates the inclusion of a blower 1240 at the inlet portion 222 of adapter section 215. This blower 1240 may be provided to "boost" the circulation of sterilant gas in conjunction with any blower associated with the isolator or other enclosed space. In such a context, it will be appreciated that the method of deflating and/or evacuating the interior of the isolator or enclosed space may take place in a manner as discussed hereabove as an alternative to the valving arrangement described and illustrated with respect to FIGS. 34 through 40.

FIGS. 42 through 45 illustrate different modes of operation that may be realized in accordance with a gas generating and recovery system such as that illustrated in FIG. 41. It will be appreciated that several valves illustrated in FIGS. 42 through 45, particularly valves 218, 282, 290, 306 and 1222 are alternatively illustrated as either being opened or closed, depending on the mode of operation being undertaken.

Figure 42:
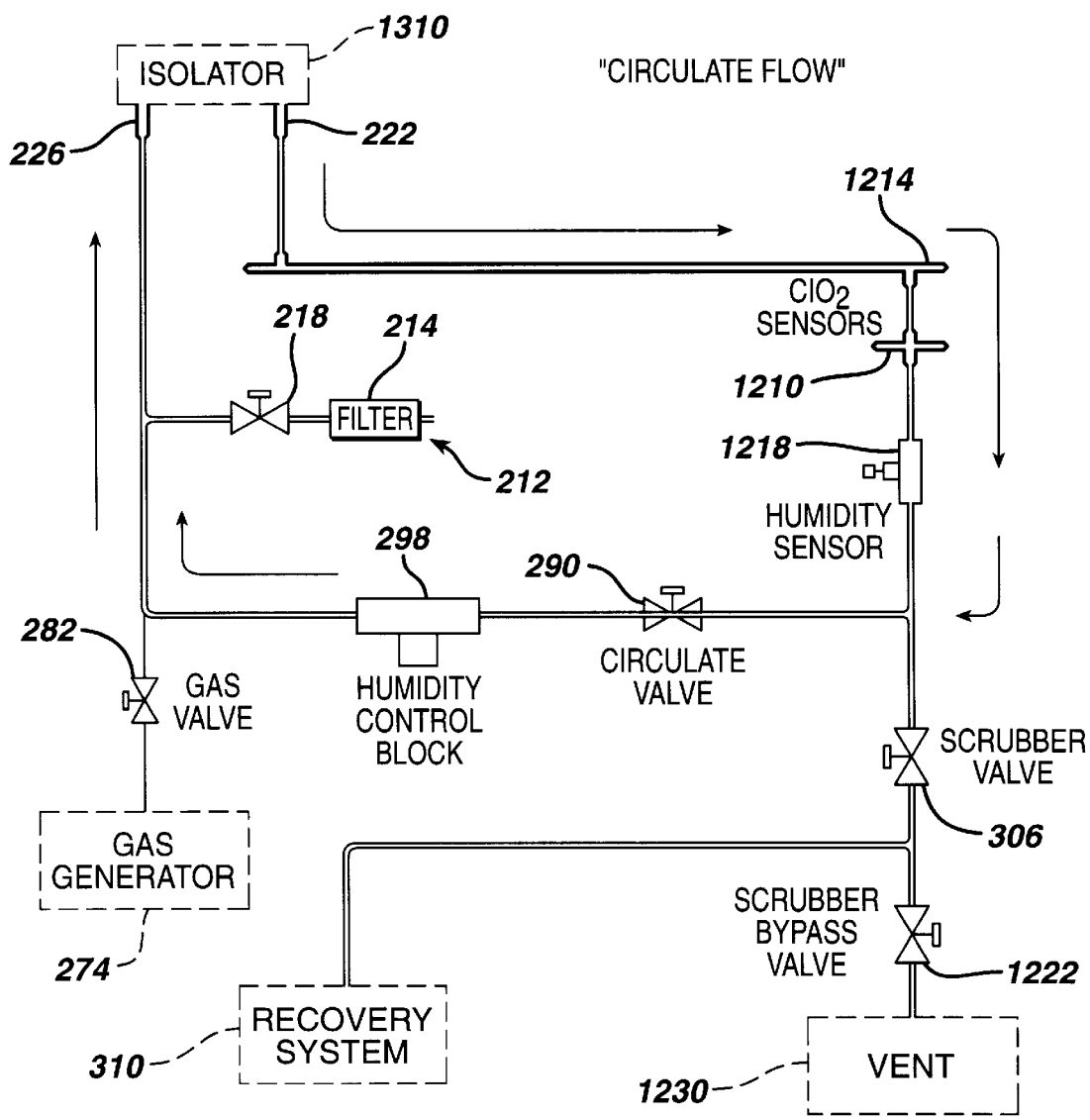
FIG. 42 illustrates, in schematic form, a "circulate flow" mode of operation of the system shown in FIG. 41.
Figure 43:
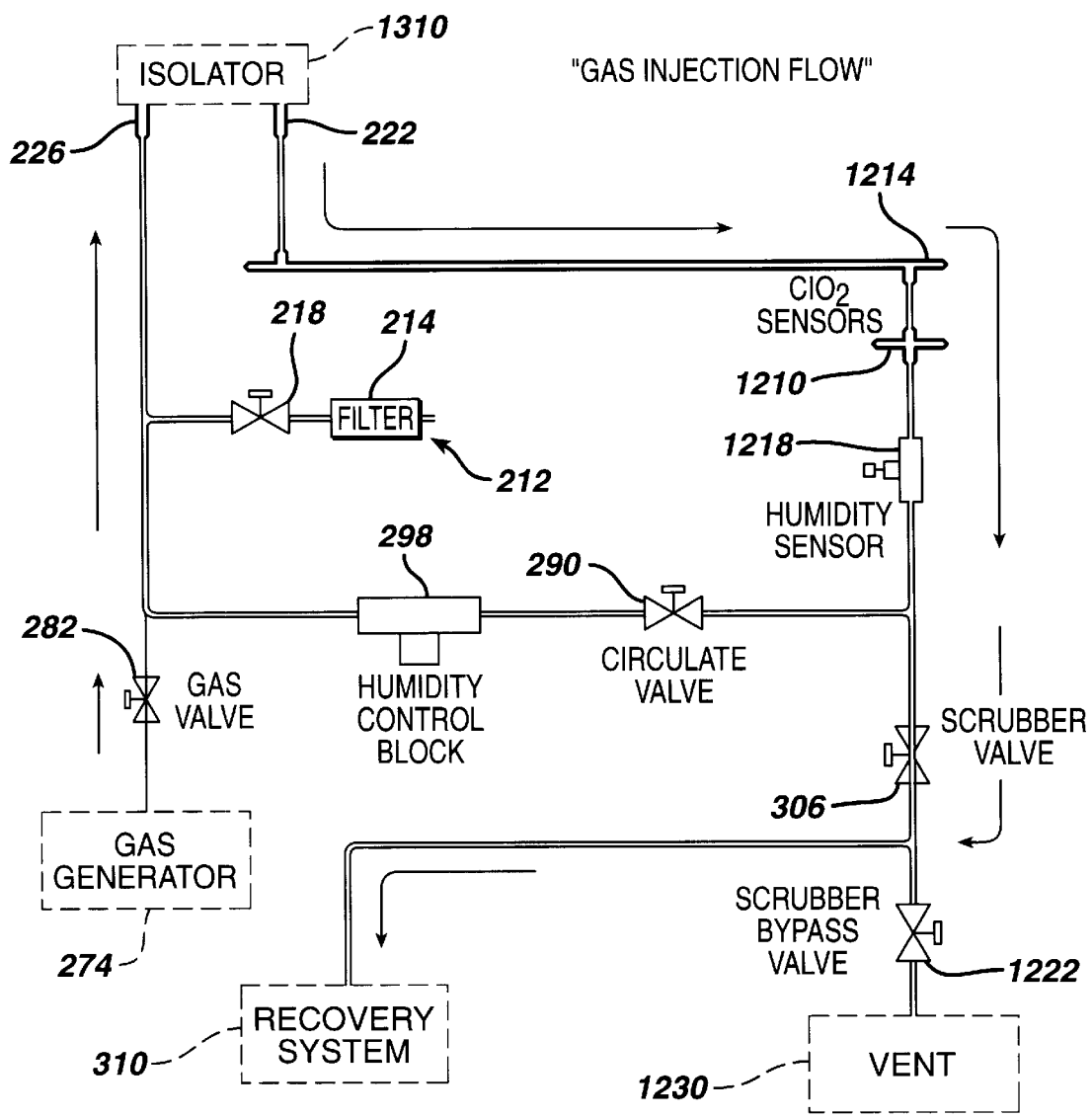
FIG. 43 is essentially the same view as FIG. 42 but illustrating a "gas injection flow" mode of operation.
Figure 44:
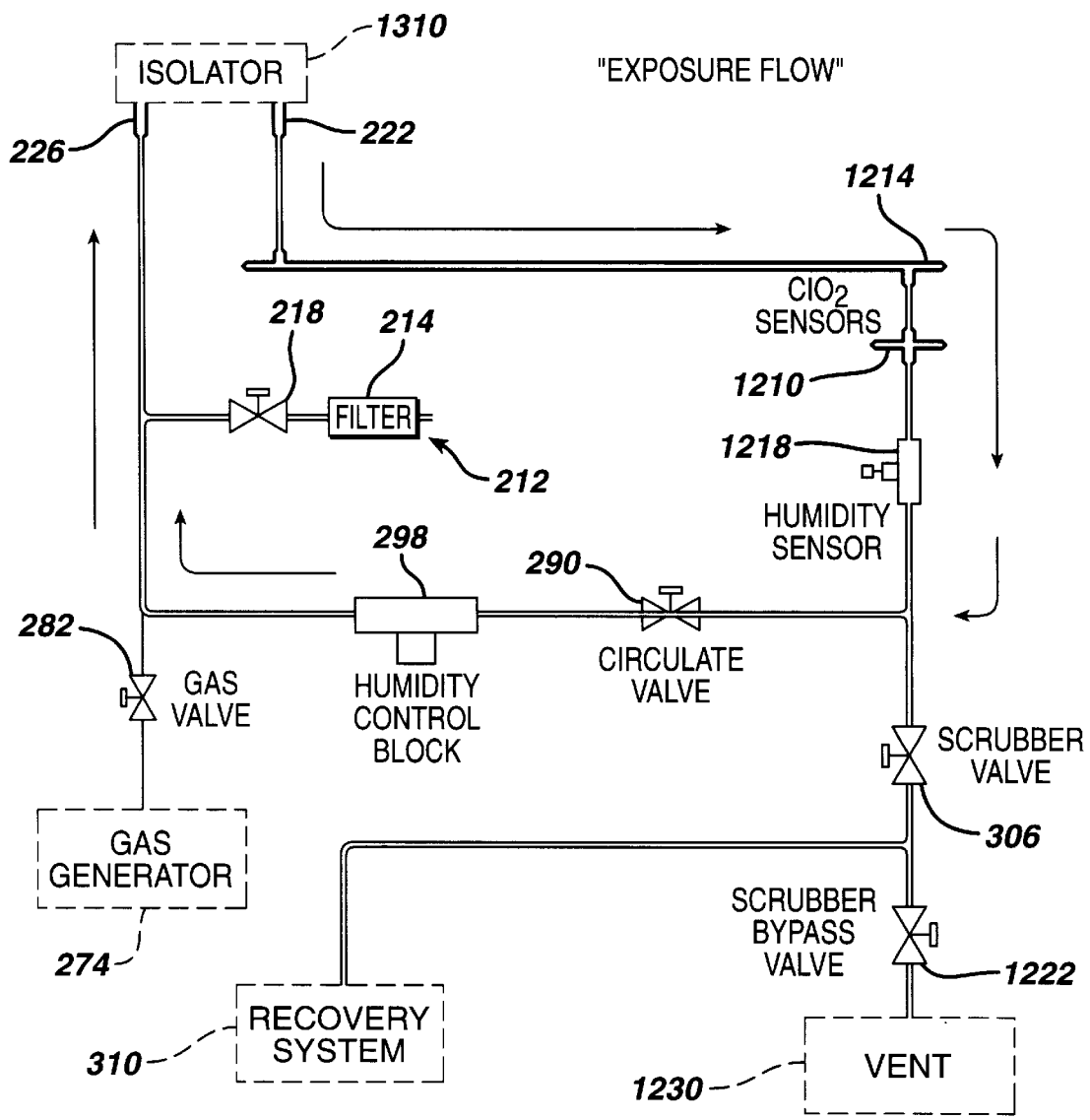
FIG. 44 is essentially the same view as FIG. 42 but illustrating an "exposure flow" mode of operation.
Figure 45:
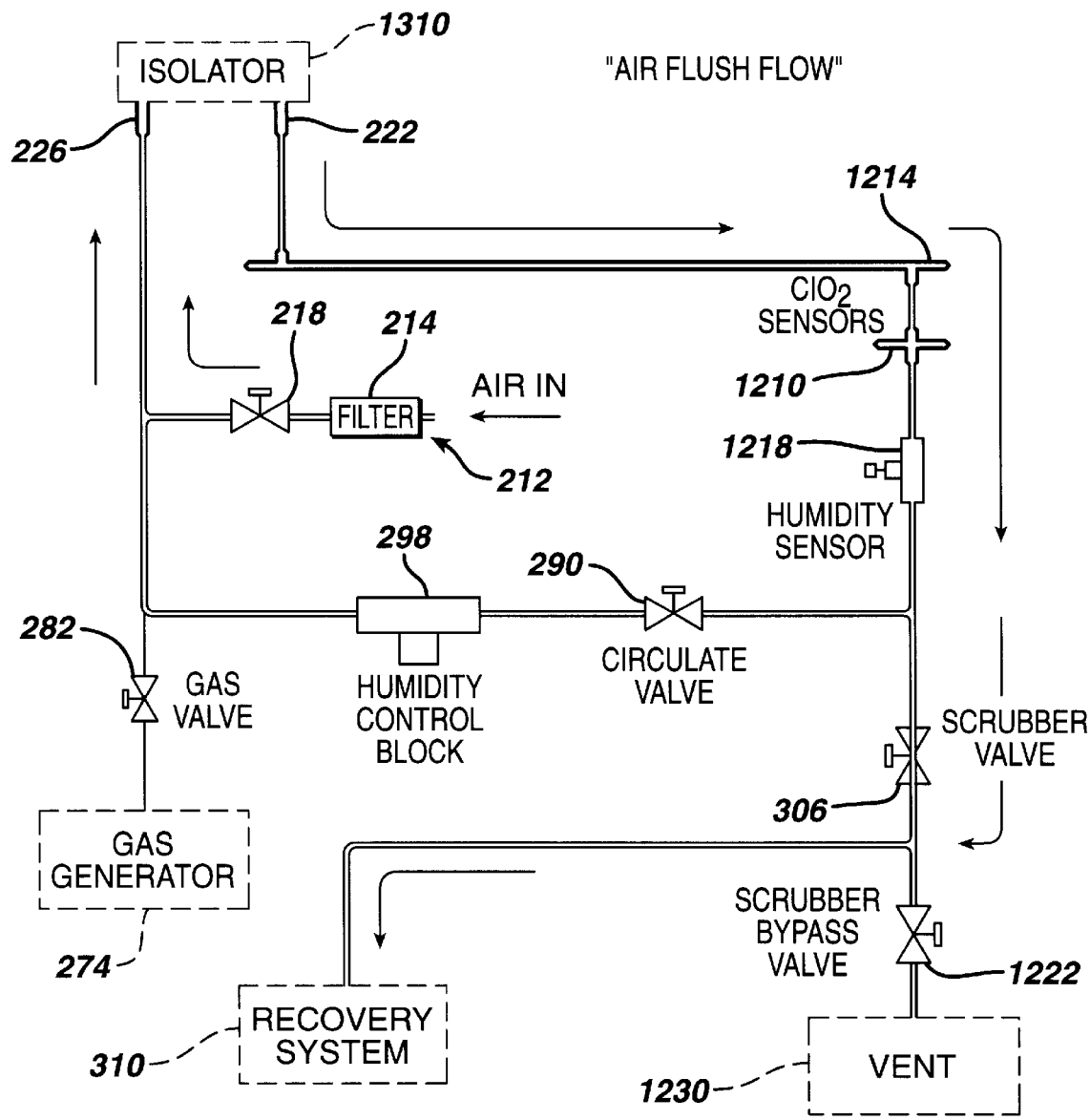
FIG. 45 is essentially the same view as FIG. 42 but illustrating an "air-flush flow" mode of operation.

As a brief preliminary review, it will be appreciated that:

a "circulate flow" mode of operation, as illustrated in FIG. 42, could involve the closed-loop circulation of air or other gas initially contained within isolator 1310, prior to any sterilant gas being introduced, and could also involve the control of system humidity;

a "gas injection flow" mode of operation, as illustrated in FIG. 43, could involve the wholesale injection of sterilant gas into the isolator proper, with subsequent measurements being made so as to insure that only a predetermined quantity of sterilant gas is actually introduced;

an "exposure flow" mode of operation such as that illustrated in FIG. 44 could involve the continuous recirculation of sterilant gas into and out of isolator 1310 for a predetermined period of time; and an "air-flush flow" mode of operation, such as that illustrated in FIG. 45, could involve the flushing and/or recovery of sterilant gas from isolator 1310 by introducing fresh air (or other suitable gas) into isolator 1310 and forcing all sterilant gas out through the recovery system 310.

FIG. 42 illustrates a "circulate flow" diagram and illustrates many of the components shown in FIG. 41, plus a filter 214 at "air in" portion 212. (Conceivably, filter 214 could be a standard anti-contamination filter, configured for removing significantly sized particulates from the incoming airstream, while the filtering of smaller particulates could take place via a filter, e.g. a "HEPA" filter, at isolator 1310.) As shown, in the "circulate flow" mode, gas will preferably be removed from isolator 1310, transported through inlet portion 222 and thence to cross-line 286 (see FIG. 41), followed by its being returned to isolator 1310 through outlet portion 226. Preferably, the appropriate control valves can be controlled by appropriate programming and/or software in order to effect the mode illustrated in FIG. 42.

FIG. 43 is substantially the same as FIG. 42 but illustrates a mode of "gas injection flow". In this mode, gas will preferably be introduced into isolator 1310 via outlet portion 226. Excess pressure will vent out via inlet portion 222 and proceed to recovery arrangement 310 (see FIG. 41). Preferably, the appropriate control valves can be controlled by appropriate programming and/or software in order to effect the mode illustrated in FIG. 43.

FIG. 44 is substantially the same view as FIGS. 42 and 43, but illustrates an "exposure flow" mode. The flow is substantially similar to that shown in FIG. 42. Preferably, the appropriate control valves can be controlled by appropriate programming and/or software in order to effect the mode illustrated in FIG. 44 and maintain the same for a predetermined period of time.

FIG. 45 is substantially the same view as FIGS. 42, 43 and 44, but illustrates an "air flush flow" mode. Similarly to the "gas injection flow" mode illustrated in FIG. 43, gas will preferably proceed from inlet portion 222 to recovery arrangement 310 (see FIG. 41). However, in contrast to the "gas flow" mode illustrated in FIG. 43, air will preferably proceed into that line which leads to outlet portion 226 via "air in" portion 212. Preferably, the appropriate control valves can be controlled by appropriate programming and/or software in order to effect the mode illustrated in FIG. 45.

It will be appreciated that valve 1222 illustrated in FIG. 41 and also in FIGS. 42–45 may be considered a "scrubber bypass valve". With this "scrubber bypass valve" closed, gas will preferably proceed directly into the scrubber proper (if it has already passed valve 306). (In the alternative, "scrubber bypass valve" 1222 may open if a sufficient amount of at least one active ingredient has been recovered, so that the gas may then exit the system via vent 1230.)

It will be appreciated that, in accordance with at least one preferred embodiment of the present invention, the various modes of operation described and illustrated heretofore with relation to FIGS. 42 through 45 may be realized in a suitable manner, especially via control of the appropriate valves. Thus, in one embodiment of the present invention, there may preferably be provided an automatic arrangement for opening and closing each of the valves 218, 282, 290, 306 and 1222 at the appropriate times, or at least in response to actions initiated by an operator (e.g., via pressing of buttons). It is also conceivable to maximally automate the transitions from one mode of operation to the other. For example, it is conceivable for the transition between the "sterilant injection flow" mode illustrated by FIG. 43 to the "exposure flow" mode illustrated in FIG. 44 by automatically transmitting data from either or both of the $ClO_2$ sensors 1210, 1214 to a central processing unit which, upon attainment of an acceptable threshold value, can proceed to close scrubber valve 306 and open circulate valve 290.

It will further be appreciated that other components of a gas generating system according to the present invention can be integrated into a maximally automated apparatus. For example, the "humidity control block" 298 illustrated in FIGS. 41 through 45 may be configured to automatically regulate humidity. This may be accomplished by suitable methods of feedback that would appear to be well-known to those of ordinary skill in the art.

Figure 46:
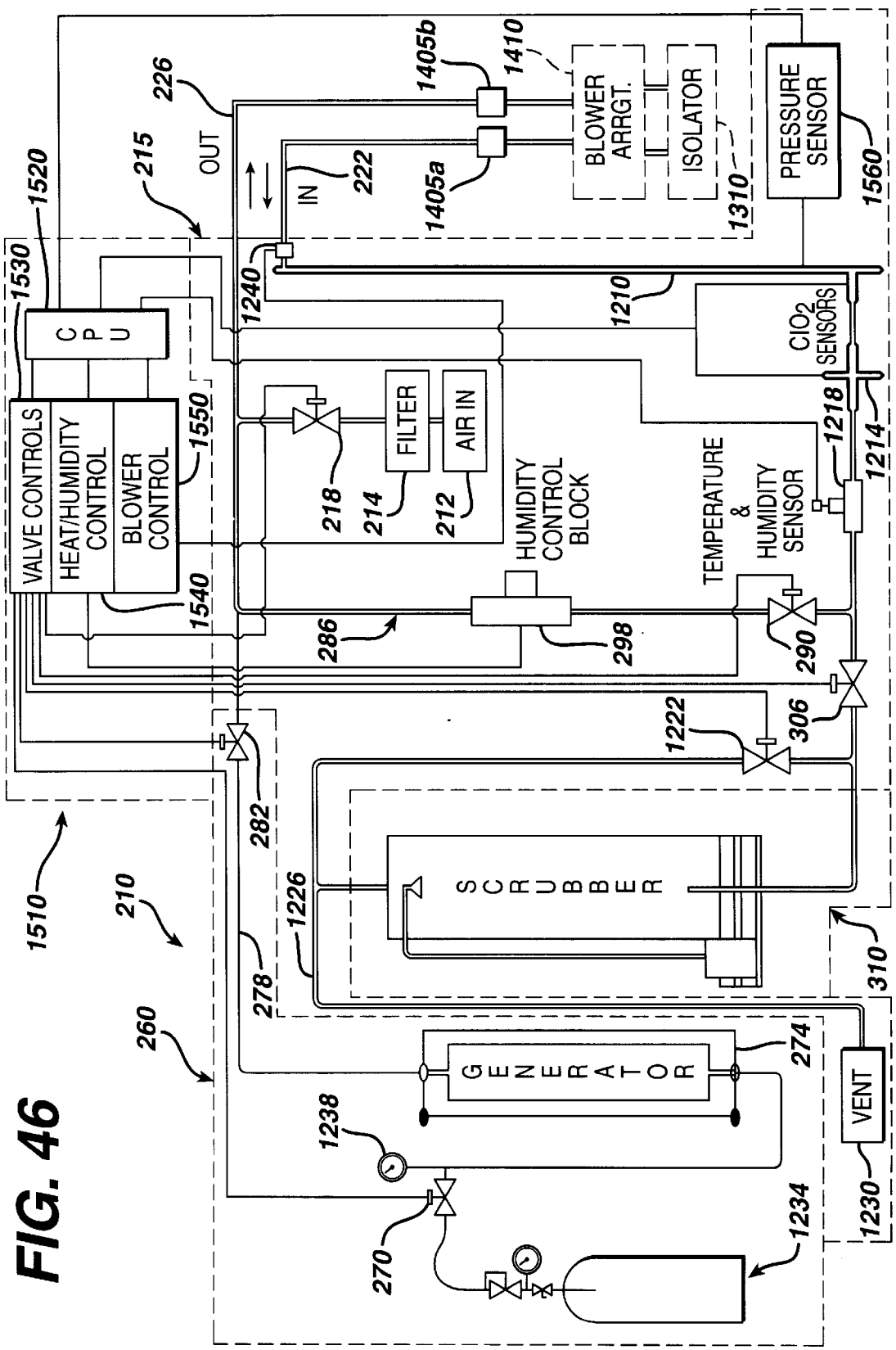
FIG. 46 is essentially the same view as FIG. 41 but additionally illustrating a control arrangement.

FIG. 46 illustrates, in schematic form, a general control arrangement 1510 that may be utilized in accordance with at least one preferred embodiment of the present invention.

As shown, control arrangement 1510 may include a central processing unit (CPU) 1520 for accepting inputs from pressure sensor 1560 (attached to isolator 1310 and configured for measuring the pressure therewithin), chlorine dioxide sensors 1210 and 1214 and temperature/humidity sensor 1218. In turn, the control arrangement 1510 also preferably includes dedicated controls for the valves 1530, temperature and humidity 1540 and for the system blower 1550. Particularly, valve control 1530 will preferably serve to selectively actuate any or all of the valves 218, 270, 282, 1222, 306 and 290; heat/humidity control 1540 will preferably serve to control the system temperature heat and humidity via heat/humidify block 298; and blower control 1550 will preferably serve to control one or more components of a system blower arrangement (such as that indicated at 1240).

The disclosure now turns to several specific manners of manipulating the various components of a gas generating system according to the present invention, to achieve a wide range of objectives.

A general scheme for operating a gas generating system according to the present invention will now be described.

First, it may be assumed that the apparatus is separate from the enclosed space which it is intended to sterilize or decontaminate.

The enclosed space will likely have one inlet connection and one outlet connection.

In accordance with a preferred embodiment of the present invention, the inlet and outlet portions of the enclosed space, as well as the inlet and outlet portions of the sterilizing apparatus, may be embodied by suitable foolproof connections. Essentially, any suitable type of "foolproof" connection scheme can be employed for this purpose. For example, in one embodiment of the present invention, it is possible to utilize two different male/female connection schemes, albeit in which the male and female portions will be split between the sterilizing apparatus and the isolator or enclosed space. In other words, the inlet and outlet portions of the sterilizing apparatus will preferably include one male connection and one female connection (not necessarily in that order) and the inlet and outlet portions of the isolator or enclosed space will preferably include a male portion that is compatible with the female portion of the sterilizing apparatus and a female portion that is compatible with the male portion of the sterilizing apparatus (not necessarily in that order). Thus, providing that the correct male and female connections have been provided at the appropriate inlet or outlet portion of either the sterilizing apparatus or the isolator/enclosed space, a foolproof connection scheme can be obtained that, subsequent to the initial installation of the connection scheme, will ensure that the outlet portion of the sterilizing apparatus will always be correctly connected to the inlet portion of the isolator/enclosed space and that the outlet portion of the isolator/enclosed space will always be correctly connected to the inlet portion of the sterilizing apparatus.

It is now to be understood that subsequent operations carried out by the sterilizing apparatus and in conjunction with the enclosed space in question can progress in a manner and at a rate desired by the operator or operators. However, if it is indeed desired to conduct a sterilizing operation, there will likely need to be some assurance that other startup operations are conducted first. In this context, however, it is conceivable to either sequence such operations automatically or to initiate each individual operation with a manual stimulus, such as the pressing of a button by an operator. Both scenarios will be treated in the present discussion.

Therefore, once the sterilizing apparatus is connected with the enclosed space, at least a first operation, i.e., the "circulate flow" mode, will preferably be conducted. The actual manner for controlling circulation between the isolator and sterilizing apparatus, at least in accordance with a preferred embodiment of the present invention, is described herebelow in a different section of this disclosure.

In order for the "circulate flow" mode to be undertaken, as illustrated in FIG. 42, assuming the construction shown, the following criteria will need to be fulfilled:

scrubber valve 306 will need to be closed, circulate valve 290 will need to be open;

gas valve 282 (and preferably also the gas feed valve 270 shown in FIG. 41) will need to be closed (with gas generator 274 preferably shut off); and control valve 218 will need to be closed.

As a first step in the "circulate flow" mode, the blower 1240 will preferably be activated, thus at least enabling air circulation.

In the context of a "flexible-walled" isolator, it will be desirable to close valve 290 (the "circulate" valve) and open valve 306 (the "scrubber valve") for the purpose of deflating the isolator 1310 to allow for a given volume of sterilant to be injected.

Once isolator 1310 is properly deflated and/or evacuated, as determined by parameters preferably stored in the central processing unit 1520 (see FIG. 46), valves 218 and 306 can be closed while valve 290 can be opened; this will effect the "circulate flow" mode.

In the context of a "rigid-walled" isolator, a different type of charging will take place, a preferred example of which is discussed herebelow in the section entitled "Flow-Based Charge Algorithm . . . ".

At this point, if desired, circulation can continue without the introduction of any sterilant gas, with a view to adjusting the humidity present within the circulating air. It is conceivable to conduct a predetermined number of cycles of flow until a predetermined level of humidity is established, as sensed by the humidity sensor at 1218 and as controlled by humidity control block 298. Appropriate feedback circuitry can be used for this purpose. Conceivably, after such a desired level of humidity is obtained, a visual or audible signal could be provided to the operator, confirming that actual operations within the enclosed space or isolator 1310 can take place (being that the desired humidity is present within the isolator 1310).

In one embodiment of the invention, there may be an automatic transition between the "circulate flow" mode and the "gas injection flow" mode, after the air present in the system has circulated a predetermined number of times and after it has been determined that there is no leakage (or at least leakage above a predetermined and pre-programmed safety threshold) in the system. In the alternative, a visual or audible signal could be provided to the operator when such a stage has been reached, so as to prompt the operator to press a button, or provide some other mechanical or electronic stimulus, in order to initiate the next stage.

With reference to FIG. 43, then, either via automatic transition or via manual intervention by the operator, the transition to "gas injection flow" will preferably be made. Upon initiation of this stage, circulate valve 290 will preferably close, while gas valve 282 will preferably open, and scrubber valve 306 will preferably open as needed to maintain isolator pressure or system pressure.

Gas generator 274 may then be activated in a conventional manner (including the opening of valve 270) and may introduce into isolator 1310, via inlet 226, sterilant gas, such as chlorine dioxide gas. Upon the sterilant gas (mixed with air) exiting from isolator 1310 via connection 222, measurements of chlorine dioxide concentration can preferably be taken by either or both of the sensors 1210 and 1214. Via feedback control, upon the attainment of a given concentration of chlorine dioxide in the system, as determined by either or both of the sensors, a signal will preferably be sent automatically to affect transition to the next mode, this being the "exposure flow" mode.

In transitioning between the "gas injection flow" mode and the "exposure flow" mode", scrubber valve 306 will preferably close, along with the opening of circulate valve 290 and the closing of gas valve 282.

During the "exposure flow" mode, conceivably when operations are carried out within isolator 1310 as desired, it is conceivable to continually monitor the concentration of sterilant gas circulation within the system (via chlorine dioxide sensors 1210 and/or 1214) as well as the level of heat and humidity. If, at any time these parameters stray outside of a predetermined range (as preferably stored in the central control system), visual and/or audible signals could be provided to the operator in order to prompt him or her to either stop the operation or adjust the parameters accordingly. Alternatively, these parameters could be adjusted automatically via an appropriate feedback system controlled by the central control system.

Once the desired operations within isolator 1310 are completed and it is desired to at least temporarily cease operation of the sterilizing apparatus and isolator 1310, a transition can then preferably be made into the "air flush flow" mode, as illustrated in FIG. 45. Preferably, this transition will be effected manually, as the operator will likely be aware of when the transition is to be made (alternatively, however, it is conceivable to effect an automatic transition after a predetermined amount of time has expired, and this could be accompanied by a visual/audible signal to attract the operator's attention).

In effecting the transition to the "air flush flow" mode, circulate valve 290 will close, control valve 218 will open and scrubber valve 306 will open. At this point, scrubber bypass valve 1222 will preferably be closed, in order that all of the exiting gas may proceed to the recovery system 310.

Control of the "air flush flow" mode may take place in any number of ways, some of which have been described already heretofore with reference to recovery system 310. As described in that section, there may be provided another chlorine dioxide sensor which, in a suitable manner, can monitor the gas that is about to pass through the scrubber 334 and be exhausted to the ambient atmosphere. It is conceivable, for given concentrations of chlorine dioxide in the gas, for the gas to be vented via valve 1222 to vent 1230. This type of control can also take place by using sensors 1210 and 1214.

From the foregoing, it will be appreciated that one significant advantage of a system according to at least one preferred embodiment of the present invention is found in the feedback monitoring of gas (or fluid) concentration. Particularly, with continual recirculation of gas into and out of the target volume, it is possible to continuously monitor the gas concentration and provide make-up if needed. Thus, if the system has a leak, it is overcome (through make-up) much more quickly and reliably than in a conventional system in which there is no recirculation.

ARRANGEMENT FOR ADAPTING A GAS GENERATION AND RECOVERY SYSTEM TO A TARGET VOLUME

It will now be appreciated that, in accordance with at least one preferred embodiment of the present invention, a sterilizing apparatus according to the present invention can be easily integrated with a wide variety of target volumes, such as isolators or other enclosed spaces.

In this manner, it will be appreciated that only two connections to the isolator will be required, namely at an inlet to the isolator and at an outlet from the isolator. Such connections, for example, are indicated at 1405a and 1405b in FIG. 46.

Figure 47:
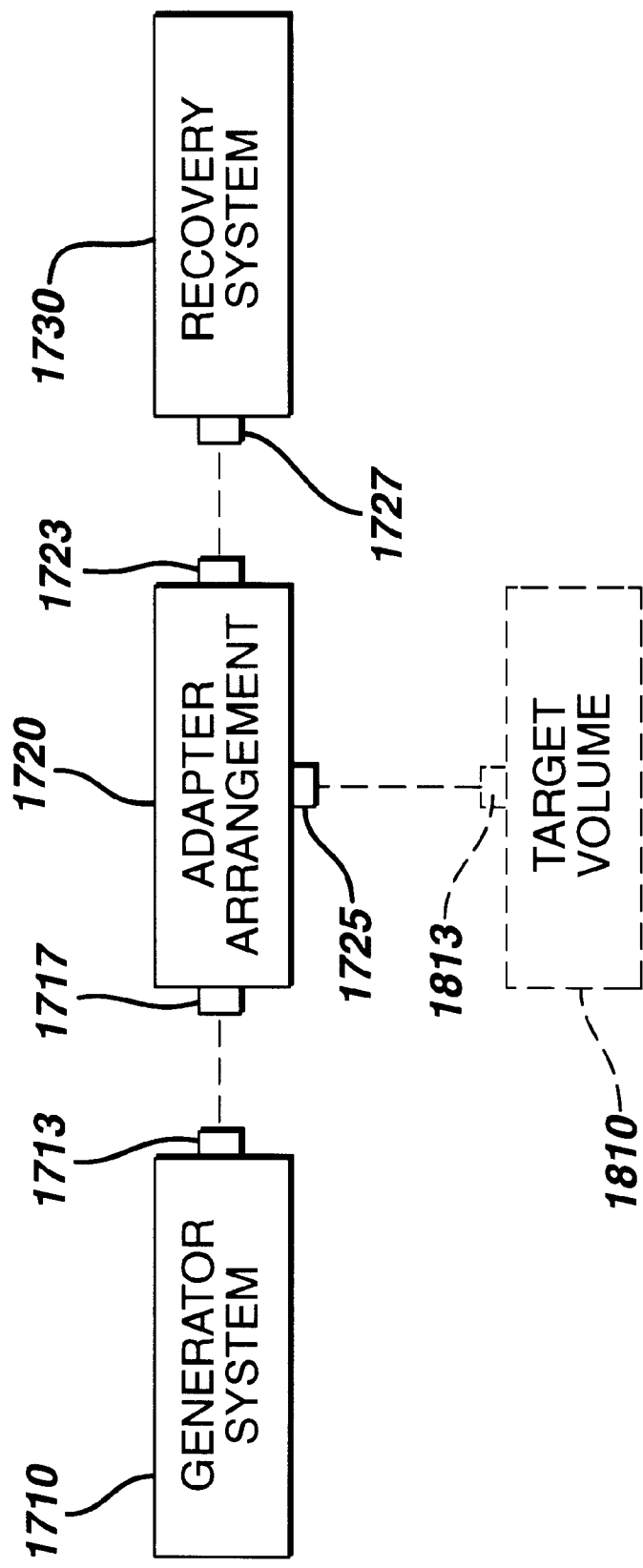
FIG. 47 schematically illustrates a concept of modular, interchangeable and selectively integrable sections in accordance with at least one embodiment of the present invention.

FIG. 47 illustrates, in accordance with a preferred embodiment of the present invention, a concept of modular, interchangeable and selectively integrable sections. Indicated at 1710 is a generator system, which, for example, could correspond to the dotted section 260 shown in FIGS. 8 and 41 (i.e. that section containing components relating to the generation of sterilant gas). Section 1720, on the other hand, may be considered an "adapter arrangement" and which, for example, could correspond to the dotted section 215 shown in FIGS. 8 and 41 (i.e. that section containing components serving to administer gas from an isolator or other enclosed space, extract it therefrom and either recirculate it or direct it to a recovery arrangement). Further, recovery system 1730 could be embodied as yet another modular section and could, for example, correspond to the dotted section 310 shown in FIGS. 8 and 41 (i.e. that section containing components serving to exhaust spent gas to the ambient atmosphere and/or recover predetermined portions of the same).

Thus, in this manner, it will be appreciated that a multi-portioned modular arrangement is contemplated, in which each of the three aforementioned modular components (generator system 1710, adapter arrangement 1720 and recovery system 1730) can be singular, discrete entities that are selectively integrable with one another or with other compatible modular components. For this purpose, each modular component will preferably bear an interface or connection scheme that allows it to be readily integrable with other modular components. Thus, generator system 1710 will preferably have an interface or connection scheme 1713 that permits facilitated connection with an interface or connection scheme 1717 of an adapter arrangement 1720. Likewise, adapter arrangement 1720 will preferably have an interface or connection scheme 1723 that permits facilitated connection with an interface or connection scheme 1727 of a recovery system 1730. Finally, adapter arrangement 1720 will preferably have an interface or connection scheme 1725 that permits facilitated connection with an interface or connection scheme 1813 of a given target volume 1810 (i.e. a microbial isolator or other enclosed space).

Referring now back to FIG. 8 as a non-restrictive example, it will be appreciated that the interfacing of connection schemes 1713 and 1717 might occur, for example, at a point between valve 282 and the intersection with cross-line 286. Further, the interfacing of connection schemes 1723 and 1727 might occur, for example, at a point between valve 306 and junction 314. Also, referring to FIG. 46 as a non-restrictive example, it will be appreciated that the interfacing of connection schemes 1725 and 1813 might occur at the location of connections 1405a and 1405b. In any event, it will be appreciated that the general arrangement of modular components and connection schemes illustrated in FIG. 47 broadly contemplates a wide range of connection schemes and modularities that can be configured and arranged in essentially any manner deemed suitable.

It will also now be appreciated that the modular arrangement described and illustrated herein with respect to FIG. 47 permits tremendous flexibility and versatility in that a wide variety of components embodying the generator system 1710, adapter arrangement 1720 and recovery system 1730 can be interchanged with respect to one another, allowing for a wide range of permutations in assembling an overall system for generating, administering, extracting and recovering a gas (such as a sterilant or decontaminant gas). Of course, such permutations will be governed by their practicability, but it will be appreciated that a degree of versatility is afforded that might not have been previously realizable. Additionally, in the event that one or another modular section requires repair or replacement, the modular system contemplated herein would appear to result in reduced costs, in that only one portion of the entire system would need to be repaired or replaced.

Furthermore, overall arrangements of a generator system 1710, adapter arrangement 1720 and recovery system 1730 can be configured and arranged so as to be collectively compatible with a given target volume 1810.

Additionally, it is possible for the modularity of the system described herein to allow for the following possibilities: the use of one or more generator systems 1710 without the use of a recovery system 1730; the use of one or more recovery systems 1730 without the use of a generator system 1710; and the use of neither a generator system 1710 nor a recovery system 1730 (wherein an adapter arrangement 1720 is provided solely for the purpose of recirculation).

In accordance with at least one presently preferred embodiment of the present invention, all instruments for measuring system parameters (such as, for example, instruments similar to the concentration sensors 1210/1214, temperature/humidity sensor 1218 and pressure sensor 1560 all described and illustrated with respect to FIGS. 41 and 46) may be contained within the adapter arrangement 1720 of the modular system. In this manner, it would not be necessary to ensure, in the context of a given modular adapter arrangement 1720, for any target volume 1810 with which the adapter arrangement 1720 is to be connected to contain any such instruments. Thus, the instruments in adapter arrangement 1720 can essentially be applied for use in conjunction with any of a significant number of different target volumes 1810, thus precluding the need either for supplementary instrumentation (which would be added as a temporary adjunct to a connected adapter-target volume system) or for instrumentation in the target volume itself, thus potentially realizing a significant cost savings.

Insofar as a target volume 1810, such as an isolator or other enclosed space, might be equipped with one or more of its own blowers, it is conceivable, in accordance with an embodiment of the present invention, to also include one or more blowers within the adapter arrangement 1720 (for example, in a manner similar to that illustrated in FIG. 41 with regard to blower 1240). In this manner, the flow of gas within the entire connected system, including that into and out of target volume 1810, can be "boosted" by such an additional blower. Likewise, the modular arrangement illustrated in FIG. 47 permits the incorporation of adapter arrangements 1720 that lack blowers, and that would subsequently rely solely on the isolator blower for gas propagation and recirculation (this variant might be suitable, for example, in the context of small target volumes 1810 that might not require large flowrates for gas introduction, extraction and recirculation.

Figure 48:
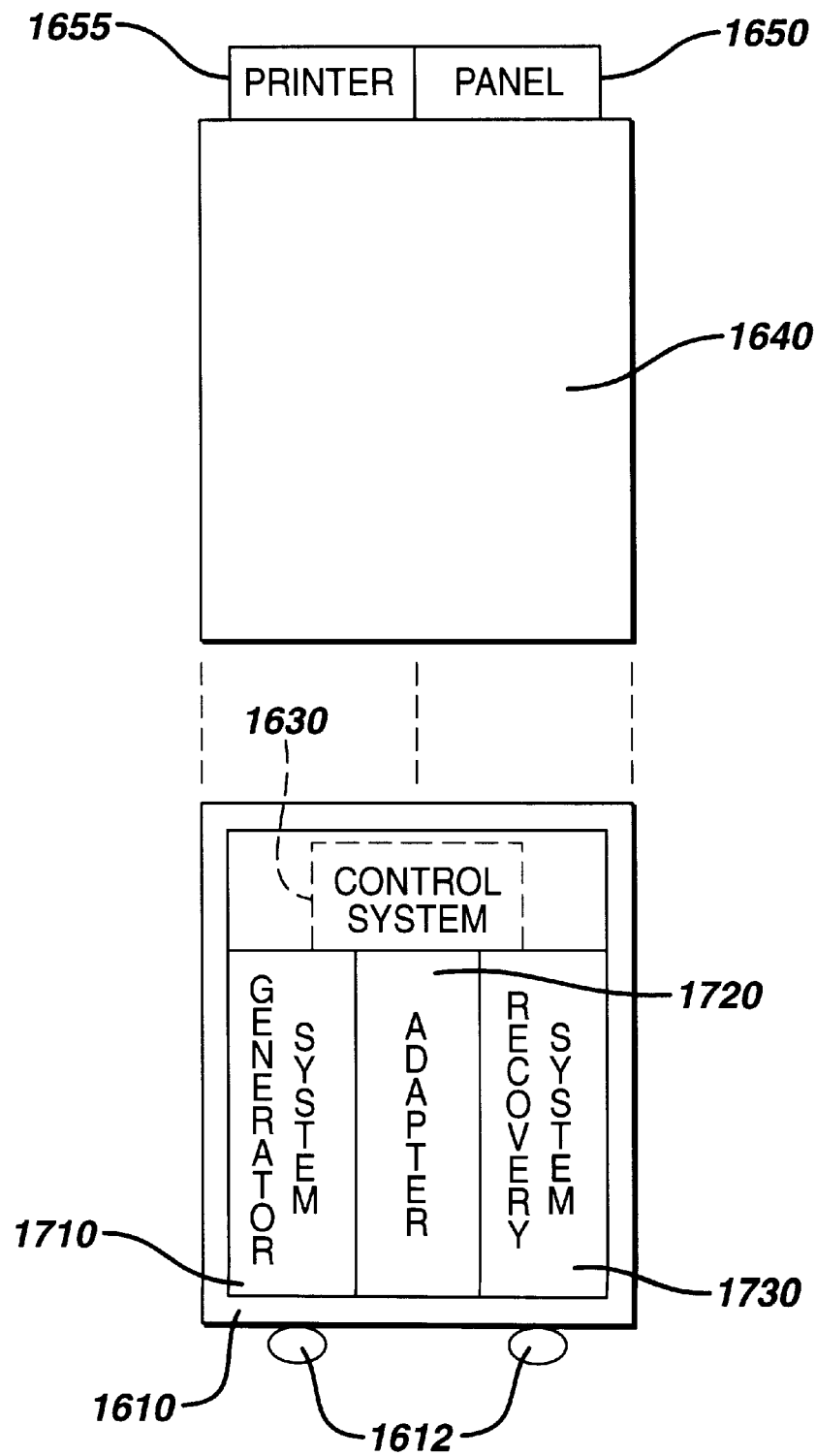
FIG. 48 illustrates an assemblage of components according to the principles illustrated by FIG. 47.

Thus, FIG. 48 illustrates an embodiment of the present invention in which a cart arrangement is employed according to the principles illustrated by FIG. 47. In this manner, cart 1610 may simultaneously bear suitably configured and arranged modular sections 1710, 1720 and 1730, for use with a designated target volume. Additionally, a control system 1630, suitably configured and arranged for the modular sections 1710, 1720 and 1730 being used, can also be borne on the cart 1610.

In accordance with one embodiment of the present invention, a sterilizing apparatus according to the present invention can essentially include the components illustrated schematically in FIG. 48, namely a general frame 1610, a control system 1630 and a system case 1640.

In accordance with a preferred embodiment of the present invention, the aforementioned frame may be embodied by a wheeled cart (with wheels 1612), which cart can serve both as a structural frame and as a means for moving the sterilizer apparatus.

A control arrangement according to the present invention, such as that indicated schematically at 1630 in FIG. 48 and/or 1510 in FIG. 46, can be located in a non-conducting box with a see-through door, and the box can be mounted to the system cart.

Finally, a stainless case 1640 can cover the system cart and be bolted in place, or otherwise secured, with respect thereto. Preferably, the case 1640 will be so configured and arranged as to protect the system, prevent tampering, and provide a working surface. Preferably, the case 1640 will also be equipped with doors which open to provide access for replacement of any consumable components of the system.

For the purposes of operator interface, essentially any suitable arrangement can be used, such as a 9-inch square LCD panel 1650 and a printer 1655. Both of these components may also be so configured and arranged as to mount readily on the system case. In a conventional manner, such an LCD panel could include labeled touch surfaces for being activated by an operator.

Figure 49:
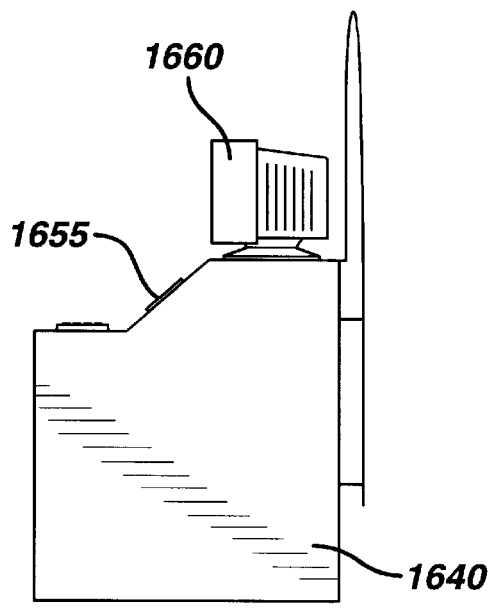
FIG. 49 illustrates a possible external configuration of an assemblage of components according to the present invention.
Figure 50:
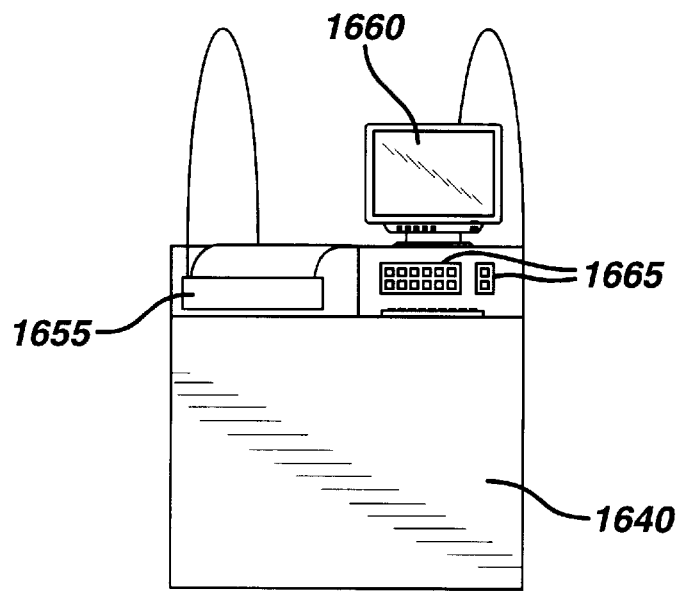
FIG. 50 is an alternative view of the arrangement illustrated in FIG. 49.

A possible external configuration is illustrated in FIGS. 49 and 50. As shown, there may be provided, atop casing 1640, a conventional CRT monitor 1660, operator keypad or keypads 1665 and printer 1655.

Figure 51:
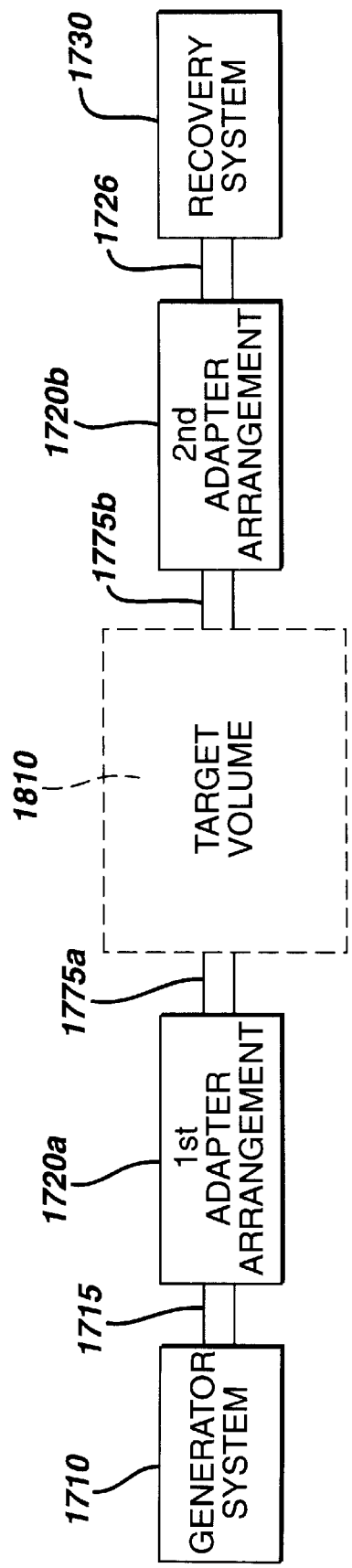
FIG. 51 illustrates a variant concept of modular, interchangeable and selectively integrable sections.

FIG. 51 illustrates a variant arrangement in which a significantly large target volume 1810 might be adopted (e.g. a significantly large room that is designated for sterilization or decontamination or even a large portable space, similarly designated, such as the interior of a hold on an 18-wheeler truck). In this variant arrangement, generating system 1710, conceivably configured for generating a sterilant or decontaminant gas, feeds into a first adapter arrangement 1720a via a general connection scheme 1715. In turn, this first adapter arrangement may feed into the target volume 1810 via a general connection scheme 1775a. Further, target volume 1810 may (via a general connection scheme 1775b) feed into a second adapter arrangement 1720b, which in turn feeds into recovery system 1730 via a general connection scheme 1726.

Thus, in accordance with the embodiment illustrated in FIG. 51, two separate adapter arrangements may be employed. In one variant, the feed from the first adapter arrangement 1720a, to target volume 1810, and thence to second adapter arrangement 1720b, may be unidirectional and linear (i.e. all sterilant or decontaminant gas entering target volume 1810 will subsequently be drawn out and then exhausted). In another variant, either or both of the adapter arrangements 1720a/b may serve to recirculate sterilant gas that has been introduced into target volume 1810. For example, first adapter arrangement 1720a could introduce sterilant gas at the top left of target volume 1810 (with respect to the view illustrated in FIG. 51 and also extract the same from the bottom left of target volume 1810. Additionally, second adapter arrangement 1720b could extract sterilant gas from the upper right of target volume 1810 and then reintroduce it into target volume 1810 at the bottom right thereof. In this manner, a "figure-8" pattern of continuous recirculation could be applied to target volume 1810. For this purpose, especially in the context of significantly large target volumes 1810, each adapter arrangement 1720a/1720b may be provided with its own blower.

In order for any control system to maintain communication with all attendant modular sections (1710, 1720a, 1720b and 1730) in the variant shown in FIG. 51, essentially any suitable means of remote communication may be employed (i.e. radio transmission, wire transmission, "ethernet", etc.)

The present invention, in accordance with at least one presently preferred embodiment, may be viewed as broadly contemplating a modular system for decontaminating at least a portion of a target, the modular system comprising:

at least one modular section (A) comprising an arrangement for:
selectively administering the decontaminant gas to the target; and selectively recirculating gas back to the target; and
at least one of:
at least one modular section (B) comprising an arrangement for generating a decontaminant gas; and
at least one modular section (C) comprising an arrangement for selectively extracting decontaminant gas away from the target.

CONTROL PROGRAMMING ARRANGEMENT

The disclosure now turns to a control programming arrangement that may be utilized in accordance with the embodiments of the present invention.

Generally contemplated is a self-validating arrangement that ensures the accurate execution of the constituent steps of a sterilization process. All functions and process steps are self-monitoring. Any failure is promptly alarmed and, where appropriate, elicits an automated response.

Preferably, a modular and template-based software architecture will direct the programmer in the context of setting up an autonomous (i.e. customized) sterilization routine, upon the introduction of a sterilizing apparatus of the present invention to a new operating environment (i.e. a new isolator or other enclosed space). Finally, when implemented, the system will be self-validating at two levels. At one level, the elements of the software templates will provide a step-by-step checklist for testing the system and process operation. Further, every production cycle step includes hard-coded validation parameters, whereby the activation of a designated "validation" switch will preset the system to execute a process-validating version of the next cycle to run.

In accordance with preferred embodiment of the present invention, several properties will be employed in the software templates, as briefly outlined herebelow.

The control arrangement (such as that indicated at 1510 in FIG. 46) will continuously monitor all utilities and instruments. Any failure detected with respect to any item will set an alarm and consequently disable the next process "start" step; conversely, in the absence of any alarm, the next process "start" step will be enabled.

All functions and steps are monitored for successful startup and execution as appropriate to the function or step. Any detected failure will activate an appropriate alarm that will subsequently identify the failure by step or function.

In the context of a sterilizing procedure performed in accordance with the present invention, one and only one step will be active at any given time, most particularly those steps described and illustrated hereinabove with respect to FIGS. 42 through 45, among others. Further, if a given step is detected as not being active at any point in time, or if more than one step is detected as being simultaneously active at any point in time, then the control arrangement (such as that indicated at 1510 in FIG. 46) will preferably enter an abort sequence that will guarantee a safe return to a controlled state.

Inasmuch as each of the steps comprising a portion of a sterilizing process according to the present invention will be governed, to some extent, by the time in which they are active, a "process halt" provision will preferably be employed in which, if any step fails to complete in a maximum allowable time (and as stored, for example, in a portion of the memory of the CPU 1520 shown in FIG. 46), an appropriate alarm (e.g. audible, visual, printed, etc.) can be activated to alert the operator or operators into intervening.

In the event that such an alarm state is activated but no operator intervention occurs over a predetermined period of time, the control arrangement will preferably prompt the sterilizer to enter an abort sequence appropriate to the failed step, thus guaranteeing a safe return to a controlled state.

Finally, if conditions exist, at any step in the sterilizing process, that could otherwise compromise safety or threaten product integrity (e.g. threaten the sterility or physical properties of an item being subjected to sterilization within the isolator or other enclosed space), the process will abort in a manner appropriate to the active step.

Steps can be activated by one of two methods:

"Sequential Step Activation" (SSA) ensures absolute control of step sequencing in a pre-determined sequence of steps. The only process step capable of starting at the end of any current step is the next programmed step. At all times a pre-programmed abort step is ready to activate if required by process necessity or operator input.

"Random Step Activation" (RSA), on the other hand, permits operator definition of a sequence of steps which will comprise an ad-hoc custom sterilization sequence. The custom sequence is generated by associating the ordinal process step (1 through n) with a step specific code to identify the required step functions. Process or timing setpoints will be associated with each step as required. As the custom cycle executes, the step number will increment 1 through n as each step completes successfully. If a process abort is required, the RSA sequence will be disabled. The pre-programmed abort step will activate and the process will follow the programmed abort sequence to a safe condition. This random step activation method is appropriate for process development and testing. It provides flexibility with security, but is generally not appropriate for validated production systems.

A programming arrangement, in accordance with an embodiment of the present invention, may now be appreciated with reference to the accompanying FIGS. 52 through 58. FIGS. 52 through 58 each illustrate programming templates that can be used for all functions of a sterilizing process and that can be duplicated and edited (i.e. customized) as needed. The examples shown in FIGS. 52 through 58 are presented in conventional ladder logic; however, it is to be understood that the methods and templates contemplated herein can be used with essentially any suitable programming language. Continued reference will also be made to FIGS. 41 through 46, where appropriate.

First, it will be appreciated that each process step in a sterilizing procedure (e.g. circulation flow, sterilant injection flow, etc.) includes one or more functions. Such functions include, for example, gas injection (i.e. the opening of a valve such as valve 282 in FIGS. 41 through 46) or vacuum generation (conceivably actuable by a conventional vacuum pump, to evacuate the interior of an isolator or other enclosed space 1310 and alternatively actuable by a blower arrangement, such as that indicated at 1410 in FIG. 46).

Preferably, each designated step will activate the appropriate actuators, or even a control loop that itself will activate the appropriate actuators, in order to carry out the function associated with the step. For example, a "gas injection step", in accordance with a preferred embodiment of the present invention, will prompt a control loop stored in CPU 1520 to: open valve 282; close valve 290; and open valve 306; via valve control arrangement 1530. Also, appropriate controls will also preferably activate the gas generator 274 itself.

Figure 52:
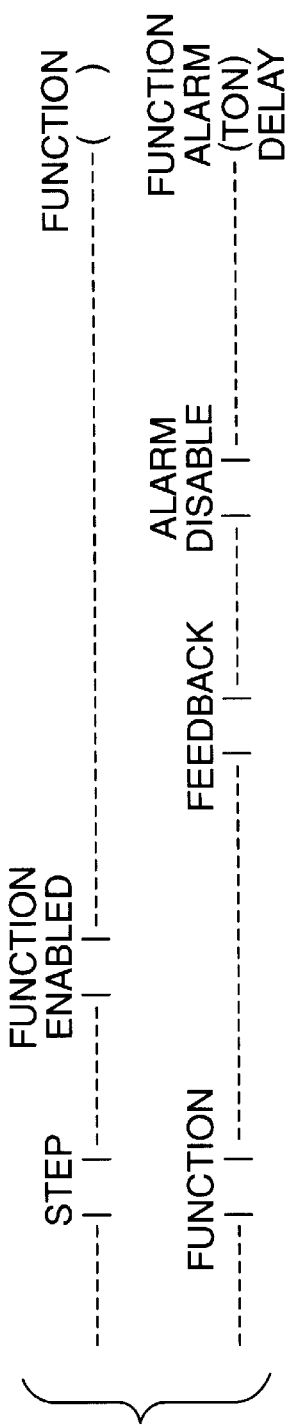
FIG. 52 illustrates, in ladder logic, a "function" programming template according to the present invention.

Accordingly, with reference to FIG. 52, it will be appreciated that the "function" template will serve to explicitly define the function at hand once the step is active.

The lower portion of FIG. 52 illustrates a "function monitoring" scheme. Particularly, since every function results in an initial change in system parameters, such an initial change can be employed to prompt the relevant control loop that the function has actually begun. In so doing, the alarm associated with that function can be disabled from the outset, until such a time that the predesignated system parameters may be violated.

In accordance with a preferred embodiment of the present invention, the template arrangements contemplated herein will preferably be configured so that each step monitors its own progress and completion. Particularly, pre-set time-based alarms are preferably provided that will signal improper step completion, or step failure. Generally, a failed step will activate an alarm, at which point the step in question will terminate and will not continue without operator intervention. If no operator intervention occurs within a specified period of time, the pre-programmed abort sequence will execute and the system will return to a controlled state.

Figure 57:
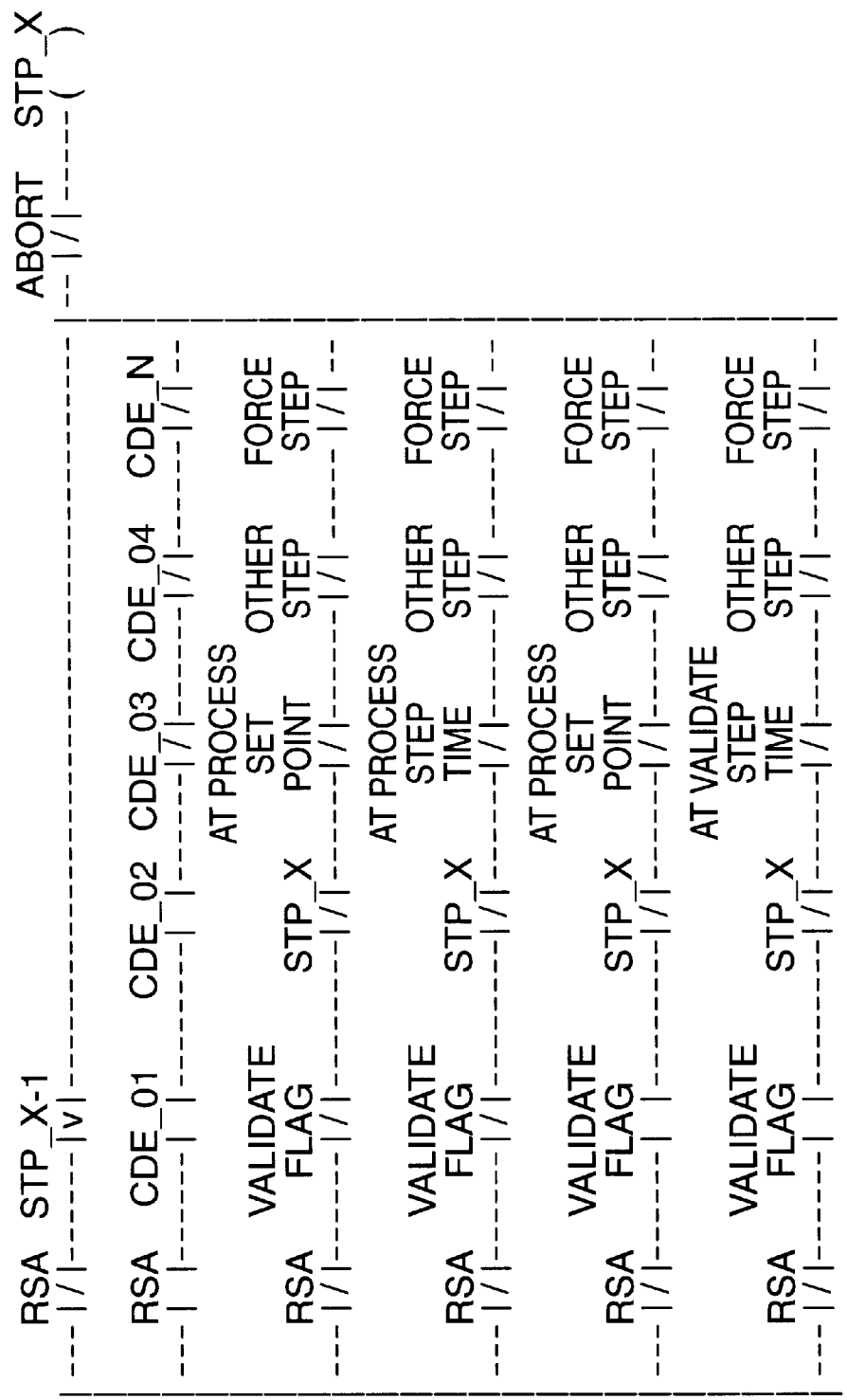
FIG. 57 illustrates, in ladder logic, a step control scheme.

A "setpoint-driven" step will execute until a predetermined process value is achieved. An example of this is sterilant gas injection (see FIG. 43), which will preferably continue until a predetermined concentration of sterilant gas is detected by sensors 1210/1214. A simple inequality will preferably latch the step until the setpoint is met (i.e. if the measured parameter value, such as sterilant gas concentration, is not equal to the predetermined desired concentration, the step will continue executing). FIG. 57 illustrates setpoint latching for setpoint steps.

A "time-driven" step will continue only for a predetermined period of time, and will thus end when the predetermined time has expired. In accordance with an embodiment of the present invention, the step timer can be disabled for any time interval in which given step parameters are not satisfied. Again, a simple inequality will preferably latch the step until the time requirements are met (i.e. if the elapsed time is not equal to the predetermined time, the step will continue). FIG. 57 also illustrates time-based latching for time-based steps.

Occasionally, a "compound" step may also be required, in which case the step will continue until both a setpoint is met and a required period of time has expired. Thus, such steps will include two latches, one for the setpoint and the other for time.

Figure 53:
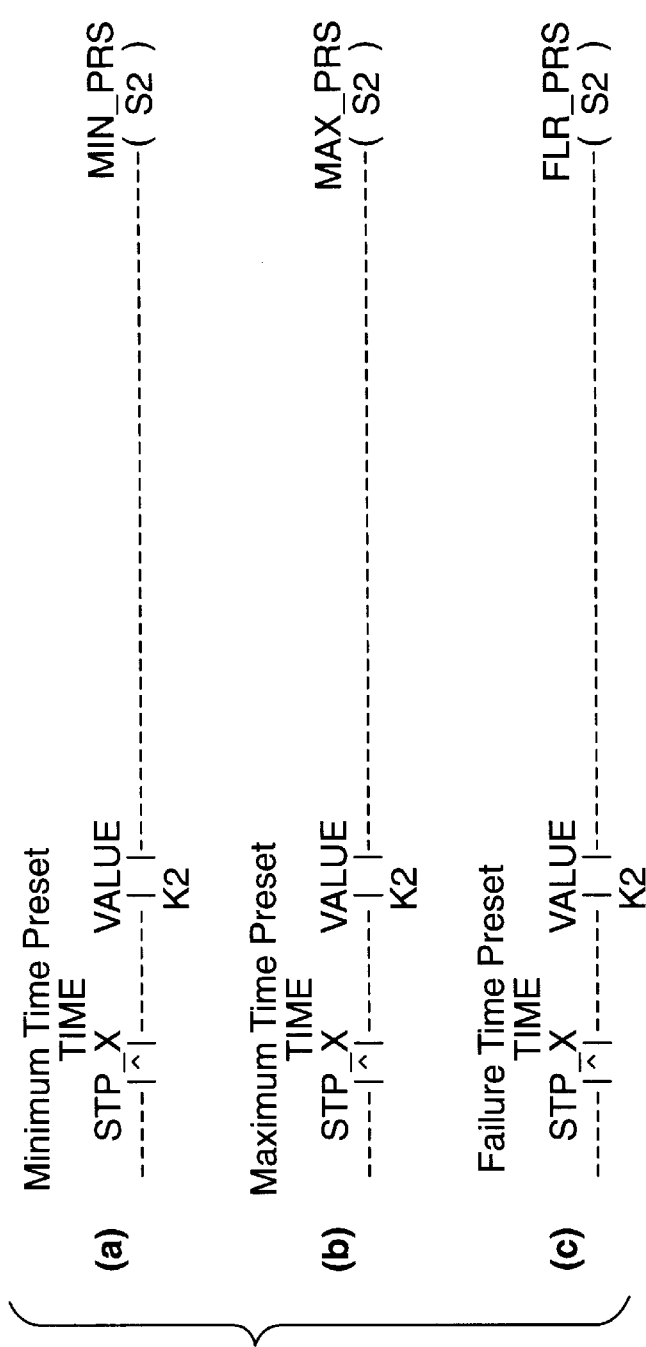
FIG. 53 (*a* through *c*) illustrates, in ladder logic, various "step time" presets.
Figure 54:
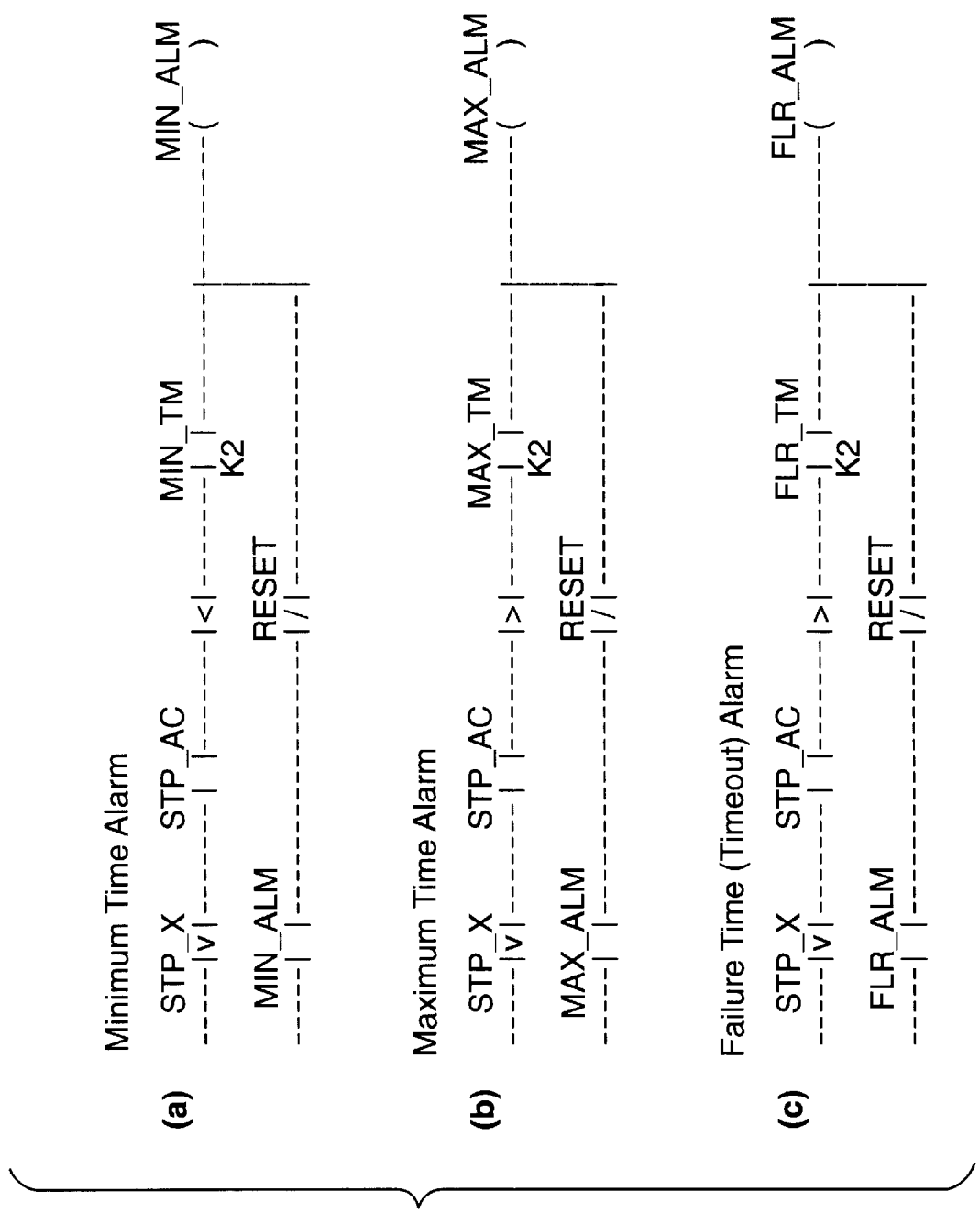
FIG. 54 (*a* through *c*) illustrates, in ladder logic, alarms employing the presets shown in FIG. 53 (*a* through *c*)

FIG. 53 (a through c) illustrates various step time presets that may be employed in accordance with an embodiment of the present invention and that may subsequently be employed to prompt corresponding alarms.

FIG. 53(a) shows a "minimum time" timer preset, which will serve prompt the activation of a "minimum time" alarm if a step completes in less time than a predetermined lower boundary value.

FIG. 53(b) shows a "maximum time" timer preset, which will serve to prompt the activation of a "maximum time" alarm if a step continues past a predetermined maximum time limit.

FIG. 53(c) shows a "step fail" timer preset, which will serve to abort the step being performed, or even the entire sterilization process, if a step continues after a "maximum time" alarm and no operator intervention occurs after a specified period of time in alarm (i.e. a specified period of time in an "alarm" state).

FIGS. 54(a) through (c) illustrate actual alarms employing the presets shown in FIGS. 53(a) through (c).

Figure 55:
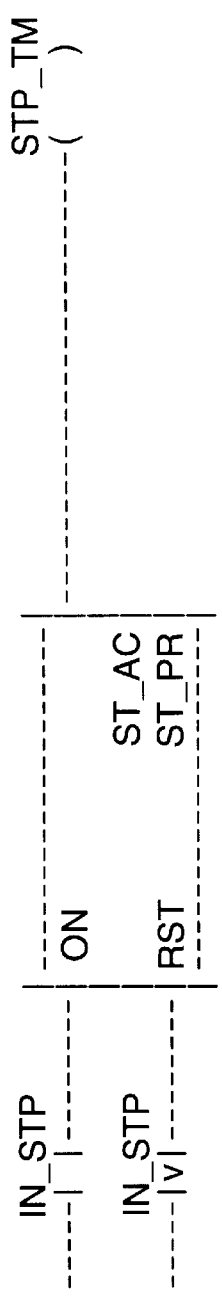
FIG. 55 illustrates, in ladder logic, a "time in step" timer.
Figure 56:
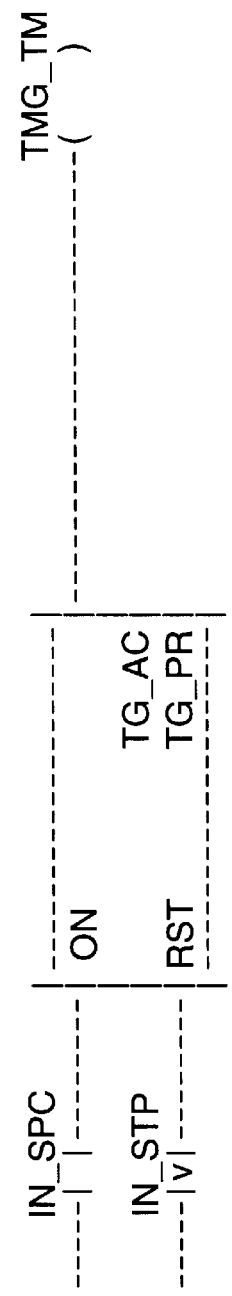
FIG. 56 illustrates, in ladder logic, a "time made good" timer.

Preferably, two step timers will be used to monitor step execution, both of which are reset when a new step starts. For example, shown in FIG. 55 is a "time in step" timer that serves to record the time that has elapsed in the step. On the other hand, a "time made good" timer, such as that expressed in FIG. 56, records the cumulative time during which step parameter requirements were met. This "time made good" will then provide the basis for meeting the required time in step as defined in the process specification.

Turning now to FIG. 57, contemplated therein is a step control scheme that can allow for the selection of either sequential step activation (SSA) or random step activation (RSA), as explained below.

If SSA is selected, then step X is activated when Step X-1 completes. In this method one and only one of two steps is competent to activate when the preceding step completes. The normal step (see FIG. 57) activates if the preceding step completed normally without the abort condition set. The abort step (see FIG. 58) is activated if the current step ends in an abort condition.

If RSA is selected, then step-X is activated when the operator selected code is true. The code is one of a sequence which may be sequenced by one of the following methods. Other methods may be used, but these are the most common:

1. Manual Sequencing: The operator will enter the code and setpoints for the current step.
2. Tenor Drum: A sequence of pre-configured codes and setpoints will be driven by the completion of process steps.
3. Set Point Programming (SPP): A programming tool of the Honeywell Control Software system, which provides a time and process driven sequence of numeric codes and corresponding setpoints.

To simplify programming, as shown in FIG. 57, RSA is programmed but SSA is not explicitly defined. When RSA is inactive (FALSE), then SSA is active by default.

Figure 58:
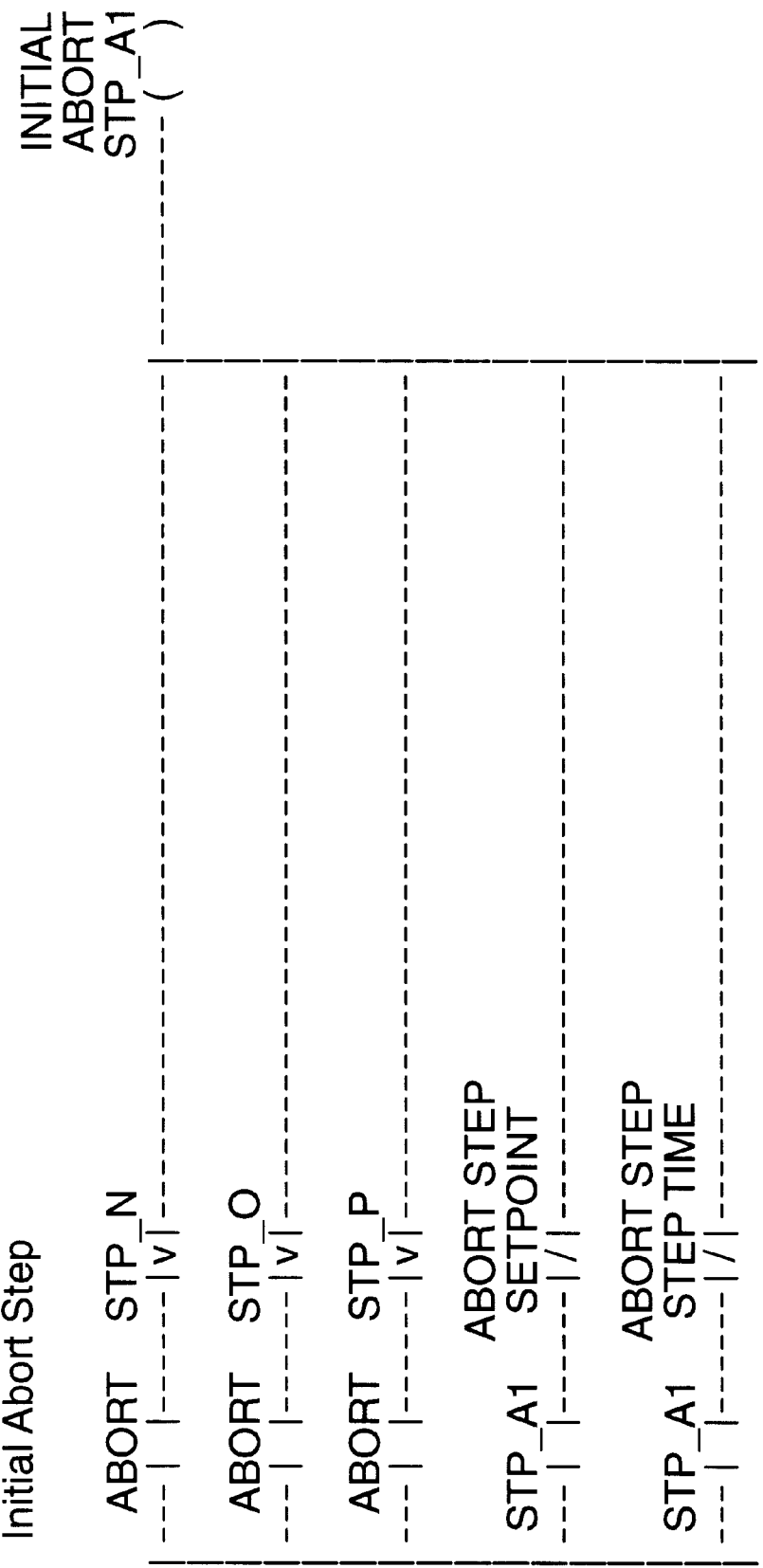
FIG. 58 illustrates, in ladder logic, an "abort step" control scheme.

Step completion is contemplated in accordance with the step templates shown in FIGS. 57 and 58.

When a process step has met its target setpoint or when the time in step has expired the step ends normally. The template shows that the step is latched on until both "STEP TIME" and "STEP SETPOINT" are made. Both must be made to break the latch as is appropriate to some steps; for most steps only one branch is used. Note that the process step branches are active in the absence of the "VALIDATE" flag, and process setpoints and values are in effect.

On the other hand, when the "validation" flag has been set by the operator, then the normal "STEP TIME" and "STEP SETPOINT" branches are inactive and the VALIDATE TIME and VALIDATE SETPOINT branches are activated. The steps execute and terminate as described for Normal Step Completion, but validation time and setpoint values are in effect.

On operator command (preferably privileged operator command) the "FORCE STEP FLAG" will be active for one machine cycle. This will end the currently active step without regard to time instep or process condition. The following step will begin normally. The template shows that the step is unlatched when "FORCE STEP" is "TRUE". The broken latch ends the step. In a validated process, forcing a step constitutes a process deviation, and must be dealt with procedures appropriate to the process.

On operator command, or in response to process safety or product integrity requirements, the "ABORT FLAG" will be set "TRUE". The step templates in FIGS. 57 and 58 show that any process step, if active, is unlatched when "ABORT" is "TRUE" and, if inactive, is inhibited. This will initiate the pre-programmed abort sequence. The current step will end immediately. For any step in an aborted process there is one and only one possible next step, at the end of the abort sequence the system will be restored to a safe condition. An abort step template is presented in FIG. 58. Note the ABORT flag both initiates an abort and turns the Random Step Activation flag "OFF". The abort sequence is a special Sequential Step Activation sequence which cannot be aborted.

It will be appreciated that one set of timers serves all steps. At the beginning of any step the timer presets are reset by the new step and the timers restart.

Insofar as the sequencing described hereinabove can conceivably be initiated by manual activation by an operator, it will be appreciated that a process according to the present invention will render such sequencing automatic. Further, in the context of automatic sequencing, it will be appreciated that a process according to the present invention will permit the sequence, or any of the individual process steps, to be aborted in the event of a predetermined "failure".

Insofar as a sterilizing apparatus according to the present invention is intended to be readily adaptable to any of the wide variety of enclosed spaces intended to be sterilized, it will be appreciated that a process according to the present invention will also allow for some standardization of the processing sequences carried out. In other words, the template programming software according to the present invention provides a basic framework that is believed to be common to a very wide variety of sterilizing apparatus and processes, which framework however can be modified and built upon according to the requirements of the situation at hand.

For example, it is conceivable to provide a control arrangement in which the operator may pre-set parameter ranges for the sterilizing apparatus and process that are not to be violated and, if violated, will result in an alarm and/or abort, as discussed above.

It is also recognized that there may also exist parameters that will tend to fall in ranges that are common to a very wide range of sterilizing apparatus and processes. In this case, such parameters can already be pre-programmed into the controller in question.

It will be appreciated that the "self-validation" aspect of the present invention provides unique advantages in comparison with known arrangements. Particularly, much of the conventional validation software tends to be operationally disassociated from the software that actually conducts a sterilizing or decontaminating procedure. However, in accordance with at least one presently preferred embodiment of the present invention, the "self-validation" arrangement contemplated herein forms part of the very same arrangement that conducts a sterilizing/decontaminating procedure, in that, for the purpose of conducting a validation run, the template shown in FIG. 57, for example, need only be altered by "flagging" a validation run request. This may be accomplished, for example, by the operator merely pressing a button or providing some other type of stimulus.

It will further be appreciated that the template arrangement discussed herein permits at least two steps of a sterilizing operation to be automatically carried out in a predetermined or a predeterminable sequence. In accordance with at least one preferred embodiment of the present invention, a "predeterminable" sequence may be considered as being an "ad-hoc" sequence.

It will additionally be appreciated that the system discussed herein is "deterministic", in that it is capable of monitoring itself and determining whether it is properly executing a sequence step.

FLOW-BASED CHARGE ALGORITHM

The disclosure now turns to a description of a flow-based charge algorithm for gas delivery that may be utilized in accordance with at least one preferred embodiment of the present invention. This algorithm may be best appreciated with reference to FIGS. 41 through 46.

Generally, the concept of flow-based charging combines:
gas addition based on a calculated value; and
gas addition in response to feedback control.
to attain a desired concentration of the active gaseous agent while maintaining pressure at a near ambient setpoint.

This system may preferably be comprised of the loop indicated by the arrows in FIG. 43, along with the pressure monitor sensor 1560 and control 1510 shown in FIG. 46.

When flow-based charge is initiated, gas valve 282 is open. The active gas is admitted from gas generator 274 through valve 282, while any venting takes place through valve 306. Initial charge then continues for a time "T" as defined by the formula:

$$T = (VC/FR)K,$$

where:
V=Effective volume of vessel to be sterilized ($ft^3$).
C=Sterilizing concentration (mg/L).
F=Concentration of gas introduced at valve 282 (mg/L).
R=Flow rate of gas introduced at valve 282 ($ft^3$/minute)
T=Charge time (minutes).
K=Percent correction for chamber contents, or percent of unoccupied volume.

Following initial charge, circulation devices within as isolator or enclosed space 1310 will preferably be activated to uniformly disperse the active gas. If the control signal from the concentration sensor 1214 indicates that concentration is less than C, valves 270 and 282 will preferably open to admit additional gas.

During the "gas injection" phase (as shown in FIG. 43), valve 306 can preferably open to relieve excess pressure. Similarly, if the pressure monitor 1560 (or other pressure monitoring device) signals that pressure has reached or exceeded the set point, valve 306 will preferably be opened to maintain this pressure within the vessel (such as isolator 1310). When concentration C is obtained, a transition will be effected to the "exposure" phase shown in FIG. 44.

Thus, as a method is contemplated for introducing a predetermined gas volume into a leak tight vessel, the system will use valves to supply an active gas to the vessel and to remove gas as required to maintain pressure and concentration. Control arrangement 1510, including CPU 1520, will control the execution of a predetermined sequence of instructions. The method can apply to all types of isolators regardless of their intended internal pressure (i.e., whether at atmospheric pressure, vacuum, or positive pressure).

Thus, in accordance with a flow-based charging algorithm according to the present invention, it will be appreciated that, by eliminating the problem of pressure-based sterilization systems, the gaseous sterilization of essentially any enclosed volume is permitted. Small, pressure-sensitive microbial isolators may be sterilized/decontaminated without damage; this can also be accomplished in large industrial rooms or containers. In all cases, there is essentially no need to evacuate or otherwise manipulate the volume of the space to be sterilized. Further, the timed flow of sterilant gas of known concentration at a known flow rate permits direct calculation of the sterilant delivered. Further, concentration is monitored by a sensor (e.g. such as that indicated at 1214 in FIG. 46) and feed-back controlled by the computer, thus eliminating the indirect calculations common to pressure-based systems.

If not otherwise stated herein, it may be assumed that all components and/or processes described heretofore may, if appropriate, be considered to be interchangeable with similar components and/or processes disclosed elsewhere in the specification, unless an indication is made to the contrary.

It should be appreciated that the apparatus and methods of the present invention may be configured and conducted as appropriate for the application. The embodiments described above are to be considered in all respects only as illustrative and not restrictive. The scope of the invention is defined by the following claims rather than the foregoing description. All changes which come within the meaning and range of equivalency of the claims are to be embraced within their scope.

What is claimed is:

1. A modular system for decontaminating at least a portion of a target, said modular system comprising:

At least one modular section (A) comprising means for:
    selectively administering the decontaminant gas to the target; and
    selectively recirculating gas back to the target; and at least one of:
    at least one modular section (B) comprising means for generating a decontaminant gas; and
    at least one modular section (C) comprising means for selectively extracting decontaminant gas away from the target; means for accepting decontaminant gas that has been administered to a volume; and means for recovering at least one ingredient from decontaminant gas accepted by said accepting means, said recovering means comprising means for introducing a medium for interacting with the accepted decontaminant gas and permitting the recovery therefrom of at least one predetermined ingredient wherein at lease one of:
    said at least one modular section (A);
    said at least one modular section (B); and
    said at least one modular section (C);

is interchangeable with another of said modular sections, to permit the selective assembly of at least two different systems for decontaminating at least a portion of a target.

2. The modular system according to claim 1, wherein:
each modular section (B) comprises means for interfacing said modular section (B) in fluid communication with at least two different modular sections (A) on different occasions.

3. The modular system according to claim 1, wherein:
each modular section (C) comprises means for interfacing said modular section (C) in fluid communication with at least two different modular sections (A) on different occasions.

4. The modular system according to claim 1, wherein:
each modular section (A) comprises means for interfacing said modular section (A) in fluid communication with at least two different modular sections (B) on different occasions.

5. The modular system according to claim 1, wherein:
each modular section (A) comprises means for interfacing said modular section (A) in fluid communication with at least two different modular sections (C) on different occasions.

6. The modular system according to claim 1, wherein:
each modular section (A) comprises means for interfacing said modular section (A) in fluid communication with at least two different targets on different occasions.

7. The modular system according to claim 1, wherein:
each modular section (A) comprises means for interfacing said modular section (A) in fluid communication with at least two different targets on different occasions.

* * * * *